(12) United States Patent
Yano et al.

(10) Patent No.: US 11,926,655 B2
(45) Date of Patent: Mar. 12, 2024

(54) ACTIVE MMP9-BINDING PEPTIDE

(71) Applicant: Daiichi Sankyo Company, Limited, Tokyo (JP)

(72) Inventors: Hidenori Yano, Ota-ku (JP); Daisuke Nishimiya, Sumida-ku (JP); Ryuji Hashimoto, Yachiyo (JP); Yoichi Niitsu, Kashiwa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 753 days.

(21) Appl. No.: 16/631,394

(22) PCT Filed: Jul. 17, 2018

(86) PCT No.: PCT/JP2018/026732
§ 371 (c)(1),
(2) Date: Jan. 15, 2020

(87) PCT Pub. No.: WO2019/017338
PCT Pub. Date: Jan. 24, 2019

(65) Prior Publication Data
US 2020/0231654 A1 Jul. 23, 2020

(30) Foreign Application Priority Data
Jul. 18, 2017 (JP) ................. 2017-138998

(51) Int. Cl.
| | | |
|---|---|---|
| *C07K 14/81* | (2006.01) | |
| *A61K 38/00* | (2006.01) | |
| *A61K 47/62* | (2017.01) | |
| *A61K 47/68* | (2017.01) | |
| *C07K 14/00* | (2006.01) | |
| *C12P 21/02* | (2006.01) | |
| *G01N 33/68* | (2006.01) | |

(52) U.S. Cl.
CPC .......... *C07K 14/8135* (2013.01); *A61K 47/62* (2017.08); *A61K 47/68* (2017.08); *C07K 14/001* (2013.01); *C12P 21/02* (2013.01); *G01N 33/68* (2013.01); *A61K 38/00* (2013.01)

(58) Field of Classification Search
CPC .. C07K 14/8135; C07K 14/001; C07K 16/38; C07K 14/81; A61K 47/62; A61K 47/68; A61K 38/00; A61K 35/12; A61K 35/76; A61K 38/55; A61K 48/00; A61P 1/04; A61P 1/14; A61P 1/16; A61P 1/18; A61P 3/10; A61P 9/00; A61P 9/04; A61P 9/10; A61P 11/00; A61P 11/02; A61P 11/06; A61P 13/12; A61P 17/00; A61P 17/02; A61P 17/04; A61P 17/06; A61P 17/10; A61P 17/14; A61P 19/02; A61P 21/02; A61P 25/00; A61P 25/08; A61P 25/10; A61P 25/14; A61P 25/18; A61P 25/20; A61P 25/22; A61P 25/24; A61P 25/28; A61P 25/30; A61P 25/32; A61P 27/02; A61P 35/00; A61P 37/02; A61P 43/00; C12N 5/10; G01N 33/53; G01N 33/68; C12P 21/02
See application file for complete search history.

(56) References Cited

U.S. PATENT DOCUMENTS

| | | | |
|---|---|---|---|
| 5,958,699 A | 9/1999 | Bandman et al. | |
| 10,550,154 B2 * | 2/2020 | Nishimiya | ............. C07K 1/047 |
| 2015/0197546 A1 | 7/2015 | Nishimiya et al. | |

FOREIGN PATENT DOCUMENTS

| | | |
|---|---|---|
| WO | 2014/024914 A1 | 2/2014 |
| WO | 2016/023979 A1 | 2/2016 |

OTHER PUBLICATIONS

Andriy Yabluchanskiy,(Matrix Metalloproteinase-9: Many Shades of Function in Cardiovascular Disease (Physiology (Bethesda). Nov. 2013; 28(6): 391-403). (Year: 2013).*
Wenbo Hao et a Biochemical characterization of unusual meso-2,3-butanediol dehydrogenase from a strain of Bacillus subtilis Journal of Molecular Catalysis B: Enzymatic 109 (2014) 184-190 (Year: 2014).*
Goffin, L., et al., "Anti-MMP-9 Antibody: A Promising Therapeutic Strategy for Treatment of Inflammatory Bowel Disease Complications With Fibrosis," Inflammatory Bowel Disease 22(9):2041-2057, Sep. 2016.
International Search Report dated Oct. 23, 2018, issued in corresponding International Application No. PCT/JP2018/026732, filed Jul. 17, 2018, 4 pages.
Kherraf, Z.-E., et al., "SPINK2 Deficiency Causes Infertility by Inducing Sperm Defects in Heterozygotes and Azoospermia in Homozygotes," EMBO Molecular Medicine 9:1132-1149, May 2017.
Extended European Search Report dated Mar. 9, 2021 issued in corresponding Application No. 18836005.1, filed Jul. 17, 2018, 10 pages.
Yano, H., et al., "Discovery of Potent and Specific Inhibitors Targeting the Active Site of MMP-9 from the Engineered SPINK2 Library," PLoS ONE 15(12): 1-21, 2020.
Nishimiya, D., et al., "A Protein Scaffold, Engineered SPINK2, for Generation of Inhibitors with High Affinity and Specificity Against Target Proteases," Scientific Reports 9(11436): 1-11, 2019.

* cited by examiner

*Primary Examiner* — Delia M Ramirez
(74) *Attorney, Agent, or Firm* — Christensen O'Connor Johnson Kindness PLLC

(57) ABSTRACT

The present invention provides a novel peptide that has an amino acid sequence represented by SEQ ID NO: 18, and binds to an active protease but does not bind to a proprotease.

9 Claims, 30 Drawing Sheets
Specification includes a Sequence Listing.

| | | |
|---|---|---|
| HUMAN_MMP-9_P14780 | 250 SDGLPWC...TTANYD DRRGFCPSERLYTQD GKFCPCVFPFIFEGRSY 299 |
| CYNO_MMP-9_XP_005569271 | 250 SDGVPWC...TTANYD DRRGFCPSERLYTQD GKFCPCVFPFIFQQSY 299 |
| RAT_MMP-9_P50282 | 251 NDGFPWC GTTADYD DKYGFCPSERLYTEHGN GKPCVFPFIFEGHSY 300 |
| MOUSE_MMP-9_P41245 | 250 NDGTPWC TTADYD DKRGFCPSERLYTEHGNGEKPCVFPFIFEGRSY 299 |
| | |
| HUMAN_MMP-9_P14780 | 300 SACTTDGRSDGYRWCATTANYD RDKLYGFCPTR DSTV GGNSAGE CVF 349 |
| CYNO_MMP-9_XP_005569271 | 300 SACTTDGRSDGYRWCATTANYD DKY GFCPTR DSTVI GGNSAGE CVF 349 |
| RAT_MMP-9_P50282 | 301 SACTTNGRSDGYRWCATTANYD ADGFCPTQ BVIV EGNSAGE CVF 350 |
| MOUSE_MMP-9_P41245 | 300 SACTTKGRSDGYRWCATTANYD DKYGFCPTRVDATV GGNSAGE CVF 349 |
| | |
| HUMAN_MMP-9_P14780 | 350 PFTFLGKEYS CTSGRSDGRIWCATTSNFD DKKWGFCPDGYSLFLVA 399 |
| CYNO_MMP-9_XP_005569271 | 350 PFTFLGKEYS CTSSGRGDGRIWCATTSNFD DKKWGFCPDGYSLFLVA 399 |
| RAT_MMP-9_P50282 | 351 PHVFLGKQYS CTSSERSDGRIWCATTSNFD ADKRWGFCPDGYSLFLVA 400 |
| MOUSE_MMP-9_P41245 | 350 PFVFLGKQYS CTSDERRDGRIWCATTSNFD DKKWGFCPDGYSLFLVA 399 |
| | |
| HUMAN_MMP-9_P14780 | 400 AHEFGHALGLDHS SVPEALMYP YRFTEGPPL DVNGIRHLYGPRPEP 449 |
| CYNO_MMP-9_XP_005569271 | 400 AHEFGHALGLDHS SVPEALMYP YRFTEEPTH DVRGIQYLYGSRPEP 449 |
| RAT_MMP-9_P50282 | 401 AHEFGHALGLRHT SVPEALMYP YHYHEDSPT EDIHGIHHLYGRGSNP 450 |
| MOUSE_MMP-9_P41245 | 400 AHEFGHALGLDHS SVPEALMYP LYSYLEGFPNK DIEGIQYLYGSKP 449 |
| | |
| HUMAN_MMP-9_P14780 | 450 EFRPPTTT... PQPTAPPTVC PTGPF VHESERFA PTGPPSAGPT--- 495 |
| CYNO_MMP-9_XP_005569271 | 450 ERRPPTTT... PQPTAPPTVC TGPF VHEAERF A PTGPPSAGPT--- 495 |
| RAT_MMP-9_P50282 | 451 DPRPFATTAAEPQPTAPPTVC STAPPMAYPGGPTVAPTGAPSPGPHL--- 498 |
| MOUSE_MMP-9_P41245 | 450 DPRPFATTTEPQPTAPPTVC THPPTAYPGPTVPGPEVPTGAPSPGPHSSP 499 |

Figure 1(C)

| | | | |
|---|---|---|---|
| HUMAN_MMP-9_P14780 | 496 | ---------------PPTAG|STTTVP|SPVD|ACNV|PDA|IGNOL | 531 |
| CYNO_MMP-9_XP_005569271 | 496 | ---------------PPTAG|STTTVP|SPVD|ACNV|PDA|IGNOL | 531 |
| RAT_MMP-9_P50282 | 499 | ---------------PPTAG|SERPE|STPDNP|NVD|VPDA|HDQGAL | 534 |
| MOUSE_MMP-9_P41245 | 500 | SPGPTGAPSPGFTAEPTASS|ESTES|SFAEN|PCNV|VFDA|LDQGAL | 549 |

| | | | |
|---|---|---|---|
| HUMAN_MMP-9_P14780 | 532 | YLEKDGKWPPGC|RFQGPFL|ADKMPAPF|LSVE|ERLSK|ALFF | 581 |
| CYNO_MMP-9_XP_005569271 | 532 | YLEKDGRWPPGC|RE|SR|QGPFL|ADWMPA|PRL|SPPE|PLSK|ALFF | 581 |
| RAT_MMP-9_P50282 | 535 | HFFKDGKYWRF|NEHGSNQLQGFFL|ARWPA|FPSI|FDQPK|IFF | 584 |
| MOUSE_MMP-9_P41245 | 550 | HFFNDGKYWKFLNHR|SFLQGFFITAR|WPAIPATL|SFEDDKRVFF | 599 |

| | | | |
|---|---|---|---|
| HUMAN_MMP-9_P14780 | 582 | FSVT|VYVYTGASVLGPR|HIDKLGLGA|VAQV|GAFRSGRGK|MLL|SGRR | 631 |
| CYNO_MMP-9_XP_005569271 | 582 | FSOV|WYTGSVLGFR|LDKLGLGAD|VAQV|GAPRGGK|MLL|SGRR | 631 |
| RAT_MMP-9_P50282 | 585 | FLNAQ|WYTQS|VLGRS|LDRIGLG|SEVI|GLPPRGK|PAL|ISRER | 634 |
| MOUSE_MMP-9_P41245 | 600 | FSOQ|WYTEGKTVLGRS|LDKLGL|GPEV|HVSCL|PRTLG|ALL|SKGR | 649 |

| | | | |
|---|---|---|---|
| HUMAN_MMP-9_P14780 | 632 | LFFFDVKAQ|VDPRSASE|VDRMFP|GVFLDTH|FQY|REKAYFC|QDRFYW | 681 |
| CYNO_MMP-9_XP_005569271 | 632 | FWFEDVAQ|VDPRSASE|VDRMPP|GVFLDTH|FQR|DKAYFCQ|DRFYWR | 681 |
| RAT_MMP-9_P50282 | 635 | INKFDIS|QAVDPQ|SVTRLDNEFS|GVPNNSHW|FQY|ODKAYFC|HDKYFFWR | 684 |
| MOUSE_MMP-9_P41245 | 650 | VNFFDIKSQKVDPQ|SVINDKEFS|GVPNNSH|DIFQY|DKAYFC|HGNRFWR | 699 |

| | | | |
|---|---|---|---|
| HUMAN_MMP-9_P14780 | 682 | VSRSEIN|---------|QVDQ|VGYVTYD|ILQCPED | 707 |
| CYNO_MMP-9_XP_005569271 | 682 | VSSQSGN|---------|QVDQV|GYVTYD|ILQCPED | 707 |
| RAT_MMP-9_P50282 | 685 | VSFHNRN|---------|QVDHV|AVVTYD|ILQCP--- | 708 |
| MOUSE_MMP-9_P41245 | 700 | VSFQNEI|KVDHEVN|QVEDV|NVTYD|ILQCP--- | 730 |

Figure 3

| Clone  | $EC_{50}$ (nM) |
|--------|----------------|
| M91001 | 22             |
| M91002 | 47             |
| M91004 | 42             |
| M91005 | 46             |
| M91010 | 48             |
| M91011 | 16             |
| M91012 | 46             |
| M91014 | 8.0            |

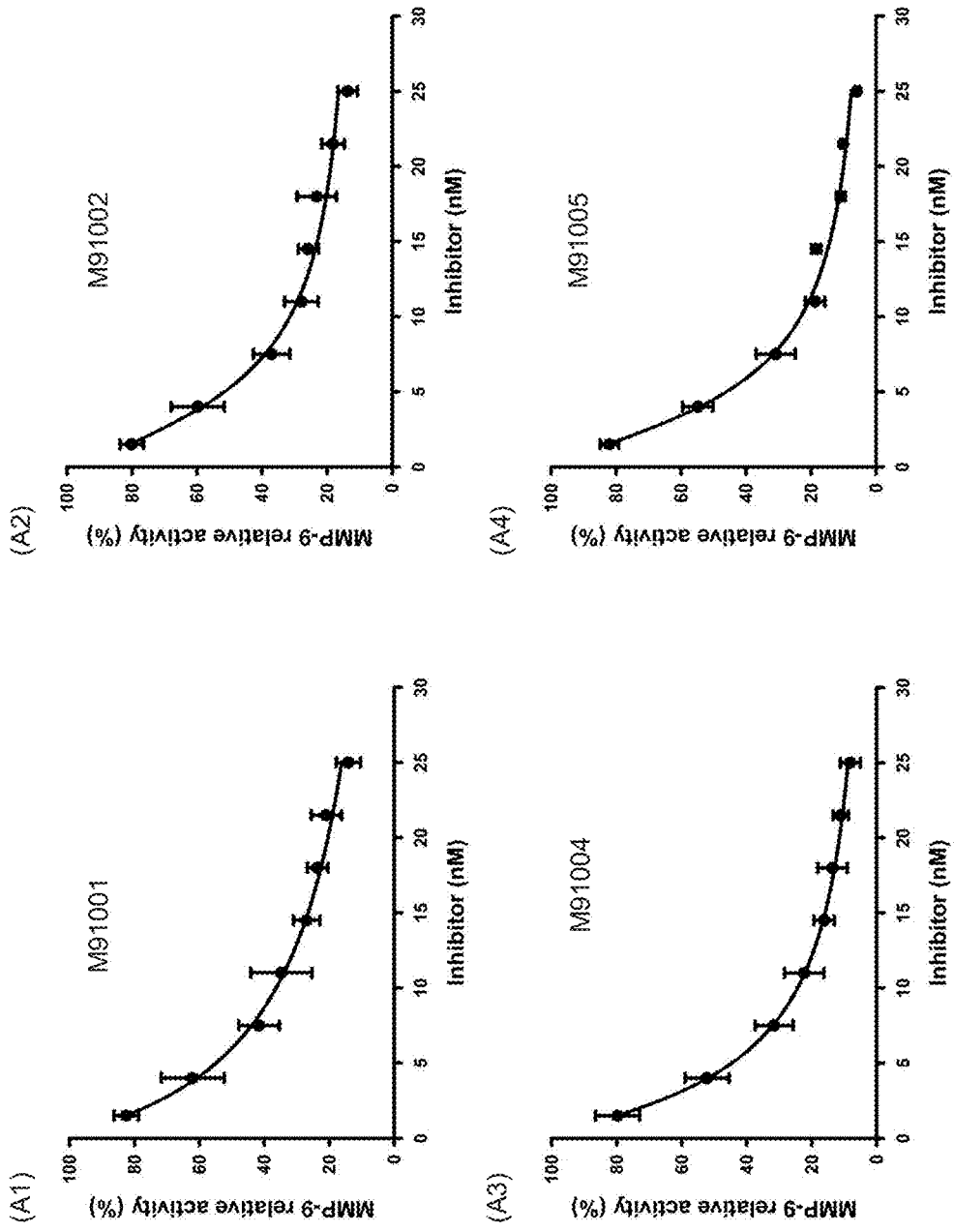

| Clone | $K_i$ (nM) |
|---|---|
| M91001 | 2.6±0.7 |
| M91002 | 2.3±0.6 |
| M91004 | 1.2±0.2 |
| M91005 | 1.4±0.2 |
| M91010 | 1.2±0.5 |
| M91011 | 1.6±0.1 |
| M91012 | 2.1±0.1 |
| M91014 | 0.45±0.11 |

| Clone | IC$_{50}$ (nM) |
|---|---|
| M91001 | 8.3±1.1 |
| M91002 | 8.5±2.1 |
| M91004 | 7.6±1.8 |
| M91005 | 8.2±1.2 |
| M91010 | 5.8±1.6 |
| M91011 | 5.0±0.5 |
| M91012 | 8.6±1.7 |
| M91014 | 3.0±0.3 |

Figure 9

| Clone  | IC$_{50}$ (nM) |
|--------|----------------|
| M91001 | 4.1±0.9        |
| M91002 | 5.1±1.1        |
| M91004 | 7.1±1.2        |
| M91005 | 8.4±0.7        |
| M91010 | 5.0±0.9        |
| M91011 | 21±3           |
| M91012 | 7.8±1.2        |
| M91014 | 9.2±0.6        |

Figure 10

| Enzyme | IC₅₀ | | | | | | | | | Remaining activity at 1 µM |
|---|---|---|---|---|---|---|---|---|---|---|
| | M91001 | M91002 | M91004 | M91005 | M91010 | M91011 | M91012 | M91014 | | sc-311438 |
| MMP-1 | >1 µM | >1 µM | >1 µM | >1 µM | >1 µM | >1 µM | >1 µM | >1 µM | | 6.8±1.8% |
| MMP-2 | >1 µM | >1 µM | >1 µM | >1 µM | >1 µM | >1 µM | >1 µM | >1 µM | | 0% |
| MMP-3 | >1 µM | >1 µM | >1 µM | >1 µM | >1 µM | >1 µM | >1 µM | >1 µM | | 1.6±1.5% |
| MMP-7 | >1 µM | >1 µM | >1 µM | >1 µM | >1 µM | >1 µM | >1 µM | >1 µM | | 45±2% |
| MMP-8 | >1 µM | >1 µM | >1 µM | >1 µM | >1 µM | >1 µM | >1 µM | >1 µM | | 0% |
| MMP-10 | >1 µM | >1 µM | >1 µM | >1 µM | >1 µM | >1 µM | >1 µM | >1 µM | | 0% |
| MMP-12 | >1 µM | >1 µM | >1 µM | >1 µM | >1 µM | >1 µM | >1 µM | >1 µM | | 0% |
| MMP-13 | >1 µM | >1 µM | >1 µM | >1 µM | >1 µM | >1 µM | >1 µM | >1 µM | | 0% |
| MMP-14 | >1 µM | >1 µM | >1 µM | >1 µM | >1 µM | >1 µM | >1 µM | >1 µM | | 0% |
| MMP-15 | >1 µM | >1 µM | >1 µM | >1 µM | >1 µM | >1 µM | >1 µM | >1 µM | | 0% |
| MMP-16 | >1 µM | >1 µM | >1 µM | >1 µM | >1 µM | >1 µM | >1 µM | >1 µM | | 3.0±0.1% |
| MMP-17 | >1 µM | >1 µM | >1 µM | >1 µM | >1 µM | >1 µM | >1 µM | >1 µM | | 0% |
| ADAM17 | >1 µM | >1 µM | >1 µM | >1 µM | >1 µM | >1 µM | >1 µM | >1 µM | | 0% |

| Clone | IC$_{50}$ (nM) |
|---|---|
| M91002 | 5.0±0.3 |
| M91002_G3 | 3.5±0.2 |
| M91002_G2 | 3.5±0.2 |
| M91002_G0 | 3.6±0.2 |

| Clone | $IC_{50}$ (nM) |
|---|---|
| M91005 | 1.1 |
| M91005-Fc-01 | 1.8 |

| Clone | IC$_{50}$ (nM) |
|---|---|
| M91005-Fc-01 | 4.5 |
| M91005_D1G-Fc-01 | 4.3 |

Figure 15 hSPINK2

DPQFGLFSKYRTPNCSQYRLPGCPRHFNPVCGSDMSTYANECTLCMKIREGGHNIKIIRNGPC(SEQ ID NO: 1)

DPQFGLFSKYRTPNCQRGIGPSCQMSYKPVCGSDMSTYANECTLCMKIREGGHNIKIIRNGPC(SEQ ID NO: 2)

DPQFGLFSKYRTPNCRTGRGPACQMGFQPVCGSDMSTYANECTLCMKIREGGHNIKIIRNGPC(SEQ ID NO: 3)

DPQFGLFSKYRTPNCRQRKGPSCQMAFQPVCGSDMSTYANECTLCMKIREGGHNIKIIRNGPC(SEQ ID NO: 4)

DPQFGLFSKYRTPNCRKRGGPSCQMSYNPVCGSDMSTYANECTLCMKIREGGHNIKIIRNGPC(SEQ ID NO: 5)

DPQFGLFSKYRTPNCRKVGEPACQMSFNPVCGSDMSTYANECTLCMKIREGGHNIKI
IRNGPC(SEQ ID NO: 6)

DPQFGLFSKYRTPNCMMYKYAQCSHKSQPVCGSDMSTYANECTLCMKIREGGHNIKI
IRNGPC(SEQ ID NO: 7)

DPQFGLFSKYRTPNCRVGGPSCQMSFNPVCGSDMSTYANECTLCMKIREGGHNIKI
IRNGPC(SEQ ID NO: 8)

DPQFGLFSKYRTPNCVMYKYAQCSHKYKPVCGSDMSTYANECTLCMKIREGGHNIKI
IRNGPC(SEQ ID NO: 9)

GPQFGLFSKYRTPNCQRGIGPSCQMSYKPVCGSDMSTYANECTLCMKIREGGHNIKI
IRNGPC(SEQ ID NO: 10)

GPQFGLFSKYRTPNCRTGRGPACQMGFQPVCGSDMSTYANECTLCMKIREGGHNIKI IRNGPC(SEQ ID NO: 11)

GPQFGLFSKYRTPNCRQRKGPSCQMAFQPVCGSDMSTYANECTLCMKIREGGHNIKI IRNGPC(SEQ ID NO: 12)

GPQFGLFSKYRTPNCRKRGGPSCQMSYNPVCGSDMSTYANECTLCMKIREGGHNIKI IRNGPC(SEQ ID NO: 13)

GPQFGLFSKYRTPNCRKVGEPACQMSFNPVCGSDMSTYANECTLCMKIREGGHNIKI IRNGPC(SEQ ID NO: 14)

GPQFGLFSKYRTPNCMMYKYAQCSHKSQPVCGSDMSTYANECTLCMKIREGGHNIKI IRNGPC(SEQ ID NO: 15)

GPQFGLFSKYRTPNCRVRGGPSCQMSFNPVCGSDMSTYANECTLCMKIREGGHNIKI IRNGPC(SEQ ID NO: 16)

GPQFGLFSKYRTPNCVMYKYAQCSHKYKPVCGSDMSTYANECTLCMKIREGGHNIKI IRNGPC(SEQ ID NO: 17)

[Figure 32]

$X_1$PQFGLFSKYRTPNC$X_2$$X_3$$X_4$$X_5$$X_6$$X_7$$X_8$C$X_9$$X_{10}$$X_{11}$$X_{12}$$X_{13}$PVCGSDMSTYANECTLC MKIREGGHNIKIIRNGPC(SEQ ID NO: 18)

[Figure 33]

Stag + linker 1

GSGMKETAAAKFERQHMDSPDLGTDDDDKAMADIGSANS(SEQ ID NO: 19)

[Figure 34]

Stag + linker 2

GSGMKETAAAKFERQHMDSPDLGTDDDDKAMAENLYFQG(SEQ ID NO: 20)

[Figure 35]

C-terminal 6-mer

GASAAA(SEQ ID NO: 21)

[Figure 36]

C-terminal 3-mer

GGG

[Figure 37]

C-terminal 2-mer

G4S linker

GGGGS(SEQ ID NO: 22)

[Figure 39]

hIgG1 Fc

DKTHTCPPCPAPELLGGPSVFLFPPKPKDTLMISRTPEVTCVVVDVSHEPEVKFNWY
VDGVEVHNAKTKPREEQYNSTYRVVSVLTVLHQDWLNGKEYCKVSNKALPAPIEKTI
SKAKGQPREPQVYTLPPSREEMTKNQVSLTCLVGFYPSDIAVEWESNGQPENNYKTT
PPVLDSDGSFFLYSKLTVDKSRWQQNVFSCSVMHEALHNHYTQKSLSLSPGK(SEQ
ID NO: 23)

[Figure 40]

primer 1

AAAAGAATTCTGATCCGCAGTTTGGTCTGTTTAG(SEQ ID NO: 24)

[Figure 41]

primer 2

AAAACTCGAGTTATGCGGCCGCAGACGCGCCGCACGGACC(SEQ ID NO: 25)

[Figure 42]

primer 3

TATACCGTCGACCTCTAGCTAGAGCTTGGC(SEQ ID NO: 26)

[Figure 43]

primer 4

GCTATGGCAGGGCCTGCCGCCCCGACGTTG(SEQ ID NO: 27)

[Figure 44]

hMMP-9

MSLWQPLVLVLLVLGCCFAAPRQRQSTLVLFPGDLRTNLTDRQLAEEYLYRYGYTRV
AEMRGESKSLGPALLLLQKQLSLPETGELDSATLKAMRTPRCGVPDLGRFQTFEGDL
KWHHHNITYWIQNYSEDLPRAVIDDAFARAFALWSAVTPLTFTRVYSRDADIVIQFG
VAEHGDGYPFDGKDGLLAHAFPPGPGIQGDAHFDDDELWSLGKGVVVPTRFGNADGA
ACHFPFIFEGRSYSACTTDGRSDGLPWCSTTANYDTDDRFGFCPSERLYTQDGNADG
KPCQFPFIFQGQSYSACTTDGRSDGYRWCATTANYDRDKLFGFCPTRADSTVMGGNS
AGELCVFPFTFLGKEYSTCTSEGRGDGRLWCATTSNFDSDKKWGFCPDQGYSLFLVA
AHEFGHALGLDHSSVPEALMYPMYRFTEGPPLHKDDVNGIRHLYGPRPEPEPRPPTT
TTPQPTAPPTVCPTGPPTVHPSERPTAGPTGPPSAGPTGPPTAGPSTATTVPLSPVD
DACNVNIFDAIAEIGNQLYLFKDGKYWRFSEGRGSRPQGPFLIADKWPALPRKLDSV
FEERLSKKLFFFSGRQVWVYTGASVLGPRRLDKLGLGADVAQVTGALRSGRGKMLLF
SGRRLWRFDVKAQMVDPRSASEVDRMFPGVPLDTHDVFQYREKAYFCQDRFYWRVSS
RSELNQVDQVGYVTYDILQCPED(SEQ ID NO: 28)

[Figure 45]

mMMP-9

MSPWQPLLLALLAFGCSSAAPYQRQPTFVVFPKDLKTSNLTDTQLAEAYLRYGYTR
AAQMMGEKQSLRPALLMLQKQLSLPQTGELDSQTLKAIRTPRCGVPDVGRFQTFKGL
KWDHHNITYWIQNYSEDLPRDMIDDAFARAFAVWGEVAPLTFTRVYGPEADIVIQFG
VAEHGDGYPFDGKDGLLAHAFPPGAGVQGDAHFDDDELWSLGKGVVIPTYYGNSNGA
PCHFPFTFEGRSYSACTTDGRNDGTPWCSTTADYDKDGKFGFCPSERLYTEHGNGEG
KPCVFPFIFEGRSYSACTTKGRSDGYRWCATTANYDQDKLYGFCPTRVDATVVGGNS
AGELCVFPFVFLGKQYSSCTSDGRRDGRLWCATTSNFDTDKKWGFCPDQGYSLFLVA
AHEFGHALGLDHSSVPEALMYPLYSYLEGFPLNKDDIDGIQYLYGRGSKPDPRPPAT
TTTEPQPTAPPTMCPTIPPTAYPTVGPTVGPTGAPSPGPTSSPSPGPTGAPSPGPTA
PPTAGSSEASTESLSPADNPCNVDVFDAIAEIQGALHFFKDGWYWKFLNHRGSPLQG
PFLTARTWPALPATLDSAFEDPQTKRVFFFSGRQMWVYTGKTVLGPRSLDKLGLGPE
VTHVSGLLPRRLGKALLFSKGRVWRFDLKSQKVDPQSVIRVDKEFSGVPWNSHDIFQ
YQDKAYFCHGKFFWRVSFQNEVNKVDHEVNQVDDVGYVTYDLLQCP(SEQ ID NO:
29)

[Figure 46]
MOCAc-KPLGL-A$_2$pr(Dnp)-AR-NH$_2$(SEQ ID NO: 30)

[Figure 47]
MOCAc-PLGL-A$_2$pr(Dnp)-AR-NH$_2$(SEQ ID NO: 31)

[Figure 48]
DNP-PLGMWSR(SEQ ID NO: 32)

[Figure 49]

MOCAc-RPKPVE-Nva-WR-Lys(Dnp)-NH$_2$(SEQ ID NO: 33)

[Figure 50]

DYKDDDDK(SEQ ID NO: 34)

[Figure 51]

GGGLNDIFEAQKIEWHE(SEQ ID NO: 35)

[Figure 52]

| Enzyme | IC$_{50}$ | | | | | | | | Remaining activity inhibitor cocktail |
|---|---|---|---|---|---|---|---|---|---|
| | M91001 | M91002 | M91004 | M91005 | M91010 | M91011 | M91012 | M91014 | |
| trypsin | >1 μM | >1 μM | >1 μM | >1 μM | >1 μM | >1 μM | >1 μM | >1 μM | 0% |
| chymotrypsin | >1 μM | >1 μM | >1 μM | >1 μM | >1 μM | >1 μM | >1 μM | >1 μM | 1% |
| tryptase | >1 μM | >1 μM | >1 μM | >1 μM | >1 μM | >1 μM | >1 μM | >1 μM | 0% |
| chymase | >1 μM | >1 μM | >1 μM | >1 μM | >1 μM | >1 μM | >1 μM | >1 μM | 0% |
| plasmin | >1 μM | >1 μM | >1 μM | >1 μM | >1 μM | >1 μM | >1 μM | >1 μM | 0% |
| thrombin | >1 μM | >1 μM | >1 μM | >1 μM | >1 μM | >1 μM | >1 μM | >1 μM | 0% |
| elastase | >1 μM | >1 μM | >1 μM | >1 μM | >1 μM | >1 μM | >1 μM | >1 μM | 0% |
| matriptase | >1 μM | >1 μM | >1 μM | >1 μM | >1 μM | >1 μM | >1 μM | >1 μM | 0% |
| protein C | >1 μM | >1 μM | >1 μM | >1 μM | >1 μM | >1 μM | >1 μM | >1 μM | 0% |
| tPA | >1 μM | >1 μM | >1 μM | >1 μM | >1 μM | >1 μM | >1 μM | >1 μM | 1% |
| uPA | >1 μM | >1 μM | >1 μM | >1 μM | >1 μM | >1 μM | >1 μM | >1 μM | 0% |
| plasma kallikrein | >1 μM | >1 μM | >1 μM | >1 μM | >1 μM | >1 μM | >1 μM | >1 μM | 0% |

[Figure 53(A)]
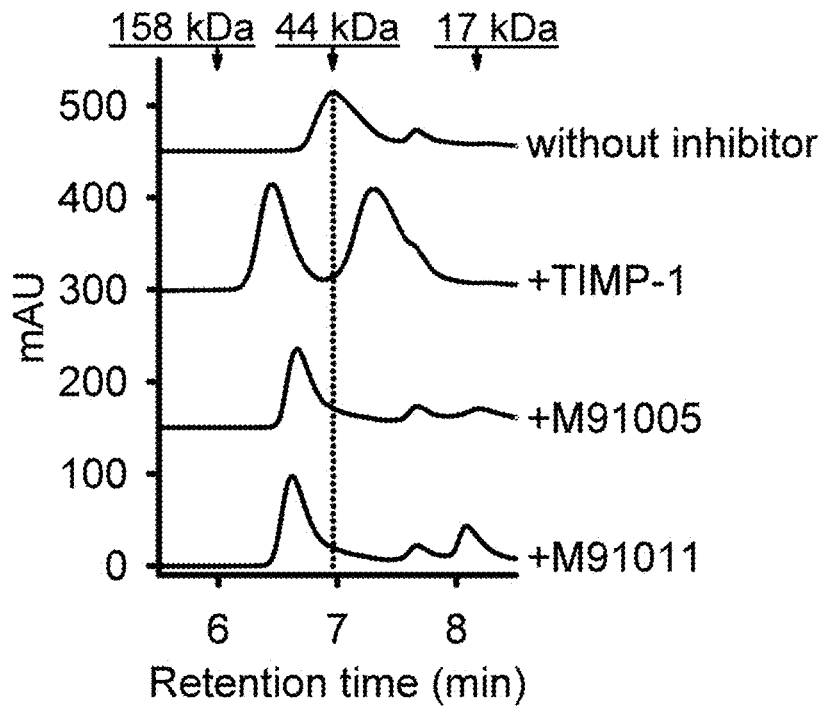
[Figure 53(B)]
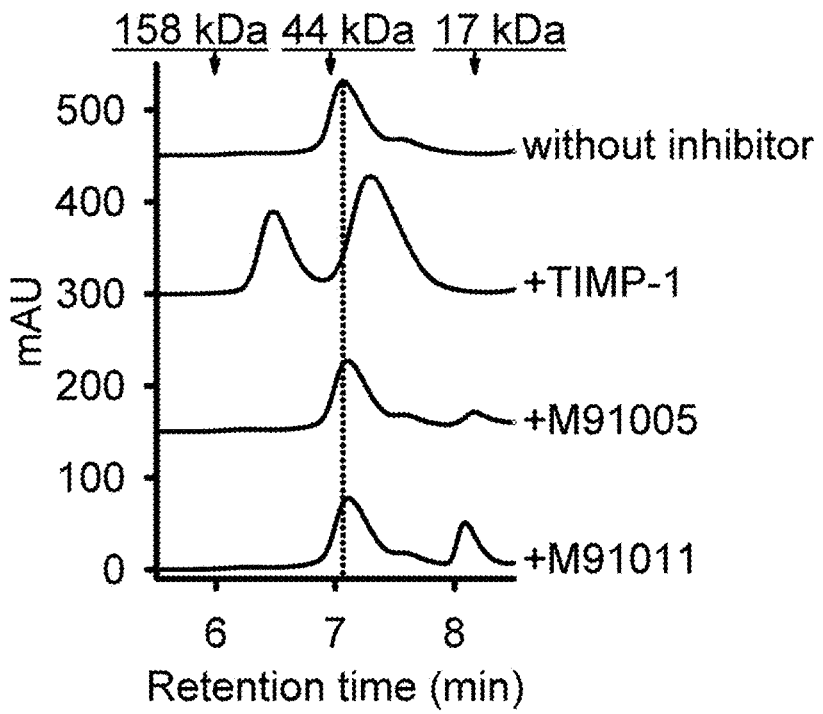

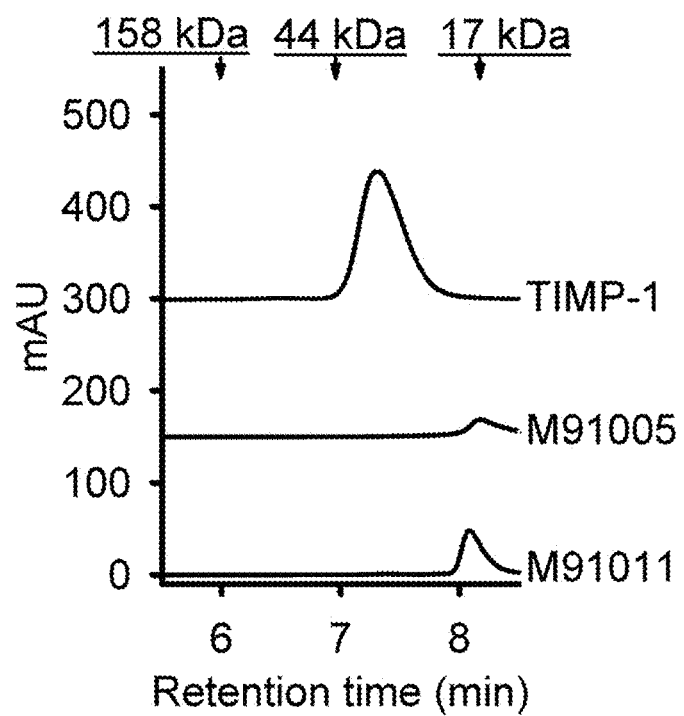
[Figure 53(C)]

[Figure 54(A)]

|  | IC$_{50}$ (nM) | | | IC$_{50}$ ratio (WT=1) | | |
| --- | --- | --- | --- | --- | --- | --- |
|  | sc-311438 | M91005 | M91011 | sc-311438 | M91005 | M91011 |
| WT | 28 ± 7 | 17 ± 7 | 17 ± 5 | 1 | 1 | 1 |
| Q108N | 29 ± 1 | 20 ± 6 | 21 ± 7 | 1.0 | 1.2 | 1.3 |
| T109F | 20 ± 3 | 15 ± 4 | 15 ± 8 | 0.7 | 0.8 | 0.9 |
| F110A | 20 ± 4 | 69 ± 12 | 7.3 ± 1.9 | 0.7 | 4.0 | 0.4 |
| E111P | 29 ± 4 | 31 ± 9 | 23 ± 9 | 1.0 | 1.8 | 1.4 |
| G112R | 29 ± 4 | 19 ± 5 | 15 ± 5 | 1.0 | 1.1 | 0.9 |
| D113K | 34 ± 7 | 21 ± 7 | 21 ± 6 | 1.2 | 1.2 | 1.3 |
| L114P | 29 ± 2 | 22 ± 6 | 19 ± 5 | 1.0 | 1.3 | 1.2 |
| Y179A | 20 ± 4 | 55 ± 13 | 81 ± 11 | 0.7 | 3.2 | 4.9 |
| P180A | 31 ± 6 | 25 ± 4 | 24 ± 9 | 1.1 | 1.4 | 1.4 |
| D185A | 22 ± 3 | 29 ± 5 | 310 ± 120 | 0.8 | 1.7 | 19.0 |
| G186A | 19 ± 1 | 15 ± 0 | 16 ± 3 | 0.7 | 0.9 | 1.0 |
| L187A | 27 ± 4 | 120 ± 10 | 20 ± 5 | 1.0 | 6.7 | 1.2 |
| F192A | 25 ± 6 | >1000 | 83 ± 20 | 0.9 | >57.8 | 5.0 |
| P193A | 27 ± 0 | 13 ± 3 | 110 ± 30 | 0.9 | 0.7 | 6.5 |
| P196T | 24 ± 4 | 18 ± 7 | 17 ± 7 | 0.9 | 1.0 | 1.0 |
| I198V | 30 ± 4 | 16 ± 4 | 16 ± 4 | 1.1 | 0.9 | 1.0 |
| Q199G | 37 ± 10 | 40 ± 16 | 22 ± 9 | 1.3 | 2.3 | 1.3 |

[Figure 54(B)]

|  | $IC_{50}$ (nM) | | | $IC_{50}$ ratio (WT=1) | | |
| --- | --- | --- | --- | --- | --- | --- |
|  | sc-311438 | M91005 | M91011 | sc-311438 | M91005 | M91011 |
| WT | 28 ± 7 | 17 ± 7 | 17 ± 5 | 1 | 1 | 1 |
| Y393A | 28 ± 2 | 48 ± 14 | >950 | 1.0 | 2.7 | >57.6 |
| L397A | 32 ± 6 | 37 ± 10 | 57 ± 16 | 1.2 | 2.2 | 3.5 |
| V398A | 44 ± 5 | 39 ± 3 | 79 ± 8 | 1.6 | 2.2 | 4.8 |
| D410E | 34 ± 9 | 22 ± 9 | 20 ± 8 | 1.2 | 1.3 | 1.2 |
| S413Q | 36 ± 12 | 30 ± 14 | 28 ± 12 | 1.3 | 1.8 | 1.7 |
| L418A | 9.2 ± 3.4 | 9.3 ± 2.9 | 5.0 ± 1.4 | 0.3 | 0.5 | 0.3 |
| Y420A | 13 ± 1 | 54 ± 8 | 33 ± 3 | 0.5 | 3.1 | 2.0 |
| P421A | 14 ± 5 | 23 ± 9 | 8.7 ± 2.0 | 0.5 | 1.3 | 0.5 |
| M422I | 40 ± 7 | 45 ± 18 | 43 ± 20 | 1.4 | 2.6 | 2.6 |
| Y423A | 24 ± 0 | 230 ± 20 | >330 | 0.9 | 13.2 | >20.0 |
| R424T | 19 ± 8 | 31 ± 20 | 45 ± 25 | 0.7 | 1.8 | 2.7 |

[Figure 55]

Boc-FSR-MCA

[Figure 56]

Suc-LLVY-MCA(SEQ ID NO: 36)

[Figure 57]

Suc-AAPF-MCA(SEQ ID NO: 37)

[Figure 58]

Boc-VLK-MCA

[Figure 59]

Boc-VPR-AMC

[Figure 60]

Suc(OMe)-Ala-Ala-Pro-Val-MCA(SEQ ID NO: 38)

[Figure 61]

Boc-QAR-AMC

[Figure 62]

Boc-LSTR-MCA(SEQ ID NO: 39)

[Figure 63]

Pyr-GR-MCA

[Figure 64]

Z-FR-MCA

[Figure 65]

DDDDK(SEQ ID NO: 40)

ACTIVE MMP9-BINDING PEPTIDE

CROSS-REFERENCE TO RELATED APPLICATIONS

This application is a national phase entry of International Application No. PCT/JP2018/026732, filed Jul. 18, 2018, which claims priority to Japanese Application No. 2017-138998, filed Jul. 18, 2017.

REFERENCE TO SEQUENCE LISTING

The sequence listing associated with this application is provided in text format in lieu of a paper copy and is hereby incorporated by reference into the specification. The name of the text file containing the sequence listing is 1660-P93USPNP Seq List 20231023 ST25. The text file is 43,863 bytes; was created on Oct. 23, 2023; and is being submitted via Patent Center.

TECHNICAL FIELD

The present invention relates to peptides, polynucleotides, vectors, cells, methods for producing peptides, peptides obtained by such methods, compositions containing the peptides, pharmaceutical compositions containing the peptides, the pharmaceutical compositions containing the peptides for treatment or prevention of various diseases, uses of the peptides for treating or preventing various diseases, methods for treating various diseases including the step of administering the peptides, compositions containing the peptides for diagnosis of or testing for various diseases, and the like.

BACKGROUND ART

Matrix metalloproteinase-9 (MMP-9) is a metalloprotease (Clan M A, family M10), and composed of an N-terminal propeptide, an enzyme active domain coordinated with a zinc ion, a fibronectin type II domain involved in binding to a substrate, and a C-terminal HPX domain (Non Patent Literature 1). MMP-9 is secreted as an inactive, precursor form of MMP-9 (pro-MMP-9), and pro-MMP-9 is then converted into an activated form of MMP-9 (active MMP-9) by cleavage of the propeptide with a protease such as MMP-3 or plasmin (Non Patent Literature 2 and 3). Active MMP-9 cleaves many extracellular matrix proteins such as type IV collagen and elastin or cytokines such as IL-1β and IL-8 as substrates, and is involved in many physiological functions such as cell proliferation, differentiation, migration, and apoptosis (Non Patent Literature 4).

It is believed that excessive enhancement of MMP-9 leads to development or aggravation of various diseases due to disruption of tissue structures and dysregulation of cell functions. In particular, it has been suggested that excessive enhancement of MMP-9 is deeply involved in pathophysiology of such diseases, for example, being involved in disruption of epithelial structure and barrier function and continuous amplification of inflammatory reaction in many inflammatory diseases such as colitis, while being involved in failure of blood-brain barrier or basement membrane and destruction of elastic fibers in vascular diseases such as cerebrovascular disorders and aortic diseases. MMP-9 inhibitors, which suppress excessively-enhanced MMP-9 activity, have been expected to be candidates for being an agent for treatment of MMP-9 related disease, and many MMP-9 inhibitors have been identified so far. Low molecular weight compounds that chelate the zinc ion coordinated to the enzyme active center of MMP-9 have potent MMP-9 inhibitory activity. However, since the amino acid sequences of the active centers of MMP family molecules have very high homology, these compounds also strongly inhibit the activities of other MMPs (Non Patent Literature 5). In clinical trials in which such non-selective MMP-9 inhibitors were administered, serious side effects were observed in the musculoskeletal system, so development of such inhibitors has been discontinued (Non Patent Literatures 6 and 7). It is difficult to obtain an MMP-9 specific inhibitor using low molecular weight inhibitors, when targeting the enzyme active center.

In accordance with advances in antibody drug creation technology, attempts have been made to use antibody molecules in order to acquire MMP-inhibiting antibodies. Furthermore, some MMP-9 inhibiting antibodies have been reported. However, antibodies which bind to the enzyme active center, while exhibiting potent MMP-9 inhibitory activity, also exhibit MMP-2 and MMP-14 inhibitory activities, thus they cannot specifically inhibit MMP-9 (Patent Literature 1, 2, and 3, and Non Patent Literature 8). Furthermore, the antibodies which bind to a region of low amino acid sequence homology between MMP family molecules, while having potent and MMP-9-specific inhibitory activity, bind not only to active MMP-9 but also inactive, pro-MMP-9, thus they cannot specifically bind to active MMP-9 (Patent Literature 4, 5, and 6, and Non Patent Literature 9 and 10). There are also reports of antibodies which do not bind to pro-MMP-9, but which do specifically bind to active MMP-9 and specifically inhibit MMP-9 activity (Patent Literature 7 and 8, and Non Patent Literature 11). However, other than antibodies or fragments thereof, low molecular weight proteins (for example, proteins or peptides not containing an immunoglobulin variable region) which do not bind to pro-MMP-9, but which do specifically bind to active MMP-9 and inhibit MMP-9 activity have been unknown.

SPINK2 (Serine Protease Inhibitor Kazal-type 2) is a Kazal-like domain having three disulfide bonds, and functions as a trypsin/acrosin inhibitor (Non Patent Literature 12). No relationship between SPINK2 and active MMP-9-binding activity has been elucidated.

CITATION LIST

Patent Literature

Patent Literature 1: WO2004/087042
Patent Literature 2: WO2008/102359
Patent Literature 3: WO2011/092700
Patent Literature 4: WO2012/027721
Patent Literature 5: WO2013/130078
Patent Literature 6: WO2013/130905
Patent Literature 7: WO2016/023972
Patent Literature 8: WO2016/023979

Non Patent Literature

Non Patent Literature 1: Nagase H, et al. (1999), Journal of Biological Chemistry (J Biol Chem.), Vol. 274, No. 31: pp. 21491-4
Non Patent Literature 2: Ogata Y, et al. (1992), Journal of Biological Chemistry (J Biol Chem.), Vol. 267, No. 6: pp. 3581-4
Non Patent Literature 3: Lijnen H R, et al. (1998), Blood, Vol. 91, No. 6: pp. 2045-53

Non Patent Literature 4: Vandooren J, et al. (2013), Critical Reviews in Biochemistry and Molecular Biology (Crit Rev Biochem Mol Biol.), Vol. 48, No. 3: pp. 222-72

Non Patent Literature 5: Cheng M, et al. (2000), Journal of Medicinal Chemistry (J Med Chem.), Vol. 43, No. 3: pp. 369-80

Non Patent Literature 6: Coussens L M, et al. (2002), Science, Vol. 295, No. 5564: pp. 2387-92

Non Patent Literature 7: Bissett D, et al. (2005), Journal of Clinical Oncology (J Clin Oncol.), Vol. 23, No. 4: pp. 842-9

Non Patent Literature 8: Sela-Passwell N, et al. (2011), Nature Medicine (Nat Med.), Vol. 18, No. 1: pp. 143-7

Non Patent Literature 9: Marshall D C, et al. (2015), PLoS One, Vol. 10, No. 5: e0127063

Non Patent Literature 10: Appleby T C, et al. (2017), Journal of Biological Chemistry (J Biol Chem.), Vol. 292, No. 16: pp. 6810-20

Non Patent Literature 11: Goffin L, et al. (2016), Inflammatory Bowel Disease (Inflamm Bowel Dis.), Vol. 22, No. 9: pp. 2041-57

Non Patent Literature 12: Chen T et al. (2009), Proteins, Vol. 77, No. 1: pp. 209-19

SUMMARY OF INVENTION

Technical Problem

An object of the present invention is to provide a novel active matrix metalloproteinase-9 (MMP-9) binding peptide.

Solution to Problem

The present invention mainly relates to the following.

(1) A SPINK2 mutant peptide which comprises an amino acid sequence represented by SEQ ID NO: 18 (FIG. 32), and binds to active human MMP-9 but does not bind to pro human MMP-9.

(2) The SPINK2 mutant peptide according to (1), wherein the peptide binds to an enzyme active domain of the active human MMP-9.

(3) The peptide according to (1) or (2), wherein the peptide inhibits protease activity of human MMP-9.

(4) The peptide according to (3), wherein the inhibition is specific to MMP-9.

(5) The peptide according to any one of (1) to (4), wherein $X_1$ is Asp or Gly.

(6) The peptide according to any one of (1) to (5), wherein $X_7$ is Pro, $X_9$ is Gln, and $X_{10}$ is Met.

(7) The peptide according to (6), wherein $X_2$ is Arg, Gln, Gly, Trp or Tyr; $X_3$ is Arg, Asp, Gln, Glu, Lys, Met, Ser, Thr or Val; $X_4$ is Ala, Arg, Asn, Asp, Gln, Gly, Leu, Lys or Val; $X_5$ is Ala, Arg, Asn, Gly, Ile, Leu or Lys; $X_6$ is Ala, Glu, Gly, Met or Ser; $X_8$ is Ala, Leu or Ser; $X_{11}$ is Ala, Gly or Ser; $X_{12}$ is Leu, Phe, Ser or Tyr; and $X_{13}$ is Asn, Asp, Gln, Leu or Lys.

(8) The peptide according to (7), wherein $X_2$ is Arg or Gln; $X_3$ is Arg, Gln, Lys, Thr or Val; $X_4$ is Arg, Gly or Val; $X_5$ is Arg, Gly, Ile or Lys; $X_6$ is Glu or Gly; $X_8$ is Ala or Ser; $X_{11}$ is Ala, Gly or Ser; $X_{12}$ is Phe or Tyr; and $X_{13}$ is Asn, Gln or Lys.

(9) The peptide according to (8), wherein the peptide comprises an amino acid sequence represented by any one of SEQ ID NOs: 2 to 6 and 8 (FIGS. 16 to 20 and 22).

(10) The peptide according to any one of (1) to (5), wherein $X_6$ is Tyr, $X_8$ is Gln, and $X_9$ is Ser.

(11) The peptide according to (10), wherein $X_2$ is Arg, Lys, Met or Val; $X_3$ is Arg, Gln, Lys or Met; $X_4$ is Phe or Tyr; $X_5$ is Gln, Glu or Lys; $X_7$ is Ala or Gly; $X_{10}$ is Asn or His; $X_{11}$ is Leu, Lys, Met or Val; $X_{12}$ is Phe, Ser or Tyr; and $X_{13}$ is Ala, Asn, Gln or Lys.

(12) The peptide according to (11), wherein $X_2$ is Met or Val; $X_3$ is Met; $X_4$ is Tyr; $X_5$ is Lys; $X_7$ is Ala; $X_{10}$ is His; $X_{11}$ is Lys; $X_{12}$ is Ser or Tyr; and $X_{13}$ is Gln or Lys.

(13) The peptide according to (12), wherein the peptide comprises an amino acid sequence represented by SEQ ID NO: 7 (FIG. 21) or SEQ ID NO: 9 (FIG. 23).

(14) The peptide according to any one of (1) to (13), wherein the peptide comprises an amino acid sequence having:

the amino acid sequence represented by SEQ ID NO: 18 (FIG. 32); and 1 to 3 amino acid residues, or an amino acid sequence represented by SEQ ID NO: 19 (FIG. 33) or SEQ ID NO: 20 (FIG. 34), added to the amino terminal side of the amino acid sequence represented by SEQ ID NO: 18 (FIG. 32).

(15) The peptide according to any one of (1) to (14), wherein the peptide comprises an amino acid sequence having:

the amino acid sequence represented by SEQ ID NO: 18 (FIG. 32); and an amino acid sequence consisting of 1 to 6 amino acids added to the carboxyl terminal side of the amino acid sequence represented by SEQ ID NO: 18 (FIG. 32).

(16) The peptide according to any one of (1) to (15), wherein the peptide comprises an amino acid sequence represented by any one of SEQ ID NOs: 2 to 17 (FIGS. 16 to 31).

(17) The peptide according to any one of (1) to (16), wherein the peptide has a conformation characterized by having three disulfide bonds and including a loop structure, an α-helix, and a β-sheet.

(18) A polynucleotide comprising a nucleotide sequence encoding an amino acid sequence contained in the peptide according to any one of (1) to (17).

(19) A vector comprising the polynucleotide according to (18).

(20) A cell which comprises the polynucleotide according to (18) or the vector according to (19), or produces the peptide according to any one of (1) to (17).

(21) A method for producing a SPINK2 mutant peptide, comprising the following steps (i) and (ii):

(i) culturing the cell according to (20); and (ii) recovering the SPINK2 mutant peptide from the culture.

(22) A method for producing the peptide according to any one of (1) to (17), comprising a step of preparing the peptide by chemical synthesis or in vitro translation.

(23) A SPINK2 mutant peptide obtained by the method according to (21) or (22).

(24) A conjugate comprising the peptide according to any one of (1) to (17) and (23), and another moiety bound thereto.

(25) The conjugate according to (24), wherein the conjugate is a peptide.

(26) The conjugate according to (24) or (25), wherein the conjugate comprises an immunoglobulin Fc region or a functional fragment thereof.

(27) A method for producing the SPINK2 mutant peptide conjugate according to any one of (24) to (26), comprising the following steps (i) and (ii):

(i) culturing a cell containing a polynucleotide having a nucleotide sequence encoding an amino acid sequence contained in the conjugate or a vector into which the polynucleotide has been inserted; and (ii) recovering the SPINK2 mutant peptide conjugate or a peptide contained in the conjugate from the culture.

(28) A method for producing the SPINK2 mutant peptide conjugate according to any one of (24) to (26), comprising, a step of preparing the conjugate or a peptide contained in the conjugate by chemical synthesis or in vitro translation.

(29) A conjugate produced by the method according to (27) or (28).

(30) An antibody or a functional fragment thereof which binds to the peptide according to any one of (1) to (17) and (23).

(31) A composition comprising the peptide according to any one of (1) to (17) and (23), the polynucleotide according to (18), the vector according to (19), the cell according to (20), the conjugate according to any one of (24) to (26) and (29), and/or the antibody according to (30) or a functional fragment thereof.

(32) A composition for test or diagnosis, comprising the peptide according to any one of (1) to (17) and (23) and/or the conjugate according to any one of (24) to (26) and (29).

(33) A method for detecting active MMP-9, comprising the following steps (i) and (ii):

(i) contacting the peptide according to any one of (1) to (17) and (23) and/or the conjugate according to any one of (24) to (26) and (29) with a test sample; and (ii) measuring the SPINK2 mutant peptide and/or the conjugate bound to a component in the test sample.

(34) The method according to (33), wherein step (ii) is a step of recovering the SPINK2 mutant peptide and/or the conjugate contacted with the test sample, and measuring the amount or the activity of active MMP-9 bound to the SPINK2 mutant peptide and/or the conjugate.

(35) A pharmaceutical composition comprising the peptide according to any one of (1) to (17) and (23), the polynucleotide according to (18), the vector according to (19), the cell according to (20), and/or the conjugate according to any one of (24) to (26) and (29).

(36) The pharmaceutical composition according to (35), for treatment or prevention of an MMP-9 related disease.

(37) The pharmaceutical composition according to (36), wherein the MMP-9 related disease is an inflammatory/autoimmune disease, a neurodegenerative disease, a mental disease, a vascular disease, or a malignant tumor.

(38) The pharmaceutical composition according to (37), wherein the inflammatory/autoimmune disease is rheumatoid arthritis, systemic lupus erythematosus, scleroderma, bronchial asthma, interstitial pneumonia, chronic obstructive pulmonary disease, ulcerative colitis, Crohn's disease, hepatitis, eczema (or dermatitis), psoriasis, lichen planus, erythema/erythroderma, hives, alopecia, pemphigus, acne vulgaris, pressure ulcer/wound, conjunctivitis, keratitis, rhinitis, stomatitis, glossitis, Behcet's disease, multiple sclerosis, encephalitis, headache, peripheral neuritis, diabetic complications (diabetic retinopathy, diabetic nephropathy, diabetic neuropathy), atherosclerosis, pancreatitis, chronic heart failure, or nephritis.

(39) The pharmaceutical composition according to (37), wherein the neurodegenerative disease is Alzheimer's disease, Parkinson's disease, Huntington's disease, amyotrophic lateral sclerosis, frontotemporal dementia, brain injury, spinal cord injury, hypoxia, convulsion, or traumatic brain disorder.

(40) The pharmaceutical composition according to (37), wherein the mental disease is major depression, bipolar disorder, anxiety, post-traumatic stress disorder (PTSD), eating disorder, sleep disorder, schizophrenia, addiction, autism, fragile X syndrome, attention deficit hyperactivity disorder, or Down syndrome.

(41) The pharmaceutical composition according to (37), wherein the vascular disease is cerebrovascular disorder, cerebral aneurysm, cerebral amyloid angiopathy, peripheral vascular disorder, aortic aneurysm, aortic dissection, arteriovenous fistula, arteriosclerosis, Takayasu arteritis, Kawasaki disease, varicose vein, or vascular calcification.

(42) The pharmaceutical composition according to (37), wherein the malignant tumor is lung cancer, breast cancer, pancreatic cancer, colorectal cancer, or glioma.

(43) A composition for test or diagnosis, comprising the antibody according to (30) or a functional fragment thereof.

(44) The method according to (21), (22), (27) or (28), comprising an affinity purification step using the antibody according to (30) or a functional fragment thereof.

(45) A method for identifying a human MMP-9 inhibitory SPINK2 mutant peptide, comprising the following steps (i) to (iii):

(i) incubating a human MMP-9 protease and a substrate in the presence and absence of a SPINK2 mutant peptide to be tested;

(ii) measuring human MMP-9 protease activities in the presence and absence of the SPINK2 mutant peptide to be tested; and (iii) comparing the human MMP-9 protease activity in the presence of the SPINK2 mutant peptide with the human MMP-9 protease activity in the absence of the SPINK2 mutant peptide, and determining that the SPINK2 mutant peptide is positive, when the human MMP-9 protease activity in the presence of the SPINK2 mutant peptide is smaller than the human MMP-9 protease activity in the absence of the SPINK2 mutant peptide.

(46) A method for identifying a human MMP-9 specific inhibitory compound, comprising the following steps (i) to (iii):

(i) causing a test compound to bind to human active MMP-9 in the presence of a peptide having an amino acid sequence represented by any one of SEQ ID NOs: 2 to 17 (FIGS. 16 to 31);

(ii) determining whether the compound competes with the peptide for binding to the human active MMP-9; and (iii) determining whether the compound has human MMP-9 specific binding activity.

(47) The method according to (46), wherein the compound is a SPINK2 mutant peptide.

(48) The method according to (46), wherein the compound is an antibody or an antigen-binding protein.

(49) The method according to (45), (47) or (48), further comprising a step of preparing the peptide, the antibody or the antigen-binding protein by chemical synthesis, in vitro translation, or recombination.

Advantageous Effects of Invention

The peptide provided by the present invention or a pharmaceutical composition containing the peptide has active MMP-9-binding activity, and thus is useful for treatment or prevention of MMP-9 related disease, detection of active MMP-9, and the like.

BRIEF DESCRIPTION OF THE DRAWINGS

FIG. 1(A) is a chart showing a comparison of sequence similarity of human/monkey/rat/mouse MMP-9 (SEQ ID NO:28/ SEQ ID NO:41/SEQ ID NO:42/SEQ ID NO:29, respectively). The dashed line denotes a propeptide (human MMP-9: Ala20 to Arg106). The solid line denotes an enzyme active domain (human MMP-9: Phe107 to Pro449) containing fibronectin type II domains (human MMP-9: Ala225 to Ser273, Ala283 to Thr331, Ser342 to Asp390).

FIG. 1(B) is a chart showing the comparison of sequence similarity of human/monkey/rat/mouse MMP-9 (SEQ ID NO:28/ SEQ ID NO:41/SEQ ID NO:42/SEQ ID NO:29, respectively) (continued).

FIG. 1(C) is a chart showing the comparison of sequence similarity of human/monkey/rat/mouse MMP-9 (SEQ ID NO:28/ SEQ ID NO:41/SEQ ID NO:42/SEQ ID NO:29, respectively) (continued).

FIG. 3 is a table showing active human MMP-9-binding activity $EC_{50}$ of active MMP-9-binding peptides (n=2).

FIG. 9 is a table showing mouse MMP-9 inhibitory activity $IC_{50}$ of active MMP-9-binding peptides (n=3, Mean±SD) when the substrate peptide was used.

FIG. 10 is a table showing the inhibitory activity $IC_{50}$ for each MMP or for ADAM17 of active MMP-9-binding peptides (n=3, Mean±SD), using the degradation rate of the substrate peptide as an index.

FIG. 15 shows an amino acid sequence of human SPINK2 (SEQ ID NO: 1).

FIG. 16 shows an amino acid sequence of peptide M91001 (SEQ ID NO: 2).

FIG. 17 shows an amino acid sequence of peptide M91002 (SEQ ID NO: 3).

FIG. 18 shows an amino acid sequence of peptide M91004 (SEQ ID NO: 4).

FIG. 19 shows an amino acid sequence of peptide M91005 (SEQ ID NO: 5).

FIG. 20 shows an amino acid sequence of peptide M91010 (SEQ ID NO: 6).

FIG. 21 shows an amino acid sequence of peptide M91011 (SEQ ID NO: 7).

FIG. 22 shows an amino acid sequence of peptide M91012 (SEQ ID NO: 8).

FIG. 23 shows an amino acid sequence of peptide M91014 (SEQ ID NO: 9).

FIG. 24 shows an amino acid sequence of a peptide derivative M91001_D1G (SEQ ID NO: 10).

FIG. 25 shows an amino acid sequence of a peptide derivative M91002_D1G (SEQ ID NO: 11).

FIG. 26 shows an amino acid sequence of a peptide derivative M91004_D1G (SEQ ID NO: 12).

FIG. 27 shows an amino acid sequence of a peptide derivative M91005_D1G (SEQ ID NO: 13).

FIG. 28 shows an amino acid sequence of a peptide derivative M91010_D1G (SEQ ID NO: 14).

FIG. 29 shows an amino acid sequence of a peptide derivative M91011_D1G (SEQ ID NO: 15).

FIG. 30 shows an amino acid sequence of a peptide derivative M91012_D1G (SEQ ID NO: 16).

FIG. 31 shows an amino acid sequence of a peptide derivative M91014_D1G (SEQ ID NO: 17).

FIG. 32 shows a general formula of active MMP-9-binding peptide (SEQ ID NO: 18), in which $X_1$ to $X_{13}$ denote any amino acid.

FIG. 33 shows an amino acid sequence consisting of Stag+linker 1 (SEQ ID NO: 19).

FIG. 34 shows an amino acid sequence consisting of Stag+linker 2 (SEQ ID NO: 20).

FIG. 35 shows an amino acid sequence of a C-terminal 6-mer (SEQ ID NO: 21).

FIG. 36 shows an amino acid sequence of a C-terminal 3-mer Gly-Gly-Gly.

FIG. 37 shows an amino acid sequence of a C-terminal 2-mer Gly-Gly.

FIG. 38 shows an amino acid sequence of a G4S linker (SEQ ID NO: 22).

FIG. 39 shows an amino acid sequence of a human immunoglobulin G1 Fc region (SEQ ID NO: 23).

FIG. 40 shows a nucleotide sequence of primer 1 (SEQ ID NO: 24).

FIG. 41 shows a nucleotide sequence of primer 2 (SEQ ID NO: 25).

FIG. 42 shows a nucleotide sequence of primer 3 (SEQ ID NO: 26).

FIG. 43 shows a nucleotide sequence of primer 4 (SEQ ID NO: 27).

FIG. 44 shows an amino acid sequence of human MMP-9 (SEQ ID NO: 28).

FIG. 45 shows an amino acid sequence of mouse MMP-9 (SEQ ID NO: 29).

FIG. 46 shows an amino acid sequence of MOCAc—KPLGL-A$_2$pr (Dnp)-AR—NH$_2$ (SEQ ID NO: 30). The "MOCAc—K" at the N-terminal means (7-methoxycoumarin-4-yl)acetyl-L-lysine, the "A$_2$pr(Dnp)-A" means [Nβ-(2,4-dinitrophenyl)-L-2,3-diaminopropionyl]-L-alanine, and the "R—NH$_2$" at the C-terminal means L-arginine amide, respectively.

FIG. 47 shows an amino acid sequence of MOCAc—PLGL-A$_2$pr(Dnp)-AR—NH$_2$ (SEQ ID NO: 31). The "MOCAc—P" at the N-terminal means (7-methoxycoumarin-4-yl)acetyl-L-proline, "A$_2$pr(Dnp)-A" means [Nβ-(2,4-dinitrophenyl)-L-2,3-diaminopropionyl]-L-alanine, and the C-terminal "R—NH$_2$" means L-arginine amide, respectively.

FIG. 48 shows an amino acid sequence of DNP—PLGMWSR (SEQ ID NO: 32). The "DNP—P" at the N-terminal means N-(2,4-Dinitrophenyl)-L-proline.

FIG. 49 shows an amino acid sequence of MOCAc—RPKPVE-Nva-WR-Lys(Dnp)-NH$_2$ (SEQ ID NO: 33). The "MOCAc-R" at the N-terminal means (7-methoxycoumarin-4-yl) acetyl-L-arginine, "Nva" means L-norvaline, and "Lys (Dnp)-NH$_2$" means [Nε-(2,4-dinitrophenyl)]-L-lysine amide, respectively.

FIG. 50 shows an amino acid sequence of a FLAG tag (SEQ ID NO: 34).

FIG. 51 shows an amino acid sequence of an Avi tag (SEQ ID NO: 35).

FIG. 52 is a table showing serine protease inhibitory activity IC$_{50}$ of active MMP-9-binding peptides (n=1), using the degradation rate of the substrate peptide as an index.

FIG. 53(A) is a graph showing an evaluation of whether active MMP-9-binding peptide binds to active human MMP-9, by size exclusion chromatography. In the absence of the inhibitor, a peak of the active human MMP-9 enzyme active domain was detected at a retention time of 7.0 minutes (dotted line). In the presence of TIMP-1 or active MMP-9-binding peptides M91005 and M91011, the retention time of the peak of the active human MMP-9 enzyme active domain was shifted to the high molecular weight side.

FIG. 53(B) is a graph showing an evaluation of whether active MMP-9-binding peptide does not bind to the human MMP-9 E402Q mutant, by size exclusion chromatography. In the absence of inhibitor, the peak of human MMP-9 enzyme active domain E402Q mutant was detected at a retention time of 7.1 minutes (dotted line). In the presence of TIMP-1, the retention time of the peak of human MMP-9 enzyme active domain E402Q mutant was shifted to the high molecular weight side. In contrast, the retention time of the peak of human MMP-9 enzyme active domain E402Q mutant did not change in the presence of the active MMP-9-binding peptide M91005 or M91011.

FIG. 53(C) is a graph showing an evaluation of TIMP-1 and the active MMP-9-binding peptides M91005 and M91011, by size exclusion chromatography.

FIG. 54(A) is a table showing human MMP-9 mutant inhibitory activity IC$_{50}$ of active MMP-9-binding peptides (n=3, Mean±SD) when the substrate peptide was used, and the relative values of IC$_{50}$ when the wild type human MMP-9 IC$_{50}$ was taken as 1.

FIG. 54(B) is a table showing human MMP-9 mutant inhibitory activities IC$_{50}$ of active MMP-9-binding peptides (n=3, Mean±SD) when the substrate peptide was used, and the relative values of IC$_{50}$ when the wild type human MMP-9 IC$_{50}$ was taken as 1 (continued).

FIG. 55 shows an amino acid sequence of Boc-FSR-MCA. The "Boc" at the N-terminal means t-Butyloxycarbonyl, and the "MCA" at the C-terminal means 4-methylcoumalyl-7-amide.

FIG. 56 shows an amino acid sequence of Suc-LLVY-MCA (SEQ ID NO: 36). The "Suc" at the N-terminal means succinyl, and the "MCA" at the C-terminal means 4-methylcoumaryl-7-amide.

FIG. 57 shows an amino acid sequence of Suc-AAPF-MCA (SEQ ID NO: 37). The "Suc" at the N-terminal means succinyl, and the "MCA" at the C-terminal means 4-methylcoumaryl-7-amide.

FIG. 58 shows an amino acid sequence of Boc-VLK-MCA. The "Boc" at the N-terminal means t-Butyloxycarbonyl, and the "MCA" at the C-terminal means 4-methylcoumaryl-7-amide.

FIG. 59 shows an amino acid sequence of Boc-VPR-AMC. The "Boc" at the N-terminal means t-Butyloxycarbonyl, and the "AMC" at the C-terminal means 7-Amino-4-methylcoumarin.

FIG. 60 shows an amino acid sequence of Suc(OMe)-Ala-Ala-Pro-Val-MCA (SEQ ID NO: 38). The "Suc(OMe)"

Figure 2A:
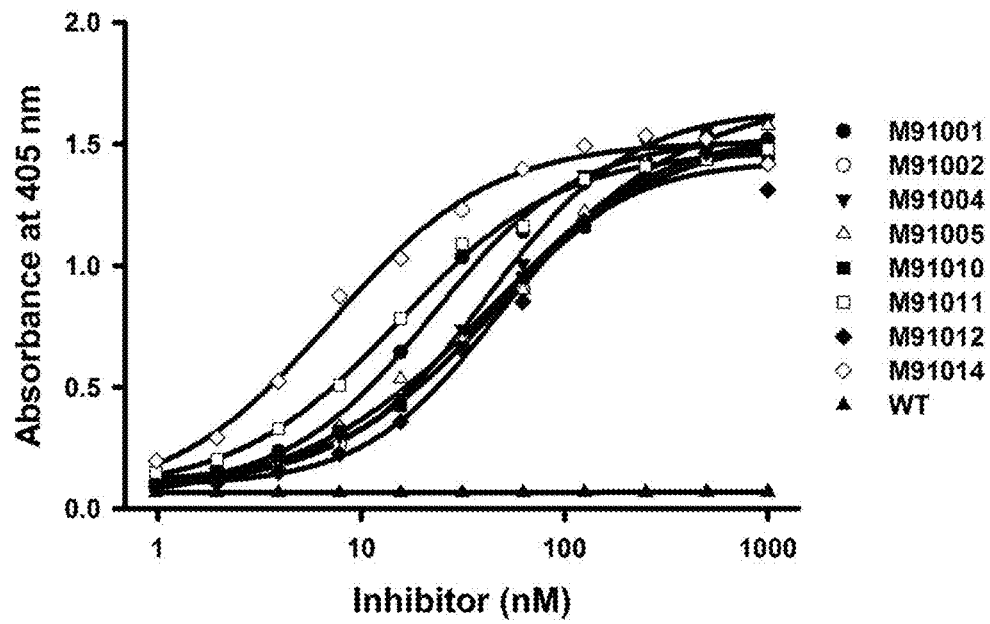
FIG. 2(A) is a graph showing an evaluation of active human MMP-9-binding activity of each binding peptide or wild type SPINK2 (n=2), using the detection intensity of the tag added to the amino terminal of the active MMP-9-binding peptide as an index.

at the N-terminal means N-Methoxysuccinyl, and the "MCA" at the C-terminal means 4-methylcoumaryl-7-amide.

FIG. 61 shows an amino acid sequence of Boc-QAR-AMC. The "Boc" at the N-terminal means t-Butyloxycarbonyl, and the "AMC" at the C-terminal means 7-Amino-4-methylcoumarin.

FIG. 62 shows an amino acid sequence of Boc-LSTR-MCA (SEQ ID NO: 39). The "Boc" at the N-terminal means t-Butyloxycarbonyl, and the "MCA" at the C-terminal means 4-methylcoumaryl-7-amide.

FIG. 63 shows an amino acid sequence of Pyr-GR-MCA. The "Pyr" at the N-terminal means L-pyroglutamyl, and the "MCA" at the C-terminal means 4-methylcoumaryl-7-amide.

Figures 64, 65:
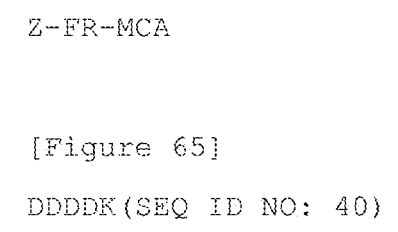

FIG. 64 shows an amino acid sequence of Z—FR-MCA. The "Z" at the N-terminal means Benzyloxycarbonyl, and the "MCA" at the C-terminal means 4-methylcoumaryl-7-amide.

FIG. 65 shows an amino acid sequence of an enterokinase recognition sequence (SEQ ID NO: 40).

In the present invention, when a sequence is described with SEQ ID NO: X along with Figure Y, such as "SEQ ID NO: X (Figure Y)" or "Figure Y (SEQ ID NO: X)", it means that the sequence is represented by SEQ ID NO: X or Figure Y.

In addition, when the amino acid (X), the number (one to several digits) and the other amino acid (Y) are denoted such as XnY, XnnY, XnnnY or the like, it means that amino acid X at the n-th, nn-th, or nnn-th (position at one digit, two digit, or three digit numbers, respectively) is replaced with another amino acid Y. For example, Arg344Lys means that the 344th amino acid is replaced from Arg to Lys.

DESCRIPTION OF EMBODIMENTS

1. Definitions

In the present invention, the term "gene" means a nucleic acid molecule containing a nucleotide sequence encoding an amino acid sequence contained in a protein or a complementary strand thereof. The nucleic acid molecule consists of one strand, two strands, or three or more strands, and the "gene" includes a complex of a DNA strand and an RNA strand, a mixture of ribonucleotides and deoxyribonucleotides present on one strand, and a nucleic acid molecule composed of two or three or more strands each containing such a strand.

In the present invention, the terms "gene", "polynucleotide" and "nucleic acid molecule" have the same meaning, and the number of their constituent units, which are ribonucleotides, deoxyribonucleotides, nucleotides, nucleosides and the like, has no limitation. For example, DNA, RNA, mRNA, cDNA, cRNA, probes, oligonucleotides, primers and the like are included in the scope of the "gene", "polynucleotide" and "nucleic acid molecule". The "nucleic acid molecule" is sometimes abbreviated as "nucleic acid".

In the present invention, the terms "polypeptide", "peptide" and "protein" have the same meanings.

In the present invention, a peptide that recognizes or binds to a target molecule X (hereinafter, such recognition or binding action is collectively referred to as "X binding activity") can be referred to as an "X binding peptide". Furthermore, a peptide that recognizes or binds to the target molecule X, and inhibits or suppresses one or two or more activities or functions of the target molecule X (hereinafter, the action of inhibition or suppression will be collectively referred to as "X inhibitory activity") can be referred to as an "X inhibitory peptide".

In the present invention, the term "SPINK2" means Serine Protease Inhibitor Kazal-type 2, and is a 7 kDa protein composed of a Kazal-like domain having three disulfide bonds. It is preferred that SPINK2 is derived from humans. In the present invention, human SPINK2 is simply referred to as "SPINK2", unless otherwise specified.

In the present invention, the term "MMP-9" means matrix metalloproteinase-9. MMP-9 is a protein belonging to the MMP family, and composed of a secretory signal peptide, a propeptide, an enzyme active domain coordinated with a zinc ion, a fibronectin type II domain involved in binding to a substrate, and a C-terminal HPX domain. It is preferred that MMP-9 is derived from humans. In the present invention, human MMP-9 is sometimes simply referred to as "MMP-9", unless otherwise specified.

In the present invention, the term "pro-MMP-9" means pro-matrix metalloproteinase-9. pro-MMP-9 is composed of a propeptide, an enzyme active domain coordinated with a zinc ion, a fibronectin type II domain involved in binding to a substrate, and a C-terminal HPX domain. It is preferred that pro-MMP-9 is derived from humans. In the present invention, human precursor MMP-9 is simply referred to as "pro-MMP-9" unless otherwise specified, but sometimes is also referred to as "full-length mature MMP-9" or "hMMP-9(full)".

In the present invention, the term "active MMP-9" means active matrix metalloproteinase-9. Active MMP-9 is composed of an enzyme active domain coordinating a zinc ion, a fibronectin type II domain involved in binding to a substrate, and a C-terminal HPX domain. It is preferred that active MMP-9 is derived from humans. In the present invention, the human active MMP-9 is simply referred to as "active MMP-9" unless otherwise specified, but sometimes is also referred to as "active MMP-9(full)".

In the present invention, the term "pro-MMP-9 enzyme active domain" means a pro-matrix metalloproteinase-9 catalytic domain. The pro-MMP-9 enzyme active domain contains a propeptide and an enzyme active domain coordinated with a zinc ion as essential components, and optionally contains a fibronectin type II domain involved in binding to a substrate. It is preferred that the pro-MMP-9 enzyme active domain is derived from humans. In the present invention, the pro human MMP-9 enzyme active domain is simply referred to as "pro-MMP-9 enzyme active domain" unless otherwise stated, but sometimes is also referred to as "pro-MMP-9(cat)".

In the present invention, the term "active MMP-9 enzyme active domain" means an active matrix metalloproteinase-9 catalytic domain. The active MMP-9 enzyme active domain includes an enzyme active domain coordinated with a zinc ion as an essential component, and optionally contains a fibronectin type II domain involved in binding to a substrate. It is preferred that the active MMP-9 enzyme active domain is derived from humans. In the present invention, the active human MMP-9 enzyme active domain is abbreviated as "active MMP-9 enzyme active domain" unless otherwise stated, but sometimes is also referred to as "pro-MMP-9 (cat)".

In the present invention, the term "MMP-9-binding peptide" means a peptide that recognizes or binds to a partial peptide or a partial higher-order structure of MMP-9. When the fragments of the peptide, the adducts of another moiety and the peptide, or the conjugates of the peptide maintain the MMP-9-binding activity, they are included within the scope of the term "MMP-9-binding peptide". That is, the fragments, adducts, and modified compounds of the peptide maintaining MMP-9-binding activity are also included within the term "MMP-9-binding peptide".

In the present invention, the term "active MMP-9-binding peptide" means a peptide that recognizes or binds to a partial peptide or partial higher-order structure of the active MMP-9. When the fragments of the peptide, the adducts of another moiety and the peptide, or the conjugates of the peptide maintain the active MMP-9-binding activity, they are included within the scope of the term "active MMP-9-binding peptide". That is, the fragments, adducts and modified compounds of the peptide maintaining the active MMP-9-binding activity are also included within the term "active MMP-9-binding peptide".

In the present invention, the term "MMP-9 inhibitory peptide" means a peptide that inhibits or suppresses one or two or more activities or functions of MMP-9. When the fragments of the peptide, the adducts of another moiety and the peptide, or the conjugates of the peptide maintain the MMP-9 inhibitory activity, they are included within the scope of the term "MMP-9 inhibitory peptide". That is, the fragments, adducts and modified compounds of the peptide maintaining the MMP-9 inhibitory activity are also included within the term "MMP-9 inhibitory peptide".

In the present invention, the term "cell" includes various cells derived from an individual animal, passage cultured cells, primary cultured cells, cell lines, recombinant cells, yeasts, microorganisms, and the like.

In the present invention, a "site" to which a peptide binds, i.e., a "site" recognized by the peptide, means a contiguous or intermittent partial amino acid sequence or partial higher-order structure on a target molecule which the peptide binds to or recognizes. In the present invention, such a site can be referred to as an epitope or binding site on the target molecule.

In the present invention, the term "SPINK2 mutant" means a peptide containing an amino acid sequence having, in the amino acid sequence of the wild type SPINK2, one or two or more amino acids substituted with an amino acid different from the wild type, one or two or more amino acids deleted from the wild type, one or two or more non-wild-type amino acids inserted, and/or non-wild-type amino acids added to the amino-terminal (N-terminal) and/or carboxyl-terminal (C-terminal) (hereinafter, these alterations are collectively referred to as a "mutation"). When the "SPINK2 mutant" has active MMP-9-binding activity, it is encompassed by the term "active MMP-9-binding peptide". It should be noted that, in the present invention, the term "insertion" may be included within the scope of the term "addition".

In the present invention, the term "several" in the term "one to several" refers to 3 to 10.

In the present invention, the term "hybridize under stringent conditions" means to hybridize under conditions in which hybridization is performed at 65° C. in a solution containing 5×SSC, and then washings are performed in an aqueous solution containing 2×SSC-0.1% SDS at 65° C. for 20 minutes, in an aqueous solution containing 0.5×SSC-0.1% SDS at 65° C. for 20 minutes, and in an aqueous solution containing 0.2×SSC-0.1% SDS at 65° C. for 20 minutes, respectively, or under equivalent conditions thereto. The SSC represents an aqueous solution of 150 mM NaCl-15 mM sodium citrate, and n x SSC means n-fold concentrations of SSC.

2. Peptide 2-1. Amino Acid

The term "amino acid" is an organic compound containing an amino group and a carboxyl group, and it preferably means an α-amino acid included as a constitutional unit in proteins, more preferably in naturally occurring proteins. In the present invention, more preferred amino acids are Ala, Arg, Asn, Asp, Cys, Gln, Glu, Gly, His, Ile, Leu, Lys, Met, Phe, Pro, Ser, Thr, Trp, Tyr, and Val. Unless otherwise specified, the term "amino acid" means these total 20 amino acids. The total 20 amino acids can be referred to as "naturally occurring amino acids". The active MMP-9-binding peptide of the present invention preferably contains naturally occurring amino acids.

In the present invention, the term "amino acid residue" is sometimes abbreviated as "amino acid".

In the present invention, an amino acid is an L-amino acid, a D-amino acid, or a mixture thereof (DL-amino acid), but unless otherwise specified, it means an L-amino acid.

The naturally occurring amino acids can be divided into, for example, the following groups, based on the nature of the common side chains.

(1) Hydrophobic amino acid group: Met, Ala, Val, Leu, Ile
(2) Neutral hydrophilic amino acid group: Cys, Ser, Thr, Asn, Gln
(3) Acidic amino acid group: Asp, Glu
(4) Basic amino acid group: His, Lys, Arg
(5) A group of amino acids that influence the orientation of the backbone: Gly, Pro
(6) Aromatic amino acid group: Trp, Tyr, Phe However, the classification of naturally occurring amino acids is not limited to these.

In the present invention, naturally occurring amino acids may undergo conservative amino acid substitutions.

The term "conservative amino acid substitution" means a substitution with a functionally equivalent or similar amino acid. A conservative amino acid substitution in a peptide results in a static change in the amino acid sequence of the peptide. For example, one or two or more amino acids having similar polarity act functionally equivalently, thus a conservative amino acid substitution with such amino acids results in a static change in the amino acid sequence of the peptide. In general, a substitution with an amino acid in the same group can be considered conservative as regards the structure and function. However, as will be apparent to those skilled in the art, the role played by a particular amino acid residue may be determined in the three-dimensional structure of a molecule containing the amino acid. For example, cysteine residues may take the oxidized (disulfide) form, which has less polarity compared to the reduced (thiol) form. The long aliphatic moiety of arginine side chains may constitute structurally and functionally important features. The side chain containing an aromatic ring (tryptophan, tyrosine, phenylalanine) may also contribute to an ion-aromatic interaction or cation-pi interaction. In such a case, even if an amino acid having such a side chain is substituted with an amino acid belonging to the acidic or nonpolar groups, the substitution may be structurally and functionally conservative. Residues such as proline, glycine, and cysteine (disulfide form) have the possibility of directly affecting the backbone conformation, thus they often cannot be substituted without structural distortion.

The conservative amino acid substitutions include specific substitutions based on side chain similarity as shown below (L. Lehninger, Biochemistry, $2^{nd}$ edition, pp. 73-75, Worth Publisher, New York (1975)) and typical substitutions.

(1) Nonpolar amino acid group: alanine (hereinafter referred to as "Ala" or simply "A"), valine (hereinafter referred to as "Val" or simply "V"), leucine (hereinafter referred to as "Leu" or simply "L"), isoleucine (hereinafter referred to as "Ile" or simply "I"), proline (hereinafter referred to as "Pro" or simply "P"), phenylalanine (hereinafter referred to as "Phe" or simply "F"), tryptophan (hereinafter referred to as "Trp" or simply "W"), and methionine (hereinafter referred to as "Met" or simply "M");

(2) Uncharged polar amino acid group: glycine (hereinafter referred to as "Gly" or simply "G"), serine (hereinafter referred to as "Ser" or simply "S"), threonine (hereinafter referred to as "Thr" or simply "T"), cysteine (hereinafter referred to as "Cys" or simply "C"), tyrosine (hereinafter referred to as "Tyr" or simply "Y"), asparagine (hereinafter referred to as "Asn" or simply "N"), and glutamine (hereinafter referred to as "Gln" or simply "Q");

(3) Acidic amino acid group: aspartic acid (hereinafter referred to as "Asp" or simply "D"), and glutamic acid (hereinafter referred to as "Glu" or simply "E");

(4) Basic amino acid group: lysine (hereinafter referred to as "Lys" or simply "K"), arginine (hereinafter referred to as "Arg" or simply "R"), and histidine (hereinafter referred to as "His" or simply "H").

In the present invention, the amino acid may be an amino acid other than a naturally occurring amino acid. Examples of such an amino acid include, for example, selenocysteine, N-formylmethionine, pyrrolidine, pyroglutamic acid, cystine, hydroxyproline, hydroxylysine, thyroxine, O-phosphoserine, desmosine, β-alanine, sarcosine, ornithine, creatine, γ-aminobutyric acid, opain, theanine, tricolominic acid, kainic acid, domoic acid, and achromeic acid found in naturally occurring peptides and proteins. Further examples of such amino acids include norleucine, N-terminal protected amino acids such as Ac-amino acid, Boc-amino acid, Fmoc-amino acid, Trt-amino acid, and Z-amino acid; C-terminal protected amino acids such as t-butyl ester, benzyl ester, cyclohexyl ester, and fluorenyl ester of amino acids; and other amino acids not found in the nature including diamine, ω-amino acid, β-amino acid, γ-amino acid, a Tic derivative of amino acid, and aminophosphonic acid. However, without limiting to these examples, amino acids other than the 20 "naturally occurring amino acids" described above are collectively referred to as "non-naturally occurring amino acids", for convenience, in the present invention.

2-2. Active MMP-9-Binding Peptide

The active MMP-9-binding peptide of the present invention is a SPINK2 mutant in which the backbone of SPINK2 is maintained at least partially (hereinafter, abbreviated as "SPINK2 mutant"). It recognizes or binds to active MMP-9, or a partial peptide or a partial higher-order structure thereof (hereinafter, such recognition or binding action is collectively referred to as "active MMP-9-binding activity"). It is preferred that the active MMP-9-binding peptide of the present invention does not bind to pro-MMP-9. In other words, it is preferred that the active MMP-9-binding peptide of the present invention specifically binds to active MMP-9.

The binding of the SPINK2 mutant according to the present invention to MMP-9 can be measured or determined using a method known to those skilled in the art, such as ELISA method, Surface Plasmon Resonance (hereinafter referred to as "SPR") analysis method, Biolayer Interferometry (hereinafter referred to as "BLI") method, Isothermal Titration calorimetry (hereinafter referred to as "ITC"), flow cytometry, immunoprecipitation method, and the like.

The ELISA method includes a method of detecting an active MMP-9-binding peptide that recognizes and binds to active MMP-9 immobilized on a plate. For immobilizing active MMP-9 on a plate, in addition to biotin-streptavidin, an antibody for solid phase that recognizes active MMP-9 or a tag fused to active MMP-9 or the like can be used. For detection of an active MMP-9-binding peptide, in addition to a labeled streptavidin, a labeled detection antibody that recognizes active MMP-9-binding peptide or a tag fused to active MMP-9-binding peptide or the like can be used. For labeling, biotin, as well as any other means that can be used for biochemical analysis, such as HRP, alkaline phosphatase, or FITC can be used. For detection using an enzyme label, chromogenic substrates such as TMB (3,3',5,5'-tetramethylbenzidine), BCIP (5-bromo-4-chloro-3-indolyl phosphate), ρ-NPP (ρ-nitrophenyl phosphate), OPD (o-Phenylenediamine), ABTS (3-Ethylbenzothiazoline-6-sulfonic acid), and SuperSignal ELISA Pico Chemiluminescent Substrate (Thermo Fisher Scientific); fluorogenic substrates such as QuantaBlu™ Fluorogenic Peroxidase Substrate (Thermo Fisher Scientific); and chemiluminescent substrates can be used. For measuring detection signals, an absorption plate reader, a fluorescence plate reader, a light emission plate reader, an RI liquid scintillation counter, or the like can be used.

Examples of the devices used for SPR analysis include BIAcore™ (GE Healthcare), ProteOn™ (Bio-Rad Laboratories, Inc.), SPR-Navi™ (BioNavis Oy), Spreeta™ (Texas Instruments Incorporate), SPRi-PlexII™ (HORIBA Scientific), and Autolab SPR™ (Metrohm AG). Examples of the devices used for the BLI method include Octet™ (Pall Corporation).

The immunoprecipitation method includes a method for detecting active MMP-9 which is recognized and bound by the active MMP-9-binding peptide immobilized on beads. As the beads, magnetic beads or agarose beads can be used. For immobilizing the active MMP-9-binding peptide on a plate, biotin-streptavidin as well as an antibody that recognizes an active MMP-9-binding peptide or a tag fused to an active MMP-9-binding peptide, protein A, protein G or the like can be used. The beads are separated by magnets, centrifugation, or the like and the active MMP-9 precipitated with the beads is detected by SDS-PAGE or Western blot methods. For detection of the active MMP-9, labeled streptavidin as well as a labeled detection antibody that recognizes active MMP-9 or a tag fused to active MMP-9 can be used. For labeling, biotin as well as any other means that can be used for biochemical analysis, such as HRP, alkaline phosphatase or FITC can be used. For detection using an enzyme label, the same substrate as in the ELISA method can be used. For measuring detection signals, ChemiDoc™ (Bio-Rad Laboratories, Inc.), Luminograph (ATTO Corporation) and the like can be used.

In the present invention, the "specific recognition" or "specific binding" means a binding that is not non-specific adsorption. Examples of a determination criterion for whether or not the binding is specific include the binding activity $EC_{50}$ in the ELISA method. $EC_{50}$ is a peptide concentration that gives 50% signal when an excess amount of the active MMP-9-binding peptide is added to active MMP-9 immobilized on a plate and the maximum value of the detected signals is taken as 100%. The $EC_{50}$ value of the preferred active MMP-9-binding peptide of the present invention for active MMP-9 is $1 \times 10^{-6}$ M or less, $5 \times 10^{-7}$ M or less, $2 \times 10^{-7}$ M or less, or $1 \times 10^{-7}$ M or less, more preferably $5 \times 10^{-8}$ M or less, $2 \times 10^{-8}$ M or less, or $1 \times 10^{-8}$ M or less, and even more preferably $5 \times 10^{-9}$ M or less, $2 \times 10^{-9}$ M or less, or $1 \times 10^{-9}$ M or less. Preferred active MMP-9-binding peptides in the present invention are active MMP-9 specific binding peptides that do not recognize pro-MMP-9, i.e., do not bind to pro-MMP-9. The $EC_{50}$ value of such active MMP-9 specific binding peptides for pro-MMP-9 is $1 \times 10^{-6}$ M or more, preferably $1 \times 10^{-5}$ M or more. Alternatively, there is no difference in signal intensity between the condition in which the peptide is added at a concentration of $1\times10^{-6}$ M and the condition in which no peptide is added. Examples of another determination criterion include dissociation constant (hereinafter referred to as "$K_D$"). The $K_D$ value of the preferred active MMP-9-binding peptide of the present invention for active MMP-9 is $1\times10^{-5}$ M or less, $5\times10^{-6}$ M or less, $2\times10^{-6}$ M or less, or $1\times10^{-6}$ M or less, more preferably $5\times10^{-7}$ M or less, $2\times10^{-7}$ M or less, or $1\times10^{-7}$ M or less, even more preferably $5\times10^{-8}$ M or less, $2\times10^{-8}$ M or less, or $1\times10^{-8}$ M or less, and still even more preferably $5\times10^{-9}$ M or less, $2\times10^{-9}$ M or less, or $1\times10^{-9}$ M or less. The $K_B$ value for pro-MMP-9 of the preferred active MMP-9-binding peptide of the present invention, that is an active MMP-9 specific binding peptide that does not bind to pro-MMP-9, is $1\times10^{-6}$ M or more, preferably $1\times10^{-5}$ M or more. Further examples of another determination criterion include an analysis result by an immunoprecipitation method. In the immunoprecipitation method, a signal of active MMP-9 is detected, when immobilizing a preferred active MMP-9-binding peptide in the present invention on beads; adding active MMP-9; then separating the beads; and detecting the active MMP-9 precipitated together with the beads. A signal of pro-MMP-9 is not detected, when immobilizing a preferred active MMP-9-binding peptide of the present invention, i.e. an active MMP-9 specific binding peptide that does not bind to pro-MMP-9 on beads; adding pro-MMP-9; then separating the beads; and detecting the pro-MMP-9 precipitated together with the beads. In other words, in the case that a signal of pro-MMP-9 is likewise detected when immobilizing an MMP-9-binding peptide on beads; adding pro-MMP-9; then separating the beads; and detecting the pro-MMP-9 precipitated together with the beads, it can be determined that the MMP-9-binding peptide does not have active MMP-9 specific binding activity.

Furthermore, the active MMP-9-binding peptide in an embodiment of the present invention preferably has MMP-9 inhibitory activity.

MMP-9, the target of the active MMP-9-binding peptide of the present invention, is preferably derived from a vertebrate, more preferably from a mammal, even more preferably from a primate, and most preferably from humans. The amino acid sequence of the pro human MMP-9, that is, full-length mature human MMP-9 (hereinafter referred to as "hMMP-9(full)") consists of the 20th to 707th amino acids of the amino acid sequence represented by SEQ ID NO: 28 (FIG. 44) and does not have a signal sequence of the 1$^{st}$ to 19$^{th}$ amino acids thereof. Examples of the amino acid sequence of the pro human MMP-9 enzyme active domain (hereinafter referred to as "pro-hMMP-9(cat)") include an amino acid sequence consisting of Ala20 to Pro449 or an amino acid sequence containing Ala20 to Gly215 and Gln391 to Tyr443 (from which the fibronectin type II domain involved in binding to the substrate is deleted) of the amino acid sequence represented by SEQ ID NO: 28 (FIG. 44). The amino acid sequence of the active human MMP-9 enzyme active domain (hereinafter referred to as "active hMMP-9(cat)") is not particularly limited as long as the amino acid sequence retains protease activity, and examples of it include an amino acid sequence consisting of Phe107 to Pro449 or an amino acid sequence containing Phe107 to Gly215 and Gln391 to Tyr443 (in which the fibronectin type II domain involved in binding to the substrate is deleted) of the amino acid sequence represented by SEQ ID NO: 28 (FIG. 44). MMP-9 and a functional fragment thereof, which are also denoted as MMP-9 protease, can be purified from tissues or cells, or prepared by a method known to those skilled in the art for preparing proteins, such as gene recombination, in vitro translation, or peptide synthesis. Furthermore, a signal sequence, an immunoglobulin Fc region, a tag, a label, and the like may be linked to MMP-9 or a functional fragment thereof.

The MMP-9 inhibitory activity can be evaluated using the protease activity of MMP-9 as an index. For example, in the case that MMP-9 or a functional fragment thereof, a substrate and an active MMP-9-binding peptide of the present invention or a candidate thereof are coexistent, when the protease activity of MMP-9 is 70% or less, 50% or less, 30% or less, 20% or less, 10% or less, 5% or less, 1% or less, or 0% compared with the case in which the control is present or the inhibitor or a candidate therefor is absent, the MMP-9 is inhibited, and the inhibitory activity is 30% or more, 50% or more, 70% or more, 80% or more, 90% or more, 95% or more, or 99% or more, or 100%, respectively. MMP-9 inhibitory activity may vary depending on the reaction conditions, the type and concentration of the substrate, or the like. Examples of the reaction condition include those described in the Examples below, but are not limited thereto. The enzyme activity can be evaluated by adding a substrate peptide or substrate protein to a certain concentration of MMP-9, causing a reaction of the mixture for a certain period of time, then detecting the fluorescence of the substrate peptide or detecting the substrate protein by SDS-PAGE, a Western blot method, liquid chromatography, or the like. Examples of the buffer solution include phosphate buffer saline (hereinafter referred to as "PBS") and Tris buffer (50 mM Tris, pH 7 to 8.5, for example, pH 7.5). Furthermore, salts such as NaCl (0 to 200 mM, e.g., 200 mM), $CaCl_2$ (0 to 10 mM, e.g., 2 mM), $ZnCl_2$, and Brij-35 can be added to the buffer solution. However, the buffer solution is not limited to these.

The substrates of the MMP-9 protease are not particularly limited, and examples of them include endogenous substrates, exogenous substrates, and synthetic substrates. As a human endogenous substrate, collagen can be exemplified. The gelatin obtained by heat denaturation of collagen can also be used as a substrate. Examples of the synthetic substrate include, but are not limited to, MOCAc—KPLGL-$A_2$pr(Dnp)-AR—$NH_2$ (SEQ ID NO: 30, FIG. 46), MOCAc—PLGL-$A_2$pr(Dnp)-AR—$NH_2$ (SEQ ID NO: 31, FIG. 47), DNP—PLGMWSR (SEQ ID NO: 32, FIG. 48), and MOCAc—RPKPVE-Nva-WR-Lys(Dnp)-$NH_2$ (SEQ ID NO: 33, FIG. 49). The MMP-9 inhibitory activity ($IC_{50}$ or $K_i$) of the active MMP-9-binding peptide of the present invention is 1 µM or less, preferably 100 nM or less, more preferably 10 nM or less, even more preferably 1 nM or less.

Furthermore, it is also preferred that the active MMP-9-binding peptide of the present invention does not inhibit or suppress the activities of proteases other than MMP-9, or the degree of inhibition or suppression of the activities of proteases other than MMP-9 is relatively weak. In other words, the protease inhibitory activity of the active MMP-9-binding peptide of the present invention preferably has high MMP-9 specificity. The preferred active MMP-9-binding peptide of the present invention does not inhibit or suppress the protease activities of MMP-1, MMP-2, MMP-3, MMP-7, MMP-8, MMP-10, MMP-12, MMP-13, MMP-14, MMP-15, MMP-16, MMP-17, ADAM17 and the like, or the degree of inhibition or suppression thereof is relatively weak. More preferred active MMP-9-binding peptides of the present invention are those that do not inhibit or suppress the protease activities of trypsin, chymotrypsin, tryptase, chymase, plasmin, thrombin, elastase, matriptase, protein C, tPA, uPA, plasma kallikrein, or the like, or the degree of inhibition or suppression thereof is relatively weak. Such preferred peptides of the present invention have no side effects caused by inhibition or suppression of the activities of other proteases, and can suitably be used as the therapeutic or preventive agents for diseases related to MMP-9 (described later).

The inhibitors having low specificity for MMP-9 and inhibiting protease activities of the other MMPs as well as MMP-9, that is non-selective MMP-9 inhibitors, cause serious side effects when administered to humans. Small molecule inhibitors that chelate a zinc ion are non-selective MMP-9 inhibitors, and in clinical trials in which these inhibitors were administered, serious musculoskeletal side effects such as bone and joint pain and contracture were observed (Non Patent Literature 6 and 7). In contrast, there is a high possibility that the inhibitors having high specificity for MMP-9, i.e., MMP-9 specific inhibitors, can avoid such side effects as described above. It was reported in a safety study with rats that when non-selective MMP-9 inhibitor Marimastat was administered to a group, the symptoms of musculoskeletal syndrome were observed, whereas no such symptoms were observed in the group to which an MMP-9 specific inhibitory antibody was administered (Patent Literature 6). Thus, the active MMP-9-binding peptides of the present invention that specifically inhibit the protease activity of MMP-9 can suitably be used for treatment or prevention of diseases related to MMP-9.

The active MMP-9-binding peptides of the present invention may be competitive for binding of the protease substrate to MMP-9.

As noted above, MMP-9, the target of the peptides of the present invention, is derived from vertebrates, preferably mammals, more preferably primates, and even more preferably humans, but it may be derived from a non-human animal, for example, rodents such as rat and mouse and primates such as cynomolgus monkey, common marmoset, and rhesus monkey. A peptide having active MMP-9-specific binding activity for MMP-9 derived from a non-human animal can be used for detection and measurement specific to active MMP-9 of such a non-human animal. Furthermore, the peptide of the present invention targeting MMP-9 derived from a non-human animal may be a peptide that inhibits protease activity of MMP-9 derived from such a non-human animal. Such a peptide having the active-form specific binding activity and/or protease inhibitory activity for MMP-9 derived from a non-human animal can be used to diagnose, test, treat or prevent diseases related to MMP-9 in such a non-human animal. Furthermore, when such a peptide having protease inhibitory activity for MMP-9 derived from a non-human animal also inhibits protease activity of human MMP-9, the peptide can be used in pharmacological and pharmacokinetic tests using such a non-human animal as an animal pathological model, and in safety tests and toxicity tests using such a non-human animal as a healthy animal, during non-clinical research and development of the peptide as a therapeutic or prophylactic agent for diseases related to human MMP-9.

The active MMP-9-binding peptide of the present invention has a smaller molecular weight than other biomacromolecules such as antibodies used in this field as a pharmaceutical or diagnostic agent, and the production of the peptide (described later) is relatively easy. The peptide of the present invention is also excellent in terms of physical properties such as storage stability and heat stability. Furthermore, the peptide has advantages in that it has many options for administration route, administration method, formulation, or the like when used in a pharmaceutical composition (described later). It is also possible to adjust the blood half-life of the peptide to be longer when using the peptide as a pharmaceutical composition by increasing the molecular weight of the peptides of the present invention with a known method such as addition of a biomacromolecule or a polymer. The molecular weight of such an active MMP-9-binding peptide of the present invention is less than 10,000, preferably less than 8,000, more preferably about 7,000 to 7,200. Among a variable loop portion consisting of Cys 15 to Cys 31 and a moiety consisting of Cys 15 to Cys 63 of SEQ ID NO: 18 (FIG. 32) (hereinafter referred to as a "moiety containing 6 Cys"), ones having active MMP-9-binding activity are also included in the active MMP-9-binding peptide of the present invention. The molecular weight of the variable loop portion is less than 2,500, preferably about 1,800 to 2,000, and the molecular weight of the moiety containing 6 Cys is less than 6,000, preferably about 5,300 to 5,500.

The SPINK2 mutant as the active MMP-9-binding peptide of the present invention may have the specific binding activity, protease inhibitory activity, and other properties, functions, features or the like as described above, while the full-length amino acid sequence of the active MMP-9-binding peptide has high sequence identity to the amino acid sequence of human wild type SPINK2. The amino acid sequence of the SPINK2 mutant of the present invention has a sequence identity of 60% or more, 70% or more, 75% or more, 80% or more, 85% or more, 90% or more, 95% or more, 98% or more, or 99% or more to the amino acid sequence of human SPINK2 (SEQ ID NO: 1, FIG. 15).

The term "identity" means a property that indicates the degree of similarity or relationship between two sequences. The amino acid sequence identity (%) is calculated by dividing the number of identical amino acids or amino acid residues by the total number of amino acids or amino acid residues, and by multiplying the obtained numerical value by 100.

The term "gap" means a gap in the alignment among two or more sequences resulting from a deletion and/or addition in at least one of the two or more sequences.

The identity between two amino acid sequences having completely identical amino acid sequences is 100%, while, if there is a substitution, deletion or addition of one or two or more amino acids or amino acid residues in one amino acid sequence compared to the other sequence, the identity of both is less than 100%. Examples of algorithms and programs for determining the identity between the two sequences while considering gaps include those known to one of ordinary skill in the art, such as BLAST (Altschul, et al. Nucleic Acids Res., Vol. 25, pp. 3389-3402, 1997), BLAST2 (Altschul, et al. J. Mol. Biol., Vol. 215, pp. 403-410, 1990), and Smith-Waterman (Smith, et al. J. Mol. Biol., Vol. 147, pp. 195-197, 1981) and the like, in which standard parameters are used.

In the present invention, the term "mutated" means that a substitution, a deletion or an insertion of one or two or more nucleotides or nucleotide residues or amino acids or amino acid residues has been made in a nucleotide sequence or amino acid sequence compared to a naturally occurring nucleic acid molecule or peptide. The amino acid sequence of the SPINK2 mutant of the present invention has one or two or more amino acids or amino acid residues mutated, as compared to the amino acid sequence of human SPINK2.

In one embodiment of the present invention, the amino acid sequence of the SPINK2 mutant has, in the amino acid sequence of human SPINK2 (SEQ ID NO: 1, FIG. 15), a substitution of one, two, three, four, five, six, or seven amino acids of Ser16 to Gly22 with another amino acid or amino acid residue; and a substitution of one, two, three, four, or five amino acids of Pro24 to Asn28 with another amino acid or amino acid residue.

It is preferred that Cys15, Cys23, Cys31, Cys42, Cys45, and Cys63 are Cys as in the wild type, in order to maintain the naturally occurring disulfide bonds. However, one, two, three, four, five or six of them may be substituted with another amino acids so as to eliminate the naturally occurring disulfide bonds or to generate a non-naturally occurring disulfide bond. In some preferred active MMP-9-binding peptides of the SPINK2 mutants of the present invention, Cys are maintained at the same 6 positions as those in the naturally occurring peptide, thus the disulfide bonds are maintained. In some more preferred embodiments of such active MMP-9-binding peptides, Cys15-Cys45, Cys23-Cys42, and Cys31-Cys63 each form a disulfide bond.

When such an amino acid sequence of the SPINK2 mutant is contained in the active MMP-9-binding peptide, it is preferred that the structures including a loop structure consisting of Ser16 to Val30, a β sheet composed of β strand (1) consisting of Cys31 and Gly32 and β strand (2) consisting of Ile57 to Arg59, and an α helix consisting of Glu41 to Gly51, or a loop structure, a β sheet and an α helix similar thereto or at least partially corresponding thereto (or to the positions thereof) contained in the amino acid sequence of the wild-type SPINK2 are maintained to the extent that the active MMP-9-binding activity can be exhibited.

Among the SPINK2 mutants of the present invention, the amino acid sequences of some active MMP-9-binding peptides are described below. As described above, the term "amino acid residue" is sometimes simply expressed as "amino acid", in the present invention.

In the amino acid sequence represented by SEQ ID NO: 18 (FIG. 32), each of $X_1$ to $X_{13}$ are not particularly limited as long as they are any amino acids and to the extent that the active MMP-9-binding peptide binds to MMP-9 and inhibits MMP-9 activity. Hereinafter, preferred amino acids of $X_1$ to $X_{13}$ are described, but they may include naturally occurring amino acids, i.e., the same amino acids as in the amino acid sequence of the wild type human SPINK2.

The 1$^{st}$ $X_1$ is preferably Asp or Gly, more preferably Gly.

When, 21$^{st}$ $X_7$ is Pro, 24$^{th}$ $X_9$ is Gln and 25th $X_{10}$ is Met, 16$^{th}$ $X_2$ is preferably Arg, Gln, Gly, Trp or Tyr, more preferably Arg or Gln;

17$^{th}$ $X_3$ is preferably Arg, Asp, Gln, Glu, Lys, Met, Ser, Thr or Val, more preferably Arg, Gln, Lys, Thr or Val;

18$^{th}$ $X_4$ is preferably Ala, Arg, Asn, Asp, Gln, Gly, Leu, Lys or Val, more preferably Arg, Gly or Val;

19$^{th}$ $X_5$ is preferably Ala, Arg, Asn, Gly, Ile, Leu or Lys, more preferably Arg, Gly, Ile or Lys;

20$^{th}$ $X_6$ is preferably Ala, Glu, Gly, Met or Ser, more preferably Glu or Gly;

22$^{nd}$ $X_8$ is preferably Ala, Leu or Ser, more preferably Ala or Ser;

26$^{th}$ $X_{11}$ is preferably Ala, Gly or Ser;

27$^{th}$ $X_{12}$ is preferably Leu, Phe, Ser or Tyr, more preferably Phe or Tyr; and 28$^{th}$ $X_{13}$ is preferably Asn, Asp, Gln, Leu or Lys, more preferably Asn, Gln or Lys.

When 20th $X_6$ is Tyr, 22nd $X_8$ is Gln and 24th $X_9$ is Ser, 16$^{th}$ $X_2$ is preferably Arg, Lys, Met or Val, more preferably Met or Val;

17$^{th}$ $X_3$ is preferably Arg, Gln, Lys or Met, more preferably Met;

18$^{th}$ $X_4$ is preferably Phe or Tyr, more preferably Tyr;

19$^{th}$ $X_5$ is preferably Gln, Glu or Lys, more preferably Lys;

21$^{st}$ $X_7$ is preferably Ala or Gly, more preferably Ala;

25$^{th}$ $X_{10}$ is preferably Asn or His, more preferably His;

26$^{th}$ $X_{11}$ is preferably Leu, Lys, Met or Val, more preferably Lys;

27$^{th}$ $X_{12}$ is preferably Phe, Ser or Tyr, more preferably Ser or Tyr; and 28$^{th}$ $X_{13}$ is preferably Ala, Asn, Gln or Lys, more preferably Gln or Lys.

The wild type $X_1$ to $X_{13}$ are Asp, Ser, Gln, Tyr, Arg, Leu, Pro, Gly, Pro, Arg, His, Phe and Asn, respectively.

In the present invention, one to several or more amino acids may be further added to the N-terminal side of the first amino acid. Examples of such amino acids to be added include an amino acid sequence consisting of Stag+linker (SEQ ID NOs: 19 and 20, FIGS. 33 and 34).

Furthermore, one to several amino acids may be added to Cys63 located at the C-terminal. For example, Gly-Gly may be added to the C-terminal, and an amino acid sequence having Gly65 at the C-terminal can be obtained. Examples of such amino acids to be added include a C-terminal 6-mer (SEQ ID NO: 21, FIG. 35), Gly-Gly-Gly (FIG. 36), and Gly-Gly (FIG. 37).

In the present invention, the peptide obtained by substituting, adding, and/or deleting one or two or more amino acids in a SPINK2 mutant peptide or an N-terminal and/or C-terminal adduct of SPINK2 mutant peptide (hereinafter referred to as "parent peptide") are sometimes referred to as the "derivative of the parent peptide" or "parent peptide derivative". Such a "derivative" is also included in the scope of the "peptide" of the present invention.

In the amino acid sequence of the SPINK2 mutant included in the scope of the active MMP-9-binding peptide of the present invention, the moieties other than $X_1$ to $X_{13}$, i.e., positions of Pro2 to Cys15, Cys23 and Pro29 to Cys63 in the amino acid sequence of wild type human SPINK2 (SEQ ID NO: 1, FIG. 15) can include a naturally occurring amino acid or a mutated amino acid or an amino acid sequence. For example, a SPINK2 mutant may be mutated at any one or two or more positions as long as the mutation does not completely hinder or interfere with the active MMP-9-binding activity or folding. Such mutation may be made by using a standard method known to those skilled in the art. Typical mutations in amino acid sequences can include substitutions, deletions, or additions of one or two or more amino acids. Examples of the substitutions include conservative substitutions. By a conservative substitution, a certain amino acid residue is substituted by another amino acid residue that has similar chemical characteristics in terms of not only bulk height but also polarity. Examples of the conservative substitutions are described elsewhere in this specification. However, in the moieties other than $X_1$ to $X_{13}$, non-conservative substitutions of one or two or more amino acids may be allowed as long as the substitution does not completely hinder or interfere with the active MMP-9-binding activity or folding.

In relation to the amino acid sequence of the SPINK2 mutant as the active MMP-9-binding peptide of the present invention, $X_1$ to $X_{13}$ are preferably the respective amino acids of $X_1$ to $X_{13}$ in any one of SEQ ID NOs: 2 to 17 (FIGS. 16 to 31), and the moieties other than $X_1$ to $X_{13}$ can have any amino acid or amino acid sequence which does not completely hinder or interfere with the active MMP-9-binding activity or folding.

Examples of the amino acid sequence of the SPINK2 mutant as the active MMP-9-binding peptide of the present invention include the amino acid sequences described in any one of the following (a) to (d):

(a) an amino acid sequence represented by any one of SEQ ID NOs: 2 to 17 (FIGS. 16 to 31);

(b) an amino acid sequence encoded by a nucleotide sequence that hybridizes with a nucleotide sequence complementary to the nucleotide sequence encoding the amino acid sequence described in (a) under stringent conditions, and encodes an amino acid sequence contained in a peptide having active MMP-9-binding activity;

(c) an amino acid sequence having 1 to 20, 1 to 15, 1 to 10, 1 to 8, 1 to 6, 1 to 5, 1 to 4, 1 to 3, 1 to 2, or 1 amino acid substitutions, deletions, additions and/or insertions in the amino acid sequence described in (a), and contained in a peptide having active MMP-9-binding activity; and (d) an amino acid sequence that is 60%, 70%, 80%, 85%, 90%, 92%, 94%, 96%, 97%, 98% or 99% or more identical to the amino acid sequence described in (a), and contained in a peptide having active MMP-9-binding activity.

The peptide consisting of or containing the amino acid sequence described in any one of (a) to (d) above preferably does not bind to pro-MMP-9, and more preferably inhibits protease activity of MMP-9, and even more preferably, specifically inhibits protease activity of MMP-9 (such peptides are referred to as an "MMP-9 specific inhibitory peptide" or an "MMP-9 specific inhibitory SPINK2 mutant peptide").

Mutations can be introduced into the active MMP-9-binding peptide of the present invention, in order to improve the folding stability, heat stability, storage stability, blood half-life, water solubility, biological activity, pharmacological activity, secondary effects, or the like. For example, a new reactive group such as Cys can be introduced by mutation to conjugate to other substances such as polyethylene glycol (PEG), hydroxyethyl starch (HES), biotin, a peptide or a protein.

In the present invention, the active MMP-9-binding peptide may be conjugated to another moiety, and such a conjugate is collectively referred to as "conjugate of active MMP-9-binding peptide". The "conjugate" or "conjugation" includes a form in which a certain moiety is linked to the peptide of the present invention through a chemical substance such as a cross-linking agent, or through an agent suitable for linking to the side chain of an amino acid, or by genetic engineering techniques to the N-terminal and/or C-terminal of the peptide of the present invention. Examples of such a "moiety" for improving blood half-life include polyalkylene glycol molecules such as polyethylene glycol (PEG); hydroxyethyl starch; fatty acid molecules such as palmitic acid, or the like; Fc regions of immunoglobulins; CH3 domains of immunoglobulins; CH4 domains of immunoglobulins; albumin or fragments thereof; albumin-binding peptides; albumin-binding proteins such as streptococcal protein G; and transferrin. Other examples of the "moiety" include a "moiety" that can be linked to a peptide of the present invention via a linker, such as a peptide linker.

Furthermore, a drug may be conjugated to the active MMP-9-binding peptide of the present invention in order to exert or enhance the pharmacological activity. Techniques and embodiments known to those skilled in the art as antibody-drug conjugates (ADCs) in the antibody field can become an embodiment of the present invention by replacing the antibody with the peptide of the present invention.

The active MMP-9-binding peptide of the present invention may further contain one or two or more moieties that exhibit binding affinity, inhibitory activity, antagonistic activity, agonistic activity and the like for target molecules other than MMP-9, or may be conjugated to such moieties. Examples of such a "moiety" include an antibody or a fragment thereof, and a protein having a backbone other than an antibody such as a SPINK2 mutant or a fragment thereof. Techniques and embodiments known to those skilled in the art as multispecific antibodies and bispecific antibodies in the field of antibodies can become an embodiment of the embodiment of the conjugate of the present invention by substituting at least one of two or more "antibodies" contained in those with the peptide of the present invention.

The active MMP-9-binding peptide of the present invention or a precursor thereof may contain a signal sequence. A signal sequence present at or added to the N-terminal of a polypeptide or a precursor thereof is useful to deliver the polypeptide to a specific compartment of a cell, for example, periplasm in the case of E. coli or endoplasmic reticulum in the case of a eukaryotic cell. Many signal sequences are known to those of skill in the art and can be selected depending on the host cell. Examples of the signal sequence for secreting a desired peptide in the periplasm of E. coli include OmpA. The conjugates having a form containing such a signal sequence may also be included in the conjugate of the present invention as an embodiment thereof.

Furthermore, by adding a tag to the active MMP-9-binding peptide of the present invention in advance, the peptide can be purified by affinity chromatography. For example, the peptide of the present invention may have, at the C-terminal, biotin, a Strep Tag™, a Strep tag II™, oligohistidine such as His6, polyhistidine, an immunoglobulin domain, a maltose binding protein, glutathione-S-transferase (GST), a calmodulin-binding peptide (CBP), a hapten such as digoxigenin or dinitrophenol, an epitope tag such as FLAG™, a myc tag, a HA tag, or the like (hereinafter collectively referred to as "affinity tags"). The peptide to which the tag is added may also be included in the conjugate of the present invention as an embodiment thereof.

The active MMP-9-binding peptide of the present invention may contain a moiety for labeling. Specifically, a labeling moiety such as an enzyme label, a radioactive label, a color label, a fluorescent label, a chromogenic label, a luminescent label, a hapten, digoxigenin, biotin, a metal complex, a metal, colloidal gold, or the like may be conjugated to the peptide. The peptide which contains the moiety for labeling may also be included in the conjugate of the present invention as an embodiment thereof.

The active MMP-9-binding peptide of the present invention can contain both naturally occurring amino acids and non-naturally occurring amino acids in the peptide moiety, and the naturally occurring amino acids can contain both L-amino acids and D-amino acids.

The amino acid sequence of the active MMP-9-binding peptide of the present invention can contain both naturally occurring amino acids and non-naturally occurring amino acids, and the naturally occurring amino acids can contain both L-amino acids and D-amino acids.

The active MMP-9-binding peptide of the present invention may exist as a monomer, a dimer, a trimer or higher oligomer, or a multimer. The dimer, trimer or higher oligomer and multimer may be either a homomer composed of a single monomer, or a heteromer composed of two or more different monomers. Monomers may, for example, diffuse rapidly and have excellent penetration into tissues. The dimer, oligomer and multimer may have advantages in some aspects, for example, they may have high affinity for or binding activity to the target molecule in a localized tissue, may have a slow dissociation rate, or may exhibit high active MMP-9-binding activity. In addition to spontaneous dimerization, oligomerization, and multimerization, the intended dimerization, oligomerization, and multimerization can also be achieved by introducing a jun-fos domain, a leucine zipper or the like into the active MMP-9-binding peptide of the present invention.

The active MMP-9-binding peptide of the present invention can bind to one or two or more target molecules, or inhibit the activity of the target molecules as a monomer, dimer, trimer or higher oligomer, or a multimer.

The active MMP-9-binding peptide of the present invention can be in an isolated form (a lyophilized preparation, solution, or the like), a conjugate form as described above, or a form bound to another molecule (a form immobilized on a plate, a form associated with a different molecule, a form bound to a target molecule, or the like), but is not limited to these, and can take any form suitable for expression, purification, use, storage, or the like.

In certain embodiments, a binding site on an active human MMP-9 molecule recognized by an MMP-9 inhibitory peptide, particularly an MMP-9 specific inhibitory peptide, that is a preferred active MMP-9-binding peptide of the present invention, may be the following (i) or (ii):

(i) in the amino acid sequence of active MMP-9 (SEQ ID NO: 28), (ia) Glu402, and (ib) one or two or more amino acids selected from the group consisting of Phe110, Tyr179, Leu187, Phe192, Gln199, Tyr393, Leu397, Val398, Tyr420, Met422, and Tyr423; or (ii) in the amino acid sequence of active MMP-9 (SEQ ID NO: 28), (iia) Glu402, and (iib) one or two or more amino acids selected from the group consisting of Tyr179, Asp185, Phe192, Phe193, Tyr393, Leu397, Val398, Met422, Tyr423, and Arg424.

Here, the "two or more" is preferably 3 or more, 4 or more, 5 or more, or 6 or more, more preferably 7 or more, 8 or more, or 9 or more, and optimally 10, or 10 or 11.

The binding site on the active MMP-9 molecule recognized by an active MMP-9-binding peptide can be identified by measuring the inhibitory activity of the peptide using the wild type and a mutant of active MMP-9. For example, when inhibitory concentration ($IC_{50}$) of a test compound for a substrate peptide degrading activity of an active MMP-9 mutant in which an nnn-th amino acid X is substituted is increased, compared to the 50% $IC_{50}$ of the test compound measured with the substrate peptide degrading activity of the wild-type active MMP-9 as 100%, for example, 2 times or more, preferably 3 times or more, more preferably 4 times or more, and even more preferably 5 times or more, though the criteria is not particularly limited, it is determined that the test compound recognizes the nnn-th amino acid X and binds to active MMP-9.

3. Identification of Active MMP-9-Binding Peptide

Active MMP-9-binding peptides can be identified by a method well known to those skilled in the art, using the amino acid sequence of SPINK2 or the amino acid sequence of the active MMP-9-binding peptide of the present invention (for example, the amino acid sequence selected from the group consisting of SEQ ID NOs: 2 to 17 or the group consisting of FIGS. 16 to 31), a nucleotide sequence encoding the amino acid sequence, a nucleic acid molecule containing the nucleotide sequence and the like as a starting material. As a preferred example, the active MMP-9-binding peptide can be identified from a human SPINK2 mutant library, using the active MMP-9-binding activity as an index. The pro-MMP-9-binding activity or MMP-9 inhibitory activity may also be combined as an index.

In an example, a nucleic acid molecule which is a starting material may be subjected to induction of mutation, and introduced into a suitable bacterial or eukaryotic host using a recombinant DNA technology. SPINK2 mutant libraries are known as a technique for identifying a binder or inhibitor of a target molecule. For example, a SPINK2 mutant library disclosed in WO2012/105616 is incorporated herein by reference in its entirety. After expressing the nucleotide sequence subjected to induction of mutation in an appropriate host, a clone, of which the genetic trait is linked to the SPINK2 mutant having a desired property, activity, function or the like, can be enriched and/or screened, and identified from the library. For enrichment and/or screening of the clone, a method known to those skilled in the art, such as a bacterial display method (Francisco, J. A., et al. (1993) Proc. Natl. Acad. Sci. U.S.A., Vol. 90, pp. 10444-10448), a yeast display method (Boder, E. T., et al. (1997) Nat. Biotechnol., Vol. 15, pp. 553-557), a mammalian cell display method (Ho M, et al. (2009) Methods Mol Biol., Vol. 525: pp. 337-52), a phage display method (Smith, G. P. (1985) Science., Vol. 228, pp. 1315-1317), a ribosomal display method (Mattheakis L C, et al. (1994) Proc. Natl. Acad. Sci. U.S.A., Vol. 91, No. 19, pp. 9022-9029), a nucleic acid display method such as an mRNA display method (Nemoto N, et al. (1997) FEBS Lett., Vol. 414, No. 2, pp. 405-408), a colony screening method (Pini, A. et al. (2002) Comb. Chem. High Throughput Screen. Vol. 5, pp. 503-510) or the like can be used. By sequencing the nucleotide sequence of the SPINK2 mutant contained in the selected and identified clone, the amino acid sequence encoded by the nucleotide sequence can be determined as the amino acid sequence of the SPINK2 mutant, i.e., the active MMP-9-binding peptide, contained in the clone.

The SPINK2 mutant of the present invention can be obtained, for example, by inducing mutation in naturally occurring SPINK2. The term "inducing mutation" refers to causing one or two or more amino acids present at respective positions of an amino acid sequence to be substituted with another amino acid or to be deleted, or to cause addition or insertion of an amino acid that is not present in the amino acid sequence. Such deletion, addition or insertion may alter the sequence length. In the SPINK2 mutant of the present invention, the induction of the mutation may preferably occur at one or two or more positions of $X_1$ to $X_{13}$ in the amino acid sequence represented by SEQ ID NO: 18 (FIG. 32).

However, ones which maintain, after inducing such a suitable mutation, the naturally occurring amino acid that is the same amino acid as the amino acid present in the naturally occurring amino acid sequence at a specific position, in one or two or more positions of $X_1$ to $X_{13}$, are also included within the scope of the mutant as long as they have at least one mutated amino acid in their entirety. Likewise, in an embodiment of the present invention, ones which maintain, after inducing a mutation in one or more positions in the moieties other than $X_1$ to $X_{13}$, the naturally occurring amino acid that is the same amino acid as the amino acid present in the naturally occurring amino acid sequence at a specific position, are also included within the scope of the mutants as long as they have at least one mutated amino acid in their entirety.

The term "inducing random mutation" means that an induction of a mutation for a specific position on a sequence causes introduction of one or two or more different amino acids with a certain probability at the specific position, in which each of the probabilities for at least two different amino acids to be introduced are not necessarily all the same. Furthermore, in the present invention, said at least two different amino acids may include one being the same residue as the naturally occurring (wild type) amino acid, and this case is also included within the scope of the term "inducing random mutation".

As a method for inducing random mutation at a specific position, a standard method known to those skilled in the art can be used. For example, mutation can be induced at a specific position in the sequence by PCR (polymerase chain reaction) using a mixture of synthetic oligonucleotides containing a degenerate nucleotide composition. For example, the use of codon NNK or NNS (N=adenine, guanine, cytosine or thymine; K=guanine or thymine; S=adenine or cytosine) induces mutation in which all 20 naturally occurring amino acids as well as stop codons are introduced. Whereas the use of codon VVS (V=adenine, guanine or cytosine) has no possibility of causing the introduction of Cys, Ile, Leu, Met, Phe, Trp, Tyr, and Val, mutation causing the introduction of the remaining 12 naturally occurring amino acids is induced. Furthermore, for example, the use of codon NMS (M=adenine or cytosine) has no possibility of causing the introduction of Arg, Cys, Gly, Ile, Leu, Met, Phe, Trp and Val, but mutation causing the introduction of the remaining 11 naturally occurring amino acids is induced. Special codons, artificial codons, or the like can be used to induce mutation causing the introduction of non-naturally occurring amino acids.

Site-specific induction of mutation can also be performed using structural information of a target having a higher-order structure and/or a peptide against the target or a wild-type peptide from which the peptide is derived. In the present invention, site-specific mutation can be introduced using structural information including higher-order structural information of (a) MMP-9 which is the target, and/or, (b) a SPINK2 mutant against the target or the wild-type SPINK2, or, (c) a complex of both (a) and (b). For example, structural information obtained by identifying a SPINK2 mutant having active MMP-9-binding activity; performing X-ray crystal structure analysis after obtaining a crystal of a complex of MMP-9 and the SPINK2 mutant; and identifying, based on the analysis result, an epitope on the MMP-9 molecule to which the SPINK2 mutant binds and a paratope on the SPINK2 mutant corresponding to the epitope, may be found to have a correlation with the active MMP-9-binding activity. Based on such a structure-activity relationship, it is possible to design a substitution with a specific amino acid at a specific position, an insertion or deletion of an amino acid at a specific position, or the like, and actually confirm the active MMP-9-binding activity. In addition, induction of mutation can be performed, for example, with a nucleotide constitutive unit having altered base-pair specificity, such as inosine.

Furthermore, inducing mutation at random positions is possible, for example, by error-prone PCR using a DNA polymerase that lacks a proofreading function and has a high error rate, such as Taq DNA polymerase, by chemical mutagenesis, or the like.

The active MMP-9-binding peptide can be enriched and/or screened by using bacterial display, yeast display, mammalian cell display, phage display, ribosome display, nucleic acid display, colony screening or the like, from libraries known to those skilled in the art, such as a phage library or a colony library, suitable for each screening method. These libraries can be constructed with vectors and methods known to those skilled in the art, suitable for each library, such as phagemids for phage library, and cosmids for colony screening. Such vectors may be viruses or viral vectors that infect prokaryotic or eukaryotic cells. These recombinant vectors can be prepared by a method known to those skilled in the art, such as genetic engineering.

Bacterial display is a technique for presenting a desired protein, for example, on the surface of E. coli, by fusing the desired protein to a part of the outer membrane lipoprotein (Lpp) of E. coli and the outer membrane protein OmpA. A library presenting a group of random mutated proteins on the surface of the transformed bacterial cells can be obtained by inducing random mutation in a nucleotide sequence encoding an amino acid sequence of a certain protein, introducing a DNA group obtained by the induction of random mutation into a vector suitable for bacterial display, and transforming bacterial cells with the vector (Francisco, J. A., et al. (1993), Proc. Natl. Acad. Sci. U.S.A. Vol. 90, pp. 10444-10448).

Yeast display is a technique for presenting a desired protein on the surface of yeast by fusing the desired protein to a protein such as α-agglutinin present on the outer shell of the cell surface of the yeast. The α-agglutinin includes a C-terminal hydrophobic region that is presumed to be a glycosylphosphatidylinositol (GPI) anchor attachment signal, a signal sequence, an active domain, a cell wall domain, and the like. With manipulation of these elements, it is possible to display a desired protein on the cell surface of yeast. A library presenting a group of random mutated proteins on the surface of transformed yeast cells can be obtained by inducing random mutation in a nucleotide sequence encoding an amino acid sequence of a certain protein, introducing a DNA group, obtained by the induction of random mutation, into a vector suitable for yeast display, and transforming yeast cells with the vector (Ueda, M.& Tanaka, A., Biotechnol. Adv., Vol. 18, p. 121 (2000): Ueda, M.& Tanaka, A., J. Biosci. Bioeng., Vol. 90, p. 125 (2000), and other literature).

Animal cell display is a technique for presenting a desired protein on the surface of mammalian cells such as HEK293 or Chinese hamster ovary (CHO) cells by, for example, fusing a desired protein to a transmembrane region of a membrane protein such as a platelet-derived growth factor receptor (PDGFR). A library presenting a group of random mutated proteins on the surface of transformed animal cells can be obtained by inducing random mutation in a nucleotide sequence encoding an amino acid sequence of a certain protein, introducing a DNA group, obtained by the induction of random mutation, into a vector suitable for animal cell display, and transforming animal cells with the vector (Ho M, et al. (2009) Methods Mol Biol. Vol. 525: pp. 337-52).

The desired library presented on cells such as yeast, bacteria, and animal cells can be incubated in the presence of the target molecule or contacted with the target molecule. For example, MMP-9 modified with biotin or the like and cells containing the library are incubated for a certain period of time, then a carrier such as magnetic beads is added, and the cells are separated from the carrier, and subsequently the carrier is washed to remove non-specific, adsorption or binding substances, thus the cell group presenting the peptide, the peptide assembly or the concentrated peptide assembly bound to the carrier (or MMP-9 bound to the carrier) can be recovered. Similarly, the cell group presenting the peptide, the peptide assembly or the concentrated peptide assembly bound to the carrier (or MMP-9 bound to the carrier) or MMP-9 can be recovered by performing magnetic cell separation (MACS) after adding magnetic beads, or by performing FACS after cell staining using anti-MMP-9 antibodies. Non-specific adsorption sites and/or binding sites can be subjected to, for example, blocking treatment, and a blocking step by an appropriate method may be incorporated. By recovering a vector expressing the peptide thus obtained, the peptide assembly or the concentrated peptide assembly, and then sequencing a nucleotide sequence of the polynucleotide inserted into the vector, the amino acid sequence encoded by the nucleotide sequence can be determined. In addition, the peptide assembly that binds to the target molecule can be highly concentrated by introducing the vector again into the host cell, and repeating the above procedures in a cycle once or several times.

In phage display, a phagemid is a bacterial plasmid, for example, containing a second origin of replication derived from a single-stranded bacteriophage, in addition to the origin of plasmid replication. Cells containing a phagemid can replicate the phagemid through single-stranded replication mode, in superinfection with M13 or similar helper bacteriophage. That is, single-stranded phagemid DNA is packaged in infectious particles coated with a bacteriophage coat protein. In this manner, phagemid DNA can be formed as a cloned double-stranded DNA plasmid in infected bacteria, or phagemid can be formed as bacteriophage-like particles from the culture supernatant of superinfected cells, respectively. The particles themselves can be formed again as plasmids by injecting the bacteriophage-like particles into the bacteria to infect such DNA with F-fibrotic bacteria.

By inserting a fusion gene containing a polynucleotide having a nucleotide sequence encoding an amino acid sequence of a test peptide and a bacteriophage coat protein gene into such a phagemid, and infecting the phagemid with bacteria, and then culturing the cell, it is possible to cause such a peptide to be expressed or presented (in other words, displayed) on the bacteria or phage-like particles, or to be produced in phage particles or culture supernatant of the bacteria as a fusion protein with the coat protein.

For example, by inserting a fusion gene containing the polynucleotide and a bacteriophage coat protein gene gpIII into a phagemid, and then superinfecting E. coli with phagemid along with M13 or a similar helper phage, it is possible to cause such a peptide to be produced in the culture supernatant of E. coli as a fusion protein containing the peptide and the coat protein.

When various circular or non-circular vectors such as viral vectors are used instead of the phagemid, it is possible to cause a peptide having an amino acid sequence encoded by the nucleotide sequence of the polynucleotide inserted into such a vector according to a method known to those skilled in the art to be expressed or presented on the cell or virus-like particles to which the vector has been introduced, or to be produced in a culture supernatant of the cell.

The library expressing the peptide thus obtained can be incubated in the presence of the target molecule or contacted with the target molecule. For example, a carrier on which MMP-9 is immobilized on a plate is incubated with a mobile phase containing a library for a certain period of time, then the mobile phase is separated from the carrier, and then the carrier is washed to remove non-specific, adsorption or binding substances, thus the peptide, the peptide assembly or the concentrated peptide assembly bound to the carrier (or MMP-9 bound to the carrier) can be recovered by elution. Elution can be performed non-selectively under relatively high ionic strength, low pH, moderate denaturing conditions, the presence of chaotropic salts, or the like, or performed selectively by adding the soluble target molecule such as MMP-9, an antibody bound to the target molecule, a naturally occurring ligand, a substrate or the like to compete with the target molecule immobilized on a plate. Non-specific, adsorption sites and/or binding sites can be subjected to, for example, blocking treatment, and a blocking step by an appropriate method may be incorporated.

By recovering a vector expressing the peptide thus obtained, or a peptide assembly or a concentrated peptide assembly, then sequencing nucleotide sequences of the polynucleotide inserted into the vector, the amino acid sequence encoded by the nucleotide sequence can be determined. In addition, the peptide assembly that binds to the target molecule can be highly concentrated by introducing the vector again into the host cell, and repeating the above procedures as a cycle once or several times.

Ribosomal display is a technique for synthesizing in a test tube a molecule in which a desired protein, an mRNA corresponding to it and a ribosome are associated, for example, by using an mRNA encoding the desired protein without a termination codon, and a cell-free protein synthesis system. A library presenting a group of random mutated proteins on ribosomes can be obtained by using an mRNA group obtained by inducing random mutation in a nucleotide sequence encoding an amino acid sequence of a certain protein, and a cell-free protein synthesis system (Mattheakis L C, et al. (1994) Proc. Natl. Acad. Sci. U.S.A. Vol. 91, No. 19, pp. 9022-9029).

Nucleic acid display is also called mRNA display, and is a technique for synthesizing, for example, a molecule in which a desired protein, an mRNA encoding it and a ribosome are associated, by using a linker such as puromycin having a structure similar to the 3' end of tyrosyl t-RNA. Since this technique uses a cell-free protein synthesis system, not living cells, it is possible to perform the synthesis in vitro. A library presenting a group of random mutated proteins on ribosomes can be obtained by using an mRNA group obtained by inducing random mutation in a nucleotide sequence encoding an amino acid sequence of a certain protein, a linker such as puromycin, and a cell-free protein synthesis system (Nemoto N, et al. (1997) FEBS Lett. Vol. 414, No. 2, pp. 405-408).

A library expressing peptides obtained via a cell-free synthesis system such as ribosome display or nucleic acid display can be incubated in the presence of the target molecule or contacted with the target molecule. For example, a carrier on which MMP-9 is immobilized on a plate is incubated with a mobile phase containing a library for a certain period of time, then the mobile phase is separated from the carrier, and then the carrier is washed to remove non-specific, adsorption or binding substances, thus the peptide, the peptide assembly or the concentrated peptide assembly bound to the carrier (or MMP-9 bound to the carrier) can be recovered by elution. Elution can be performed non-selectively under relatively high ionic strength, low pH, moderate denaturing conditions, the presence of chaotropic salts, or the like, or performed selectively by adding a soluble target molecule such as MMP-9, an antibody bound to the target molecule, a naturally occurring ligand, a substrate or the like to compete with the target molecule immobilized on a plate. Non-specific, adsorption sites and/or binding sites can be subjected to, for example, blocking treatment, and a blocking step by an appropriate method may be incorporated.

The nucleic acid expressing the peptide, the peptide assembly or the concentrated peptide assembly thus obtained is recovered, and, after a reverse transcription reaction to cDNA in the case of mRNA, the nucleotide sequence is sequenced, then the amino acid sequence encoded by the nucleotide sequence can be determined. In addition, the peptide assembly that binds to the target molecule can be highly concentrated by transcribing mRNA from the recovered nucleic acid, and repeating the procedures described above as a cycle once to several times.

When an affinity tag is preliminarily conjugated to the peptide, the peptide assembly or the concentrated peptide assembly, the peptide or the peptide assembly can be efficiently purified. For example, when a protease substrate is preliminarily conjugated to a peptide assembly as a tag, the peptide can be eluted by cleaving with protease activity.

By inducing further mutation in the obtained clone or library based on the obtained sequence information and the function of the peptide, it is also possible to obtain a peptide with improved function (such as active MMP-9-binding activity), physical properties (thermal stability, storage stability, or the like), pharmacokinetics (distribution, blood half-life) and the like from the library to which the mutation has been introduced.

An active MMP-9-binding peptide can be identified by determining whether or not the obtained peptide has active MMP-9-binding activity.

The active MMP-9-binding peptide may preferably maintain a conformation including a loop structure consisting of Ser16 to Val30, a β sheet composed of β strand (1) consisting of Cys31 and Gly32 and β strand (2) consisting of Ile57 to Arg59, and an α helix consisting of Glu41 to Gly51, or a loop structure, a β sheet and an α helix similar thereto or at least partially corresponding thereto (or to the positions thereof) contained in the amino acid sequence of the wild-type SPINK2 to the extent that the active MMP-9-binding activity can be effected. It is also possible to identify a more preferred active MMP-9-binding peptide, using the conformation (entire structure or partial structure) as a part of an index.

4. Nucleic Acid Molecule Encoding Active MMP-9-Binding Peptide, Vector Containing the Same, Cells Containing the Same, and Method for Producing Recombinant Active MMP-9-Binding Peptide The present invention also provides a polynucleotide containing a nucleotide sequence encoding an amino acid sequence contained in an active MMP-9-binding peptide (hereinafter referred to as "nucleic acid molecule encoding an active MMP-9-binding peptide"), a recombinant vector to which the gene has been inserted, a cell to which the gene or vector has been introduced (hereinafter referred to as a "cell containing a nucleic acid molecule encoding an active MMP-9-binding peptide"), or a cell producing an active MMP-9-binding peptide (hereinafter referred to as "active MMP-9-binding peptide-producing cell").

Preferred examples of a part of the nucleic acid molecule encoding the active MMP-9-binding peptide of the present invention include one having the nucleotide sequence described in any one of the following (a) to (d) (hereinafter referred to as "nucleotide sequence of active MMP-9-binding peptide"), one having a nucleotide sequence containing a nucleotide sequence encoding an active MMP-9-binding peptide, and one having a nucleotide sequence encoding an active MMP-9-binding peptide:

(a) a nucleotide sequence encoding the amino acid sequence represented by any one of SEQ ID NOs: 2 to 17 (FIGS. 16 to 31);

(b) a nucleotide sequence that hybridizes with a nucleotide sequence complementary to the nucleotide sequence described in (a) under stringent conditions, and encodes an amino acid sequence contained in a peptide having active MMP-9-binding activity;

(c) a nucleotide sequence having 1 to 20, 1 to 15, 1 to 10, 1 to 8, 1 to 6, 1 to 5, 1 to 4, 1 to 3, 1 to 2, or 1 nucleotide or nucleotide residue substitutions, deletions, additions and/or insertions in the nucleotide sequence described in (a), and encoding an amino acid sequence contained in a peptide having active MMP-9-binding activity; and (d) a nucleotide sequence that is 60%, 70%, 80%, 85%, 90%, 92%, 94%, 96%, 97%, 98%, or 99% or more identical to the nucleotide sequence described in (a), and encoding an amino acid sequence contained in a peptide having active MMP-9-binding activity.

The SPINK2 mutant peptide consisting of or containing the amino acid sequence encoded by the nucleotide sequence described in any one of (a) to (d) above preferably does not bind to pro-MMP-9, and more preferably inhibits protease activity of MMP-9, and even more preferably specifically inhibits protease activity of MMP-9.

However, the nucleic acid molecule encoding the active MMP-9-binding peptide is not limited to (a) to (d), and the nucleic acid molecule containing the nucleotide sequence encoding an amino acid sequence contained in the SPINK2 mutant having active MMP-9-binding activity, preferably the amino acid sequence represented by SEQ ID NO: 18 (FIG. 32), is generally encompassed within the scope of the nucleic acid molecule encoding the active MMP-9-binding peptide.

To design a nucleotide sequence encoding an amino acid sequence, one or two or more codons corresponding to each amino acid may be used. Thus, the nucleotide sequence encoding a single amino acid sequence contained in a certain peptide can have a plurality of variations. In selecting such codons, the codon can be appropriately selected according to the codon usage of the host cell for expression to which a polynucleotide having the nucleotide sequence or a vector containing the same can be introduced, and the frequency or ratio of use of multiple codons can be adjusted appropriately. For example, when *E. coli* is used as a host cell, a nucleotide sequence may be designed using codons that are frequently used in *E. coli*.

A nucleic acid molecule encoding an active MMP-9-binding peptide may be operably linked to one or two or more regulatory sequences. The term "operably linked" means that it can express the linked nucleic acid molecule or allows the expression of the nucleotide sequence contained in the molecule. Regulatory sequences include sequence elements that include information about transcriptional and/or translation regulation. Regulatory sequences vary from species to species, but generally include a promoter, and 5' non-coding sequences involved in transcription and translation initiations, exemplified by a −35/−10 box and a Shine Dalgarno sequence in prokaryotes, and a TATA box, a CAAT sequence, and a 5' capping sequence in eukaryotes. Such sequences may include an enhancer element and/or a repressor element, as well as a signal sequence, a leader sequence, and the like, which may be translated, to deliver native or mature peptides to specific compartments inside or outside of the host cell. Furthermore, regulatory sequences may contain a 3' non-coding sequence, and such a sequence may include elements involved in transcriptional termination, polyadenylation, or the like. Here, if the sequence for transcriptional termination does not function sufficiently in a particular host cell, it can be replaced with a sequence suitable for that cell.

Examples of the promoter sequence include a tet promoter, a lacUV5 promoter, a T7 promoter or the like in prokaryotes, and an SV40 promoter, a CMV promoter or the like in eukaryotic cells.

The nucleic acid molecule encoding an active MMP-9-binding peptide may be, but is not limited to being, in an isolated form or in a form contained in a vector or other cloning vehicle (hereinafter, simply referred to as a "vector": such as a plasmid, phagemid, phage, baculovirus, or cosmid) or a form in a chromosome. The vector may include, in addition to the nucleotide sequence of the active MMP-9-binding peptide and the above regulatory sequences, a replication sequence and a control sequence suitable for the host cell used for expression, as well as a selection marker that provides a cell to which a nucleic acid molecule has been introduced by transformation or the like with a selectable phenotype.

A nucleic acid molecule encoding an active MMP-9-binding peptide and a vector containing the nucleotide sequence of the active MMP-9-binding peptide can be introduced into a host cell capable of expressing the peptide or nucleotide sequence by a method known to those skilled in the art such as transformation. The host cell to which the nucleic acid molecule or vector has been introduced may be cultured under conditions suitable for expression of the peptide or nucleotide sequence. The host cell may be either a prokaryotic cell or a eukaryotic cell. Examples of the prokaryotic cell include *Escherichia coli* and *Bacillus subtilis*. Examples of the eukaryotic cell include yeasts such as *Saccharomyces cerevisiae* and *Pichia pastoris*, insect cells such as SF9 and High5, and animal cells such as HeLa cells, CHO cells, COS cells and NSO. By using the eukaryotic cell or the like as a host cell, the expressed peptide of the present invention can be subjected to desired post-translational modification. Examples of the post-translational modification include addition of functional groups such as a sugar chain, addition of a peptide or protein, and conversion of amino acid chemical properties. It is also possible to apply desired modifications to the peptide of the present invention artificially. Such modified peptides are also encompassed within the scope of the "peptide" of the present invention.

The present invention also includes a method for producing an active MMP-9-binding peptide. The method includes step 1 of culturing a host cell to which a nucleic acid molecule encoding the active MMP-9-binding peptide or a vector containing a nucleotide sequence of the active MMP-9-binding peptide is introduced or a cell that expresses the active MMP-9-binding peptide; and/or step 2 of recovering the active MMP-9-binding peptide from the culture obtained in step 1. For step 2, a procedure known to those skilled in the art such as fractionation, chromatography, purification or the like can be applied. For example, a purification by affinity chromatography using the antibody of the present invention described later can be applied.

In some embodiments of the present invention, the active MMP-9-binding peptide has an intramolecular disulfide bond. It is sometimes preferred to deliver a peptide having an intramolecular disulfide bond to a cell section having an oxidative redox environment by using a signal sequence or the like. The oxidizing environment can be provided by the periplasm of gram-negative bacteria such as *E. coli*, the extracellular environment of gram-positive bacteria, the endoplasmic reticulum lumen of eukaryotic cells, and the like. Under such circumstances, structural disulfide bond formation can be promoted. It is also possible to produce a peptide having an intramolecular disulfide bond in the cytoplasm of a host cell such as *E. coli*. In that case, the peptide may be obtained directly in a soluble folded state, or may be recovered in an inclusion body, and then reconstituted in vitro. Furthermore, it is also possible to select a host cell having an oxidative intracellular environment, and produce a peptide having an intramolecular disulfide bond in the cytoplasm of the host cell. When the active MMP-9-binding peptide does not have an intramolecular disulfide bond, the peptide can be produced in a cell section having a reductive redox environment, for example, in the cytoplasm of gram-negative bacteria.

The active MMP-9-binding peptide of the present invention can also be manufactured by other methods known to those skilled in the art, such as solid phase peptide synthesis methods including Merryfield or other methods; chemical synthesis methods including organic synthetic chemical peptide synthesis methods using t-butoxycarbonyl (Boc), 9-fluorenylmethoxycarbonyl (Fmoc) or the like; and in vitro translation.

The present invention provides, as some embodiments thereof, an antibody that binds to a SPINK2 mutant peptide having active MMP-9-binding activity, and a functional fragment thereof. The antibody may be either a polyclonal antibody or monoclonal antibody, and the monoclonal antibody is not particularly limited as long as it is immunoglobulin or a derivative thereof. The functional fragment of the antibody is not limited to the extent that it has the antigen-binding activity, i.e., binding activity to the SPINK2 mutant peptide. Examples thereof include both or one of the heavy and light chains, fragments thereof, ones lacking a constant region and/or Fc region, and a conjugate with another protein or a labeling substance. Such antibodies and functional fragments thereof can be prepared by a method known to those skilled in the art, and they are useful for purification of the SPINK2 mutant peptide by affinity chromatography, clinical tests related to a pharmaceutical composition containing the peptide or a use thereof, detection of the peptide in diagnosis or the like, immunoassay, and the like. The antibody of the present invention can be purified by affinity chromatography using the peptide of the present invention to which the antibody binds.

5. Pharmaceutical Composition

The present invention also provides a pharmaceutical composition comprising an active MMP-9-binding peptide or a conjugate thereof. Preferably, the active MMP-9-binding peptide or a conjugate thereof is an MMP-9 inhibitory peptide or a conjugate thereof having MMP-9 inhibitory activity.

The pharmaceutical composition of the present invention is useful for the treatment and/or prevention of various diseases which are elicited or exacerbated by MMP-9 and in which the inhibition or suppression of expression or function of MMP-9 can suppress the elicitation or exacerbation, bring cure, maintain or improve symptoms, avoid secondary diseases, or the like (hereinafter, the diseases are referred to as "diseases related to MMP-9" or "MMP-9 related disease").

Examples of the diseases related to MMP-9 include an inflammatory/autoimmune disease, a neurodegenerative disease, a mental disease, a vascular disease, or a malignant tumor.

Examples of the inflammatory/autoimmune disease include rheumatoid arthritis, systemic lupus erythematosus, scleroderma, bronchial asthma, interstitial pneumonia, chronic obstructive pulmonary disease, ulcerative colitis, Crohn's disease, hepatitis, eczema (or dermatitis), psoriasis, lichen planus, erythema/erythroderma, hives, alopecia, pemphigus, acne vulgaris, pressure ulcer/wound, conjunctivitis, keratitis, rhinitis, stomatitis, glossitis, Behcet's disease, multiple sclerosis, encephalitis, headache, peripheral neuritis, diabetic complications (diabetic retinopathy, diabetic nephropathy, diabetic neuropathy), atherosclerosis, pancreatitis, chronic heart failure, and nephritis.

Examples of the neurodegenerative disease include Alzheimer's disease, Parkinson's disease, Huntington's disease, amyotrophic lateral sclerosis, frontotemporal dementia, brain injury, spinal cord injury, hypoxia, convulsion, and traumatic brain disorder.

Examples of the mental disease include major depression, bipolar disorder, anxiety, post-traumatic stress disorder (PTSD), eating disorder, sleep disorder, schizophrenia, addiction, autism, fragile X syndrome, attention deficit hyperactivity disorder, and Down syndrome.

Examples of the vascular disease include cerebrovascular disorder, cerebral aneurysm, cerebral amyloid angiopathy, peripheral vascular disorder, aortic aneurysm, aortic dissection, arteriovenous fistula, arteriosclerosis, Takayasu arteritis, Kawasaki disease, varicose vein, and vascular calcification.

Examples of the malignant tumor include lung cancer, breast cancer, pancreatic cancer, colorectal cancer, and glioma.

However, the diseases related to MMP-9 are not limited to the diseases exemplified herein.

The pharmaceutical composition of the present invention can contain a therapeutically or prophylactically effective amount of the active MMP-9-binding peptide, and a pharmaceutically acceptable diluent, a carrier, a solubilizer, an emulsifier, a preservative and/or an adjuvant.

The term "therapeutically or prophylactically effective amount" means an amount that exerts an effect of treatment or prevention on a particular disease, an administration form or an administration route. The "therapeutically or prophylactically effective amount" has the same meaning as the "pharmacologically effective amount".

The pharmaceutical composition of the present invention can contain a substance for altering, maintaining or retaining pH, osmotic pressure, viscosity, transparency, color, isotonicity, sterility, stability of the composition or peptides or conjugates contained therein, solubility, sustained release, absorptivity, osmotic properties, dosage forms, strengths, properties, shapes, and the like (hereinafter referred to as "substance for formulation"). The substance for formulation is not particularly limited as long as it is pharmacologically acceptable. For example, non-toxicity or low toxicity is a property which the substance for formulation preferably has.

Examples of the substance for formulation include, but are not limited to, amino acids such as glycine, alanine, glutamine, asparagine, histidine, arginine, or lysine; antibacterial agents; antioxidants such as ascorbic acid, sodium sulfate, or sodium bisulfite; buffering agents such as phosphoric acid, citric acid, boric acid buffer, sodium hydrogen carbonate, and Tris-HCl solution; fillers such as mannitol and glycine; chelating agents such as ethylenediaminetetraacetic acid (EDTA); complexing agents such as caffeine, polyvinylpyrrolidine, β-cyclodextrin and hydroxypropyl-β-cyclodextrin; bulking agents such as glucose, mannose, or dextrin; monosaccharides, disaccharides, and other carbohydrates such as glucose, mannose and dextrin; coloring agents; flavoring agents; diluents; emulsifiers; hydrophilic polymers such as polyvinylpyrrolidine; low molecular weight polypeptides; salt-forming counterions; benzalkonium chloride; preservatives such as benzoic acid, salicylic acid, thimerosal, phenethyl alcohol, methylparaben, propylparaben, chlorhexidine, sorbic acid, or hydrogen peroxide; solvents such as glycerin, propylene glycol, or polyethylene glycol; sugar alcohols such as mannitol or sorbitol; suspending agents; PEG; sorbitan esters; polysorbates such as polysorbate 20 or polysorbate 80; surfactants such as triton, tromethamine, lecithin or cholesterol; stabilization enhancers such as sucrose or sorbitol; sodium chloride; potassium chloride; elastic enhancer such as mannitol or sorbitol; transport agents; diluents; excipients; and/or pharmaceutical adjuvants.

The amount of these substances for formulation added is 0.001 to 1000 times, preferably 0.01 to 100 times, more preferably 0.1 to 10 times the weight of the active MMP-9-binding peptide.

The pharmaceutical composition containing an active MMP-9-binding peptide in a liposome or the pharmaceutical composition containing a modified product of an active MMP-9-binding peptide linked to a liposome is also included in the pharmaceutical composition of the present invention.

The excipient and carrier are usually liquid or solid, and are not particularly limited as long as they are substances used for oral or parenteral administration such as water for injection, physiological saline, artificial cerebrospinal fluid and like others. Examples of the physiological saline include ones which are neutral and ones containing serum albumin.

Examples of the buffer include a Tris buffer prepared so that the final pH of the pharmaceutical composition is set to be 7.0 to 8.5, an acetate buffer prepared similarly to be 4.0 to 5.5, a citrate buffer prepared similarly to be 5.0 to 8.0, and a histidine buffer prepared similarly to be 5.0 to 8.0.

The pharmaceutical composition of the present invention is a solid, a liquid, a suspension, or the like. Other examples of the pharmaceutical composition of the present invention include a lyophilized formulation. An excipient such as sucrose can be used to form the lyophilized formulation.

The administration route of the pharmaceutical compositions of the present invention may be any of eye dropping, enteral administration, topical administration, and parenteral administration, and specific examples of them include eye dropping on the conjunctiva, intravitreal administration, intravenous administration, intraarterial administration, intramuscular administration, intradermal administration, subcutaneous administration, intraperitoneal administration, transdermal administration, intraosseous administration, and intraarticular administration.

The composition of such a pharmaceutical composition can be determined according to the method of administration, the active MMP-9-binding affinity or the MMP-9 inhibitory activity of the active MMP-9-binding peptide, and the like. The higher the affinity of the active MMP-9-binding peptide of the present invention for the active MMP-9 protein (the lower the $K_D$ value, $IC_{50}$ value or $K_i$ value), the lower the dosage to exert its drug effect.

The dose of the active MMP-9-binding peptide of the present invention is not limited as long as it is a pharmacologically effective amount, and it can be appropriately determined according to factors such as the species of the individual, the type of disease, symptoms, sex, age, chronic disease, MMP-9 protein binding affinity or the biological activity of the peptide, and the like. However, usually, 0.01 to 1000 mg/kg, preferably 0.1 to 100 mg/kg of the active MMP-9-binding peptide may be administered once, twice or three or more times a day for 1 to 180 days.

Example s of the form of the pharmaceutical compositions include injectables (including lyophilized formulations and drops), suppositories, transnasal absorption formulations, transdermal absorption formulations, sublingual agents, capsules, tablets, ointments, granules, aerosols, pills, powders, suspensions, emulsions, eye drops, and bio embedded formulations.

A pharmaceutical composition containing the active MMP-9-binding peptide as an active ingredient can be administered simultaneously with or separately from an additional pharmaceutical. For example, a pharmaceutical composition containing the active MMP-9-binding peptide as an active ingredient is administered after administering the additional pharmaceutical, or before administering the additional pharmaceutical, or the pharmaceutical composition and the additional pharmaceutical may be administered simultaneously after administering such pharmaceutical composition. When administered simultaneously, the active MMP-9-binding peptide and the additional pharmaceutical may be contained in either a single preparation or separate preparations (multiple preparations).

One or two or three or more additional pharmaceuticals may be administered or received. These are collectively referred to as the "combination use with an additional pharmaceutical" or "combination with an additional pharmaceutical" of the pharmaceutical composition of the present invention. The pharmaceutical composition of the present invention containing an additional pharmaceutical or used in combination with an additional pharmaceutical in addition to the peptide of the present invention or a conjugate thereof is also included in the present invention as an embodiment of the "combination use with an additional pharmaceutical" or "combination with an additional pharmaceutical".

The present invention provides a method for treating or preventing diseases related to MMP-9, including a step of administering an active MMP-9-binding peptide; a use of the active MMP-9-binding peptide of the present invention for preparing a pharmaceutical composition for treating or preventing the disease; and a use of an active MMP-9-binding peptide for treatment or prevention of the disease. A kit for treatment or prevention, containing the active MMP-9-binding peptide of the present invention is also included in the present invention.

Furthermore, the present invention provides a polynucleotide containing a nucleotide sequence encoding an amino acid sequence contained in the active MMP-9-binding peptide of the present invention or a conjugate thereof; a vector containing the polynucleotide; a pharmaceutical composition containing a cell containing the polynucleotide or the vector or expressing the active MMP-9-binding peptide of the present invention or a conjugate thereof. For example, such a polynucleotide and vector can be applied to a gene therapy for diseases related to MMP-9, and such a cell can be applied to a cell therapy for diseases related to MMP-9, respectively using known techniques. Furthermore, it is possible to prepare a cell for a cell therapy, for example, by introducing such a polynucleotide or vector into an autologous cell or allogeneic cell (cell of the same species). Such a polynucleotide and vector are also encompassed by the present invention as a composition for the preparation of cellular therapeutics. However, the embodiments of a pharmaceutical composition containing the polynucleotide, vector, or cell of the present invention are not limited to the above.

6. Diagnostic Composition

The present invention also provides a composition for testing or diagnosis (hereinafter, collectively referred to as a "diagnostic composition") containing the active MMP-9-binding peptide of the present invention or a conjugate thereof.

The diagnostic composition of the present invention is useful for testing or diagnosis for diseases related to MMP-9 such as an inflammatory disease or vascular disease, and MMP-9 expression. Examples of the testing or diagnosis in the present invention include, but are not limited to, determination or measurement of morbidity risk, determination of the presence or absence of morbidity, measurement of the degree of progression or deterioration, measurement or determination of the effect of drug treatment with a pharmaceutical composition such as an MMP-9 inhibitor, measurement or determination of the effect of treatment other than drug treatment, measurement of recurrence risk, and determination of whether the recurrence has occurred or not.

The diagnostic composition of the present invention is useful for identifying an individual to which the peptide of the present invention or a conjugate thereof, a composition containing them, or a pharmaceutical composition containing them is to be administered.

Such a diagnostic composition can contain a pH buffer, an osmotic adjustment agent, salts, a stabilizer, a preservative, a colorant, a sensitizer, an anti-aggregation agent, and the like.

The present invention also provides a method for testing or diagnosing diseases related to MMP-9 such as an inflammatory disease or a vascular disease, a use of the peptide of the present invention for preparing a diagnostic composition for the disease, a use of the peptide of the present invention for testing or diagnosing the disease. A kit for testing or diagnosis containing the peptide of the present invention is also included in the present invention.

The test or diagnostic method using the peptide of the present invention is preferably performed with sandwich ELISA, but can also be performed with normal ELISA method, RIA method, Enzyme-Linked ImmunoSpot (ELISPOT) method, dot blot method, octalony method, counter-immunoelectrophoresis (CIE) method, chemiluminescent immuno assay (CLIA), flow cytometry (FCM), and like other detection methods. For detection, an antibody, or ones obtained by labeling the peptide of the present invention or a conjugate thereof can be used. As the labeling means, biotin, as well as other labeling means that can be used for biochemical analysis, such as HRP, alkaline phosphatase, FITC, and other fluorophores, a label of radioisotope or the like can be used. For detection using an enzyme label, chromogenic substrates such as TMB (3,3',5,5'-tetramethylbenzidine), BCIP (5-bromo-4-chloro-3-indolyl phosphate), ρ-NPP (p-nitrophenyl phosphate), OPD (o-phenylenediamine), ABTS (3-ethylbenzothiazoline-6-sulfonic acid), and SuperSignal ELISA Pico Chemiluminescent Substrate (Thermo Fisher Scientific); fluorogenic substrates such as QuantaBlu™ Fluorogenic Peroxidase Substrate (Thermo Fisher Scientific); as well as other chemiluminescent substrates can be used. Samples derived from human or non-human animals as well as artificially processed samples such as recombinant proteins can be subjected to the measurement. Examples of biological test samples derived from human or non-human animals include, but are not limited to, blood, joint fluid, ascites, lymph fluid, cerebrospinal fluid, alveolar lavage fluid, saliva, sputum, tissue homogenate supernatant, and tissue section.

A sandwich ELISA kit for test or diagnosis containing the peptide of the present invention may contain a standard solution of active MMP-9 protein, a coloring reagent, a dilution buffer, a protein for solid phase, a protein for detection, and a washing solution. As a method for measuring the amount of protein bound to an antigen, an absorbance method, a fluorescence method, a luminescence method, a radioisotope (RI) method and the like can suitably be used. For measurements, an absorbance plate reader, a fluorescence plate reader, a luminescence plate reader, an RI liquid scintillation counter and the like can suitably be used.

The test or diagnosis can also be performed with a method using an immunoprecipitation method.

The present invention also provides a method for detecting or measuring active MMP-9 in a test sample. In the method for detecting or measuring, the diagnostic composition of the present invention can be used. The active MMP-9 in a sample can be detected by step 1 of contacting an active MMP-9-binding peptide or a conjugate thereof with a test sample, and subsequently, step 2 of measuring the amount of, or detection of, MMP-9 bound to the active MMP-9-binding peptide. Step 1 may include, for example, immobilizing an active MMP-9-binding peptide conjugated with an Fc region of an immunoglobulin to magnetic beads via Protein G, and adding a test sample thereto. Step 2 may include, for example, separating the magnetic beads, analyzing the soluble protein precipitated together with the beads by SDS-PAGE or a Western blot method, and detecting the active MMP-9. Samples from human or non-human animals as well as artificially processed samples, such as recombinant proteins can be subjected to the measurement. Examples of biological test samples derived from human or non-human animals include, but are not limited to, blood, joint fluid, ascites, lymph fluid, cerebrospinal fluid, alveolar lavage fluid, saliva, sputum, tissue homogenate supernatant, and tissue section.

Active MMP-9 detection can be performed not only in vitro but also in vivo. When image diagnosis is used, an active MMP-9-binding peptide or a conjugate thereof labeled with a pharmaceutically acceptable radionuclide or illuminant can be used. Step 1 may include, for example, administering to a subject the peptide with a label or a conjugate thereof. Furthermore, step 2 may include, for example, taking an image using an image diagnostic technique such as PET/CT, and determining or examining the presence of active MMP-9.

The peptide or a conjugate thereof contained in the diagnostic composition of the present invention binds to active MMP-9, and preferably has active MMP-9-specific binding activity, in other words, does not bind to pro-MMP-9.

A method of identifying an individual to whom a pharmaceutical composition of the present invention may be administered is also encompassed by the present invention. In the identification method, the active MMP-9 in a sample derived from the individual is measured, and when the active MMP-9 is detected in the sample, or the amount of the active MMP-9 detected in the sample is more than that in a sample derived from a healthy individual, the individual can be determined to be positive. The diagnostic composition of the present invention can be used in the identification method.

In a preferred embodiment of the identification method, the individual suffers from, or is at risk of, MMP-9 related disease.

Furthermore, in one embodiment thereof, the pharmaceutical composition of the present invention can be administered to an individual who has been determined to be positive in the identification method.

7. Method for Separating Active MMP-9

The active MMP-9-binding peptide of the present invention has active MMP-9-specific binding activity, and preferably does not have pro-MMP-9-binding activity. Thus, with the preferred active MMP-9-binding peptide of the present invention or a conjugate thereof, it is possible to separate the active MMP-9 specifically from a sample in which pro-MMP-9 and active MMP-9 are co-existent. The release of the active MMP-9 from the peptide can be carried out non-selectively under conditions such as relatively high ionic strength, low pH, moderate denaturation, the presence of chaotropic salts, or the like, but it is preferred that the release is carried out under conditions such that protease activity of the active MMP-9 is not attenuated.

8. Method for Identifying Therapeutic or Preventive Agent for MMP-9 Related Disease The present invention provides, in one embodiment, a method for identifying an MMP-9 inhibitory compound, a therapeutic or preventive agent for MMP-9 related disease, or a candidate thereof, using an MMP-9 inhibitory activity as an index. The method may include step (i) of incubating MMP-9 protease and a substrate in the presence or absence of a test compound (or in the presence of a vehicle), step (ii) of determining MMP-9 protease activity in the presence and absence of the test compound, and step (iii) of, when the MMP-9 protease activity in the presence of the test compound is small compared to the MMP-9 protease activity in the absence of the test compound, determining that the test compound is positive. In another embodiment, the method for identifying an MMP-9 specific inhibitory compound of the present invention may include step (i) of causing a test compound to bind to human active MMP-9 in the presence of the MMP-9 specific inhibitory SPINK2 mutant peptide of the present invention, preferably a peptide having any one of the amino acid sequences represented by SEQ ID NOs: 2 to 17 (FIGS. 16 to 31), step (ii) of determining whether the test compound competes with the peptide for binding to the human active MMP-9, and optionally step (iii) of determining whether the test compound has human MMP-9 specific binding activity. The test compound in the identification method may be either peptidic or non-peptidic. The peptidic compound is not limited to a SPINK2 mutant, and examples of the peptidic compound include an antibody, an antigen-binding fragment of the antibody, antigen-binding protein, a peptide other than a SPINK2 mutant having a backbone of protein that is not immunoglobulin, and an MMP-9 substrate analog. However, preferred peptidic compounds are SPINK2 mutant peptides. Examples of the non-peptidic compounds include, but are not limited to, synthetic small molecule compounds and nucleic acids. The MMP-9 used in such a method is preferably human MMP-9.

EXAMPLES

In the following examples, some embodiments of the present invention are further described in detail, but the present invention is not limited thereto.

It should be noted that, in the Examples below, respective procedures related to genetic manipulation were performed, unless otherwise indicated, in accordance with the methods described in "Molecular Cloning" (Sambrook, J., Fritsch, E. F. and Maniatis, T., published in 1982 or 1989 from Cold Spring Harbor Laboratory Press) and the methods described in other experimental protocol textbooks used by those skilled in the art, or, when using commercial reagents or kits, the procedures were performed in accordance with the instructions of the commercial products.

Example 1. Preparation of Active MMP-9-Binding Peptide (1-1) Construction of Active MMP-9-Binding Peptide Expression Vector pET 32a(Modified)_Active MMP-9-Binding Peptide First, an expression vector for an active MMP-9-binding peptide having a backbone of SPINK2 scaffold was constructed. Using the nucleotide sequences encoding the amino acid sequences of respective binding peptides (SEQ ID NOs: 2 to 9) and the nucleotide sequence encoding the amino acid sequence of SPINK2 (SEQ ID NO: 1) as templates, the fragments of the binding peptides were amplified by a PCR method ((94° C., 15 seconds; 60° C., 30 seconds; 68° C., 30 seconds)×30 cycles) using the following primers and KOD-plus-(Toyobo Co., Ltd.).

```
Primer 1:
5'-AAAAGAATTCTGATCCGCAGTTTGGTCTGTTTAG-3'

Primer 2:
5'-AAAACTCGAGTTATGCGGCCGCAGACGCGCCGCACGGACC-3'
```

The amplified fragments were subjected to agarose gel electrophoresis, then the desired DNA fragment was excised, and the DNA was prepared by QIAquick Gel Extraction Kit (QIAGEN). The prepared DNA fragments and pET 32a(modified) were treated with restriction enzymes EcoRI (New England Biolabs, Inc.) and XhoI (New England Biolabs, Inc.) at 37° C. for 1 hour or more. After the agarose gel electrophoresis, the desired DNA fragments were excised, and purified by QIAquick PCR Purification Kit (QIAGEN). The purified fragments were reacted with T4 DNA Ligase (New England Biolabs, Inc.) at 16° C. overnight to carry out a ligation reaction. The ligation solution was added to E. coli JM109 (Toyobo Co., Ltd.) and allowed to stand on ice for 30 minutes. The resulting solution was then subjected to heat treatment of 42° C. for 45 seconds, and allowed to stand on ice for 5 minutes, then seeded on a 2YT plate containing 0.1 mg/ml ampicillin, and then subjected to static culture at 37° C. overnight to transform E. coli. The next day, the transformed E. coli was inoculated into Terrific broth medium (Thermo Fisher Scientific) containing 0.1 mg/ml ampicillin, and cultured at 37° C. overnight. Then, plasmid DNA was recovered using QIAprep 96 Turbo Miniprep Kit (QIAGEN) (hereinafter referred to as "miniprep treatment"), and sequence analysis was performed to construct "pET 32a(modified)_active MMP-9-binding peptide".

(1-2) Expression and Purification of Active MMP-9-Binding Peptide

The vector pET 32a(modified)_active MMP-9-binding peptide constructed in (1-1) was transformed to E. coli Origami B (DE3) (Merck & Co., Inc.), and the transformed E. coli was cultured at 37° C. using 2YT medium containing 0.1 mg/ml ampicillin. IPTG (final concentration of 1 mM) was then added, and the mixture was cultured at 16° C. overnight. The next day, the cells were recovered by centrifugation (3,000 g, 20 minutes, 4° C.), then the lysate was prepared using BugBuster Master Mix (Merck & Co., Inc.), and the target protein fused with a His tag was purified using TALON Metal Affinity Resin (Clontech Laboratories, Inc.). Next, the target protein was cleaved from the thioredoxin tag using Thrombin Cleavage Capture Kit (Merck & Co., Inc.), then subjected to purification with TALON. Furthermore, the purified product was subjected to gel filtration chromatography (Superdex 75 10/300 GL) or reverse phase chromatography (YMC-Pack ODS-AM) to prepare an active MMP-9-binding peptide. In the obtained peptide, a moiety composed of Stag+linker 1 (SEQ ID NO: 19, FIG. 33) is conjugated at the N-terminal, and a C-terminal 6-mer (SEQ ID NO: 21, FIG. 35) is conjugated at the C-terminal, respectively.

Figure 1A:
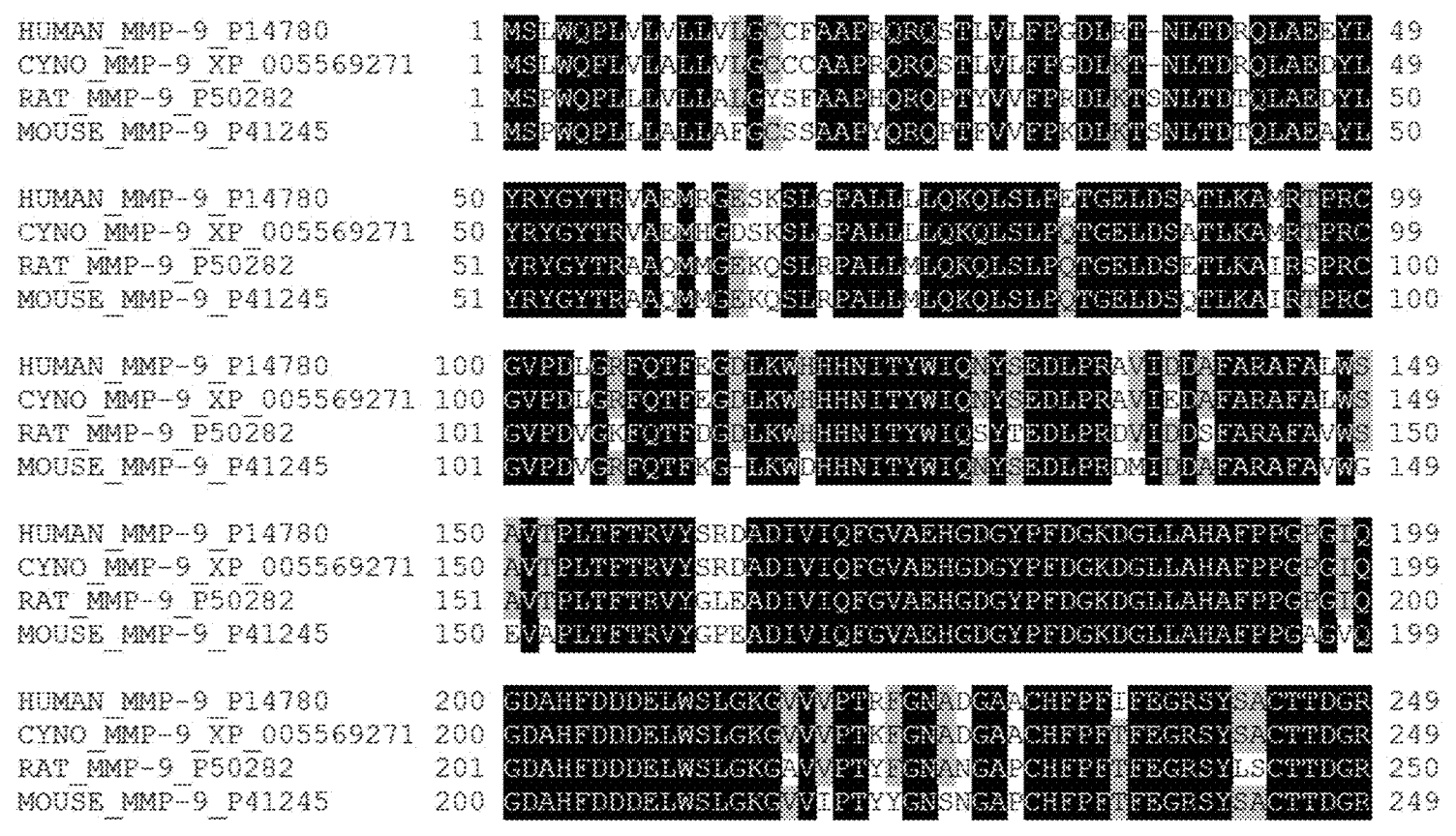

Example 2. Preparation of MMP-9 for Evaluation of Active MMP-9-Binding Peptide FIG. 1 shows sequence similarities of human/monkey/rat/mouse MMP-9.

(2-1) Preparation of Human MMP-9 Enzyme Active Domain hMMP-9(Cat)

(2-1-1) Construction of pCMA-Pro-hMMP-9(Cat)_His6

A fragment of about 5.4 kb obtained by digesting plasmid pcDNA 3.3-TOPO/LacZ (Thermo Fisher Scientific) with restriction enzymes XbaI (New England Biolabs, Inc.) and PmeI (New England Biolabs, Inc.) was ligated with a DNA fragment containing a nucleotide sequence encoding a human MMP-9 (P14780) represented by SEQ ID NO: 28 (FIG. 44), using an In-Fusion HD Cloning Kit (Clontech Laboratories, Inc.) to produce pcDNA3.3-hMMP-9. PCR was performed using pcDNA3.3-hMMP-9 as a template and the primers described below, then the obtained fragment of about 5.5 kb was phosphorylated, and then self-ligated to construct pCMA-hMMP-9 having a nucleotide sequence encoding human MMP-9 represented by SEQ ID NO: 28 (FIG. 44) at the downstream of a CMV promoter.

```
Primer 3:
5'-TATACCGTCGACCTCTAGCTAGAGCTTGGC-3'

Primer 4:
5'-GCTATGGCAGGGCCTGCCGCCCCGACGTTG-3'
```

PCR was performed using pCMA-hMMP-9 as a template, and pCMA-pro-hMMP-9(cat)_His6 having, at the downstream of the CMV promoter, a nucleotide sequence encoding a secretion signal (Met1-Ala19) of human MMP-9 (SEQ ID NO: 28 (FIG. 44)), a propeptide (Ala20-Arg106), an enzyme active domain (Phe107-Pro449) and a His tag was constructed.

(2-1-2) Construction of pCMA-Pro-hMMP-9(Cat)_His6_FLAG_Avi

PCR was performed using pCMA-hMMP-9 as a template, and pCMA-pro-hMMP-9(cat)_His6_FLAG_Avi having, at the downstream of the CMV promoter, a nucleotide sequence encoding a secretion signal (Met1-Ala19) of human MMP-9 (SEQ ID NO: 28 (FIG. 44)), a His tag, a propeptide (Ala20-Arg106), an enzyme active domain (Phe107-Pro449), a FLAG tag (DYKDDDDK: FIG. 50: SEQ ID NO: 34)) and an Avi tag (GGGLNDIFEAQK-IEWHE: FIG. 51, SEQ ID NO: 35) was constructed.

(2-1-3) Preparation of Pro-hMMP-9(Cat)_His6

The pCMA-pro-hMMP-9(cat)_His6 constructed in (2-1-1) was transfected into FreeStyle 293F (Thermo Fisher Scientific) using Polyethyleneimine Max (Polysciences, Inc.), and six days later, the culture supernatant was recovered. The His tag fusion protein was recovered by HisTrap excel (GE Healthcare), and the buffer solution was replaced with PBS to purify pro-hMMP-9(cat)_His6.

(2-1-4) Preparation of Active hMMP-9(Cat)_His6

The pro-hMMP-9(cat)_His6 obtained in (2-1-3) and hMMP-3 activated with APMA were mixed, and reacted at 37° C. for 4 hours. The reaction solution was replaced with PBS at low temperature to purify active hMMP-9(cat)_His6.

(2-1-5) Preparation of Pro-hMMP-9(Cat)_His6_FLAG_Avi

In the same way as in (2-1-3), pCMA-pro-hMMP-9(cat)_His6_FLAG_Avi constructed in (2-1-2) was used, and pro-hMMP-9(cat)_His6_FLAG_Avi was purified.

(2-1-6) Preparation of Biotin-Labelled Pro-hMMP-9(Cat)_His6_FLAG_Avi

The pro-hMMP-9(cat)_His6_FLAG_Avi obtained in (2-1-5) was replaced with 10 mM Tris-HCl, pH 8.0, and then labeled with biotin at 30° C. for 1 hour according to the protocol of biotin ligase BirA (Avidity, LLC). The reaction solution was replaced with PBS at low temperature, and biotin-labeled pro-hMMP-9(cat)_His6_FLAG_Avi was purified.

(2-1-7) Preparation of Biotin-Labeled Active hMMP-9(Cat)_FLAG_Avi

In the same way as in (2-1-4), the biotin-labelled pro-hMMP-9(cat)_His6_FLAG_Avi obtained in (2-1-6) was activated, and biotin-labeled active hMMP-9(cat)_FLAG_Avi was purified.

(2-2) Preparation of Mouse MMP-9 Enzyme Active Domain mMMP-9(Cat)

(2-2-1) Construction of pCMA-Pro-mMMP-9(Cat)_His6_FLAG_Avi

A fragment of about 5.4 kb obtained by digesting plasmid pcDNA 3.3-TOPO/LacZ (Thermo Fisher Scientific) with restriction enzymes XbaI and PmeI was ligated with a DNA fragment containing a nucleotide sequence encoding mouse MMP-9 (P41245) represented by SEQ ID NO: 29 (FIG. 45) using an In-Fusion HD Cloning Kit (Clontech Laboratories, Inc.) to produce pcDNA3.3-mMMP-9. PCR was performed using the following primers and pcDNA3.3-mMMP-9 as a template. The obtained fragment of approximately 5.6 kb was phosphorylated, then self-ligated to construct pCMA-mMMP-9 having, downstream of the CMV promoter, a nucleotide sequence encoding mouse MMP-9 represented by SEQ ID NO: 29 (FIG. 45).

```
Primer 3:
5'-TATACCGTCGACCTCTAGCTAGAGCTTGGC-3'

Primer 4:
5'-GCTATGGCAGGGCCTGCCGCCCCGACGTTG-3'
```

PCR was performed using pCMA-mMMP-9 as a template, and pCMA-pro-mMMP-9(cat)_His6_FLAG_Avi having, at the downstream of the CMV promoter, a nucleotide sequence encoding a secretion signal (Met1-Ala19) of mouse MMP-9 (SEQ ID NO: 29 (FIG. 45)), a His tag, a propeptide (Ala20-Arg107), an enzyme active domain (Phe108-Pro449), a FLAG tag (FIG. 50, SEQ ID NO: 34) and an Avi tag (FIG. 51, SEQ ID NO: 35) was constructed.

(2-2-2) Preparation of Pro-mMMP-9(Cat)_His6_FLAG_Avi

In the same way as in (2-1-3), pCMA-pro-mMMP-9(cat)_His6_FLAG_Avi constructed in (2-2-1) was used, and pro-mMMP-9(cat)_His6_FLAG_Avi was purified.

(2-2-3) Preparation of Active mMMP-9(Cat)_FLAG_Avi

In the same way as in (2-1-4), pro-mMMP-9(cat)_His6_FLAG_Avi obtained in (2-2-2) was activated, and active mMMP-9(cat)_FLAG_Avi was purified.

Example 3. Evaluation of MMP-9-Binding Activity of Active MMP-9-Binding Peptide

Figure 2B:
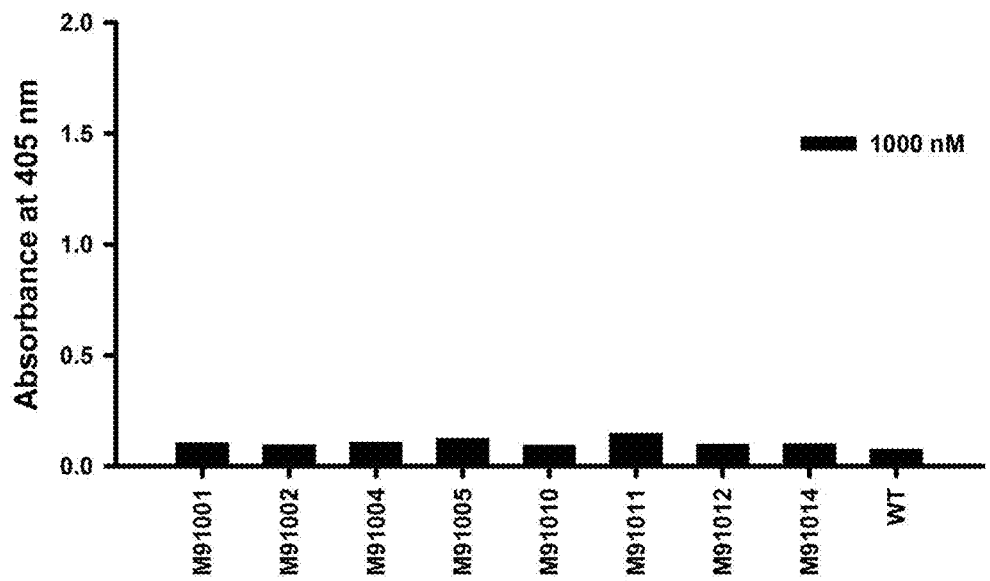
FIG. 2(B) is a graph showing an evaluation of pro human MMP-9-binding activity of each binding peptide or wild type SPINK2 (n=2), using the detection intensity of the tag added to the amino terminal of the active MMP-9-binding peptide as an index.

The biotin-labeled pro-hMMP-9(cat)_His6_FLAG_Avi obtained in (2-1-6) or biotin-labeled active hMMP-9(cat)_FLAG_Avi obtained in (2-1-7) was immobilized on a streptavidin coated 96-well plate (Thermo Fisher Scientific). After blocking with 3% BSA, 1 to 1,000 nM of the binding peptides were added, and reacted at room temperature for 1.5 hours. After washing, goat anti-S-Tag HRP conjugated (Bethyl Laboratories, Inc.) was added, and reacted at room temperature for 1 hour. After washing, substrates of ELISA POD substrate A.B.T.S kit (Nacalai Tesque Inc.) were added, and reacted at room temperature. After adding a reaction stop solution, the absorbance at 405 nm was measured with Enspire (PerkinElmer, Inc.), and MMP-9-binding activity of the active MMP-9-binding peptides was evaluated. By calculating the 50% effective concentration ($EC_{50}$) using GraphPad Prism (version 5.0; GraphPad Software), it was revealed that each of the active MMP-9-binding peptides bind to the active human MMP-9 enzyme active domain at a low concentration, but do not bind to pro human MMP-9 enzyme active domain even at 1 µM (FIGS. 2 and 3). In contrast, wild type SPINK2 (WT) did not bind to either of the active human MMP-9 enzyme active domain or the pro human MMP-9 enzyme active domain (FIG. 2).

Example 4. Evaluation of MMP-9 Inhibitory Activity of Active MMP-9-Binding Peptides (4-1) Evaluation of Human MMP-9 Inhibitory Activity of Active MMP-9-Binding Peptide Using Substrate Peptide The substrate peptide MOCAc—KPLGL-$A_2$pr(Dnp)-AR—$NH_2$ (SEQ ID NO: 30 (FIG. 46)) (PEPTIDE INSTITUTE, INC.; 3226-v) was dissolved in water to 1 mM, and diluted with an assay buffer (50 mM Tris-HCl, 200 mM NaCl, 2 mM $CaCl_2$, pH 7.5) to use at a final concentration of 2.5 to 10 µM. Fifty µl each of the active hMMP-9(cat)_His6 diluted with the assay buffer and the active MMP-9-binding peptide were mixed, and reacted at 37° C. for 1 hour. Then, 100 µl of the substrate diluted with the assay buffer was added, and fluorescence signals (excitation 328 nm/emission 393 nm) were measured with Enspire (PerkinElmer, Inc.). The final concentration of active hMMP-9(cat)_His6 was 0.4 nM, and the final concentration of the active MMP-9-binding peptide was 0.5 to 25 nM. For reactions and measurements, a ProteoSave™ SS96F black plate (Sumitomo Bakelite Co., Ltd.) was used.

Figure 4:
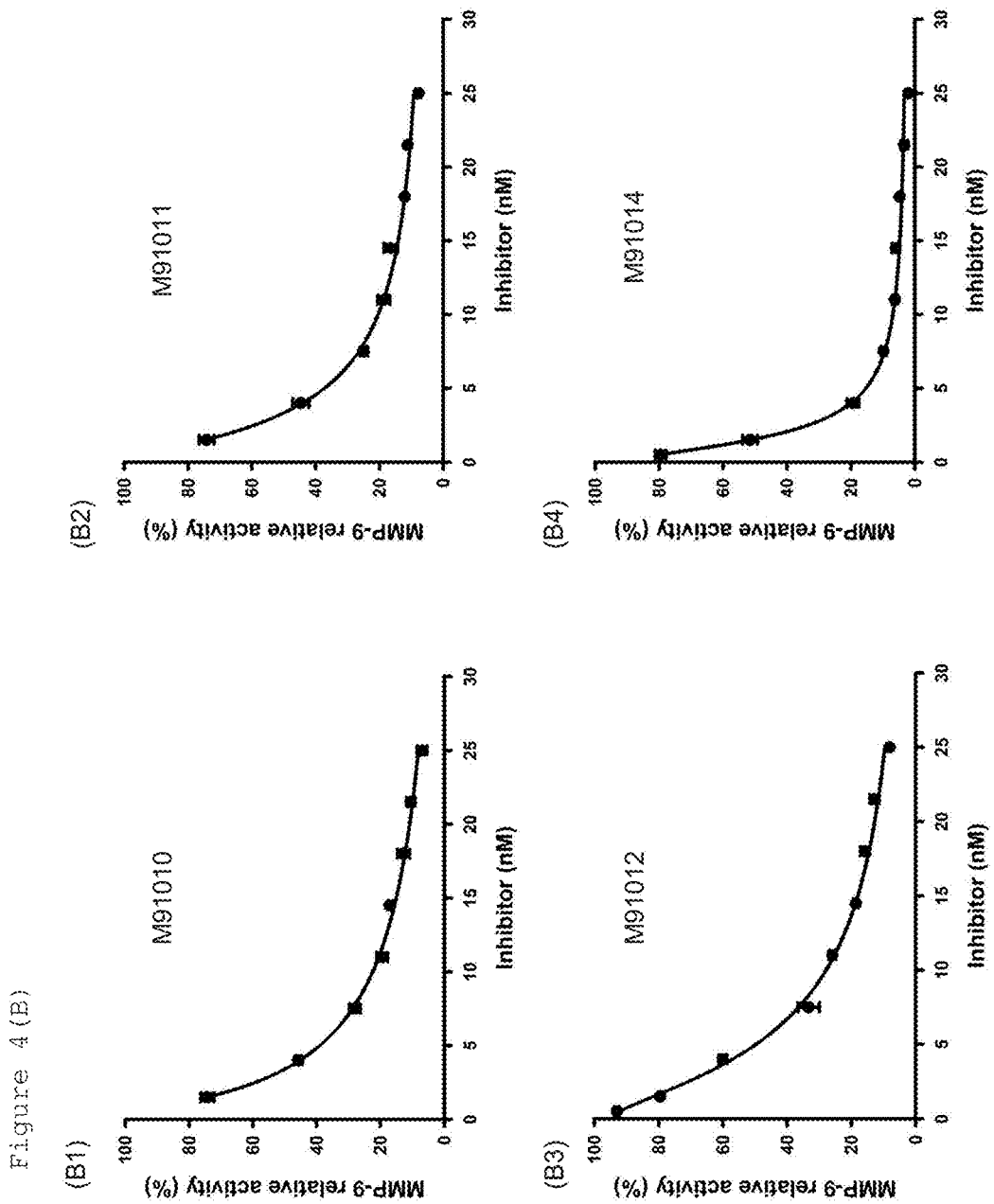
FIG. 4(A) is a graph showing an evaluation of human MMP-9 inhibitory activity of active MMP-9-binding peptides (n=3, Mean±SD), using the degradation rate of the substrate peptide as an index.
FIG. 4(B) is a graph showing an evaluation of human MMP-9 inhibitory activity of active MMP-9-binding peptides (n=3, Mean±SD), using the degradation rate of the substrate peptide as an index (continued).

The substrate peptide degradation rate at each concentration of the active MMP-9-binding peptide was calculated, and the human MMP-9 inhibitory activity of each binding peptide was evaluated by taking the degradation rate at an inhibitor concentration of 0 nM as 100% (FIG. 4). The inhibition constant Ki was calculated according to Morrison's formula using GraphPad Prism (version 5.0; GraphPad Software), and as the result, it was revealed that each of the active MMP-9-binding peptides strongly inhibit human MMP-9 enzyme activity at low concentrations (FIG. 5).

(4-2) Evaluation of Human MMP-9 Inhibitory Activity of Active MMP-9-Binding Peptide Using Substrate Gelatin The substrate gelatin DQ Gelatin from Pig Skin, Fluorescein Conjugate (Thermo Fisher Scientific) was dissolved in water to 1 mg/ml, and diluted with an assay buffer (50 mM Tris-HCl, 200 mM NaCl, 2 mM $CaCl_2$, pH 7.5) to use at a final concentration of 10 µg/ml. Fifty µl each of the active hMMP-9(cat)_His6 diluted with the assay buffer and the active MMP-9-binding peptide were mixed, and reacted at 37° C. for 1 hour. Then, 100 µl of the substrate diluted with the assay buffer was added, and fluorescence signals (excitation 495 nm/emission 515 nm) were measured with Enspire (PerkinElmer, Inc.). The final concentration of the active hMMP-9(cat)_His6 was 0.6 nM, and the final concentration of active MMP-9-binding peptide was 0.002 to 100 nM. For reactions and measurements, a ProteoSave™ SS96F black plate (Sumitomo Bakelite Co., Ltd.) was used.

Figures 5, 6:
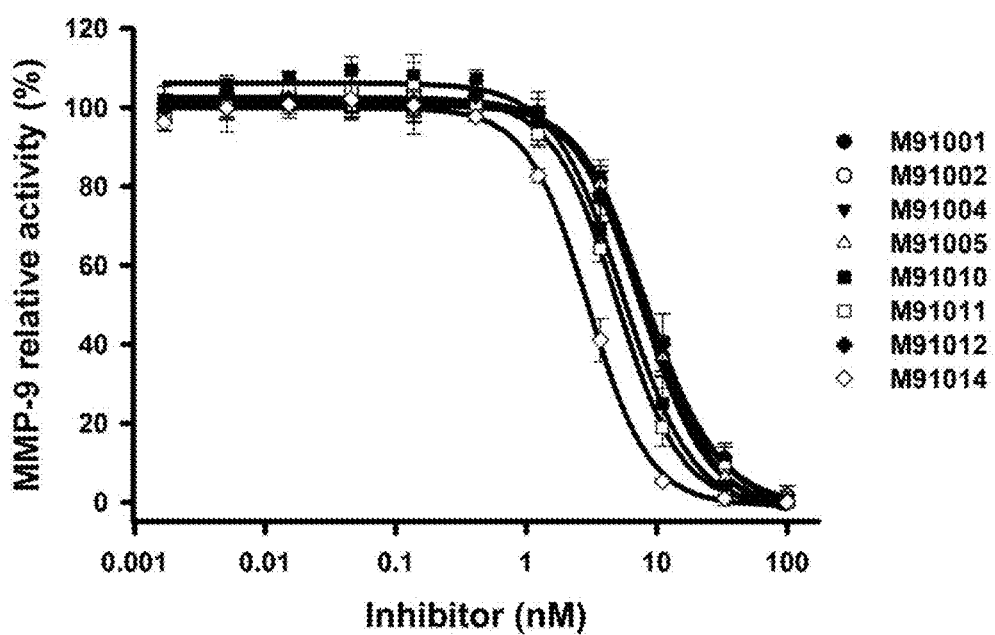
FIG. 5 is a table showing human MMP-9 inhibition constant $K_i$ of active MMP-9-binding peptides (n=3, Mean±SD) when the substrate peptide was used.
FIG. 6 is a graph showing an evaluation of human MMP-9 inhibitory activity of active MMP-9-binding peptides (n=3, Mean±SD), using the degradation rate of the substrate gelatin as an index.

The substrate gelatin degradation rate at each concentration of the active MMP-9-binding peptide was calculated, and the human MMP-9 inhibitory activity of each binding peptide was evaluated by taking the degradation rate at the inhibitor concentration of 0 nM as 100% (FIG. 6). The 50% inhibitory concentration ($IC_{50}$) was calculated using GraphPad Prism (version 5.0; GraphPad Software), and as the result, it was revealed that each of the active MMP-9-binding peptides strongly inhibit human MMP-9 enzyme activity at low concentrations (FIG. 7), as in (4-1), even when gelatin is used as the substrate.

Example 5. Evaluation of Mouse MMP-9 Inhibitory Activity of Active MMP-9-Binding Peptide Using Substrate Peptide The substrate peptide MOCAc—KPLGL-$A_2$pr(Dnp)-AR—$NH_2$ (SEQ ID NO: 30 (FIG. 46)) (PEPTIDE INSTITUTE, INC.; 3226-v) was dissolved in water to 1 mM, and diluted with an assay buffer (50 mM Tris-HCl, 200 mM NaCl, 2 mM $CaCl_2$, pH 7.5) to use at a final concentration of 10 µM. Fifty µl each of the active mMMP-9(cat)_FLAG_Avi diluted with the assay buffer and the active MMP-9-binding peptide were mixed, and reacted at 37° C. for 1 hour. Then, 100 µl of the substrate diluted with the assay buffer was added, and fluorescence signals (excitation 328 nm/emission 393 nm) were measured with Enspire (PerkinElmer, Inc.). The final concentration of active mMMP-9(cat)_FLAG_Avi was 0.4 nM, and the final concentration of active MMP-9-binding peptide was 0.002 to 100 nM. For reactions and measurements, a ProteoSave™ SS96F black plate (Sumitomo Bakelite Co., Ltd.) was used.

Figures 7, 8:
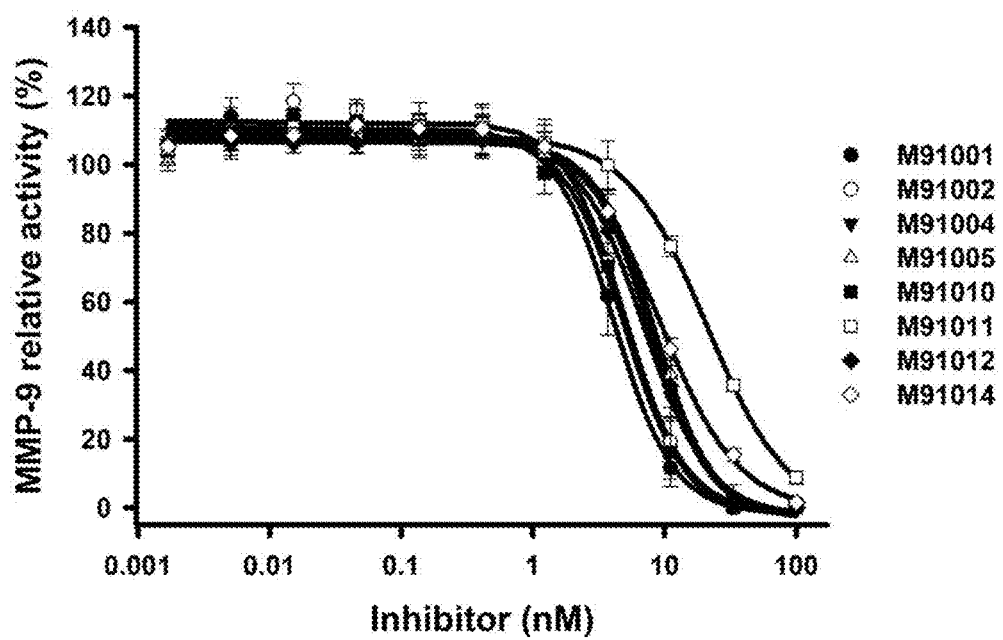
FIG. 7 is a table showing human MMP-9 inhibitory activity $IC_{50}$ of active MMP-9-binding peptides (n=3, Mean±SD) when the substrate gelatin was used.
FIG. 8 is a graph showing an evaluation of mouse MMP-9 inhibitory activity of active MMP-9-binding peptides (n=3, Mean±SD), using the degradation rate of the substrate peptide as an index.

The substrate peptide degradation rate at each concentration of the active MMP-9-binding peptide was calculated, and the mouse MMP-9 inhibitory activity of each binding peptide was evaluated by taking the degradation rate at the inhibitor concentration of 0 nM as 100% (FIG. 8). The 50% inhibitory concentration ($IC_{50}$) was calculated using GraphPad Prism (version 5.0; GraphPad Software), and as the result, it was revealed that each of the active MMP-9-binding peptides strongly inhibit mouse MMP-9 enzyme activity at low concentrations (FIG. 9).

Example 6. Specificity Evaluation of Active MMP-9-Binding Peptide

Specificities for other MMPs or ADAM17 protease were evaluated using the cleavage of the substrate peptide as an index. In the same way as in the method described in (3-1), 50 µl each of the proteases diluted with the assay buffer and a sample (final concentration of 1 µM) were mixed, and the mixtures were reacted at 37° C. for 10 minutes for MMP-13 and MMP-17, and at 37° C. for 60 minutes for other proteases. Then, 100 µl of the substrate diluted with the assay buffer was added, and fluorescence signals (excitation 328 nm/emission 393 nm) were measured with Enspire (PerkinElmer, Inc.). It should be noted that a buffer of 50 mM Tris-HCl, 10 mM $CaCl_2$, pH 7.5 was used as the assay buffer for evaluation of MMP-17 activity, and a buffer of 50 mM Tris-HCl, 200 mM NaCl, 2 mM $CaCl_2$, pH 7.5 was used as the assay buffer for evaluation of activities of proteases other than MMP-17. For reactions and measurements, a ProteoSave™ SS96F black plate (Sumitomo Bakelite Co., Ltd.) was used. The combinations of proteases and substrates used for the specificity evaluation were as follows.

Human MMP-1 inhibitory activity evaluation; 5 nM final concentration of APMA-activated human MMP-1 enzyme active domain (in-house preparation), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-2 inhibitory activity evaluation; 1.4 nM final concentration of MMP-2, active, Human, Recombinant, CHO Cells (Merck & Co., Inc.; PF023), and 50 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-3 inhibitory activity evaluation; 25 nM final concentration of human MMP-3 activated by APMA (in-house preparation), and 10 µM final concentration of substrate peptide MOCAc—RPKPVE-Nva-WR-Lys(Dnp)-$NH_2$ (SEQ ID NO: 33, FIG. 49) (PEPTIDE INSTITUTE, INC.; 3168-v)

Human MMP-7 inhibitory activity evaluation; 1 nM final concentration of MMP-7 (catalytic domain) (human), (recombinant) (Enzo Life Sciences, Inc.; BML-SE 181), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-8 inhibitory activity evaluation; 0.6 nM final concentration of APMA-activated human MMP-8 enzyme active domain (in-house preparation), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-10 inhibitory activity evaluation; 4 nM final concentration of MMP-10 (catalytic domain) (human), (recombinant) (Enzo Life Sciences, Inc.; BML-SE 329), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-12 inhibitory activity evaluation; 4 nM final concentration of MMP-12 (catalytic domain) (human), (recombinant) (Enzo Life Sciences, Inc.; BML-SE 138), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-13 inhibitory activity evaluation; 2 nM final concentration of APMA-activated human MMP-13 enzyme active domain (in-house preparation), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-14 inhibitory activity evaluation; 1 nM final concentration of MMP14 Recombinant Protein (Thermo Fisher Scientific; RP-77531), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-15 inhibitory activity evaluation; 1 nM final concentration of MT2-MMP, Catalytic Domain, Human, Recombinant, E. coli (Merck & Co., Inc.; 475938), and 10 µM final concentration of substrate peptide MOCAc—KPLGL-$A_2$pr(Dnp)-AR—$NH_2$ (SEQ ID NO: 30, FIG. 46) (PEPTIDE INSTITUTE, INC.; 3226-v)

Human MMP-16 inhibitory activity evaluation; 3 nM final concentration of Recombinant Human MMP-16/MT3-MMP Protein, CF (R&D Systems, Inc.; 1785-MP), and 10 µM final concentration of substrate peptide MOCAc—

KPLGL-A$_2$pr(Dnp)-AR—NH$_2$ (SEQ ID NO: 30, FIG. 46) (PEPTIDE INSTITUTE, INC.; 3226-v)

Human MMP-17 inhibitory activity evaluation; 3 nM final concentration of Recombinant Human MMP-17 Protein, CF (R&D Systems, Inc.; 7796-MP), and 10 μM final concentration of substrate peptide MOCAc—KPLGL-A$_2$pr(Dnp)-AR—NH$_2$ (SEQ ID NO: 30, FIG. 46) (PEPTIDE INSTITUTE, INC.; 3226-v)

Human ADAM17 inhibitory activity evaluation; 3 nM final concentration of ADAM17 (catalytic domain) (human), (recombinant) (His-tag) (Enzo Life Sciences, Inc.; BML-SE268), and 10 μM final concentration of substrate peptide MOCAc—KPLGL-A$_2$pr(Dnp)-AR—NH$_2$ (SEQ ID NO: 30, FIG. 46) (PEPTIDE INSTITUTE, INC.; 3226-v)

In the same way as in (4-1), the specificities for other MMPs or ADAM17 protease were evaluated using degradation of the substrate peptide as an index. At the inhibitor final concentration of 1 μM, each binding peptide did not inhibit protease activities of any of the proteases, indicating that the active MMP-9-binding peptide has MMP-9 specific inhibitory action (FIG. 10). In contrast, a non-selective inhibitor sc-311438 (Santa Cruz Biotechnology, Inc.) inhibited all proteases at the final concentration of 1 μM (FIG. 10).

Example 7. Preparation of Active MMP-9-Binding Peptide Derivative (7-1) Construction of Expression Vector of Active MMP-9-Binding Peptide Derivative (7-1-1) Construction of Active MMP-9-Binding Peptide Derivative (C-Terminal Derivative) Expression Vector PCR was performed using the vector pET 32a(modified)_M91002 which was obtained by inserting the active MMP-9-binding peptide M91002 into the vector pET 32a(modified)_active MMP-9-binding peptide constructed in (1-1) as a template, and pET 32a(modified)_M91002_G0 having, downstream of the T7 promoter, a nucleotide sequence encoding a Trx tag, a His tag, Stag+linker 2 (SEQ ID NO: 20, FIG. 34) and M91002 (SEQ ID NO: 3, FIG. 17) was constructed. Next, PCR was performed using the constructed pET 32a(modified)_M91002_G0 as a template, and pET 32a(modified)_M91002_G2 having, downstream of the T7 promoter, a nucleotide sequence encoding a Trx tag, a His tag, Stag+linker 2 (SEQ ID NO: 20, FIG. 34), M91002 (SEQ ID NO: 3, FIG. 17) and a C-terminal 2-mer (Gly-Gly: FIG. 37) was constructed. Then, PCR was performed using the constructed pET 32a(modified)_M91002_G0 as a template, and pET 32a(modified)_M91002_G3 having, downstream of the T7 promoter, a nucleotide sequence encoding a Trx tag, a His tag, Stag+linker 2 (SEQ ID NO: 20, FIG. 34), M91002 (SEQ ID NO: 3, FIG. 17) and a C-terminal 3-mer (Gly-Gly-Gly: FIG. 36) was constructed.

(7-1-2) Construction of Active MMP-9-Binding Peptide Derivative (Fc Conjugate) Expression Vector A DNA fragment obtained by digesting the vector pCMA-hMMP-9 constructed in (2-1-1) with restriction enzymes XbaI (New England Biolabs, Inc.) and PmeI (New England Biolabs, Inc.) to remove a nucleotide sequence encoding human MMP-9, and a DNA fragment containing a nucleotide sequence encoding a human IgG1 heavy chain signal sequence, Stag+linker 1 (SEQ ID NO: 19, FIG. 33), M91005 (SEQ ID NO: 5, FIG. 19), a C-terminal 6-mer (SEQ ID NO: 21, FIG. 35), a G4S linker (SEQ ID NO: 22, FIG. 38) and human IgG1 Fc (SEQ ID NO: 23, FIG. 39) were ligated using an In-Fusion HD Cloning Kit (Clontech Laboratories, Inc.) to produce pCMA-M91005-Fc-01.

(7-1-3) Construction of Active MMP-9-Binding Peptide Derivative (N-Terminal Derivative) Expression Vector PCR was performed using the vector pCMA-M91005-Fc-01 constructed in (7-1-2) as a template, and pCMA-M91005_D1G-Fc-01 having, at the downstream of the CMV promoter, a nucleotide sequence encoding a human IgG1 heavy chain signal sequence, Stag+linker 1 (SEQ ID NO: 19, FIG. 33), M91005_D1G (SEQ ID NO: 13, FIG. 27), a C-terminal 6-mer (SEQ ID NO: 21, FIG. 35), a G4S linker (SEQ ID NO: 22, FIG. 38) and human IgG1 Fc (SEQ ID NO: 23, FIG. 39) was constructed.

(7-2) Expression and Purification of Active MMP-9-Binding Peptide Derivatives

In the same way as in (1-2), the vector pET 32a(modified)_M91002_G0, pET 32a(modified)_M91002_G2 or pET 32a(modified)_M91002_G3 constructed in (7-1-1) was used, and active MMP-9-binding peptide derivatives (C-terminal derivatives) were prepared. In the obtained peptide derivatives, a moiety consisting of Stag+linker 2 (SEQ ID NO: 20, FIG. 34) is conjugated at the N-terminal, while a C-terminal 2-mer (Gly-Gly: FIG. 37) is conjugated at the C-terminal of M91002_G2 and a C-terminal 3-mer (Gly-Gly-Gly: FIG. 36) is conjugated at the C-terminal of M91002_G3, respectively.

The pCMA-M91005-Fc-01 constructed in (7-1-2) or pCMA-M91005_D1G-Fc-01 constructed in (7-1-3) was transfected into FreeStyle 293F (Thermo Fisher Scientific) using Polyethyleneimine Max (Polysciences, Inc.), and six days later, the culture supernatant was recovered. The Fc conjugate protein was recovered by MabSelect SuRe (GE Healthcare), then subjected to gel filtration chromatography (Superdex 200 Increase 10/300 GL) to prepare an active MMP-9-binding peptide derivative (Fc conjugate) or an active MMP-9-binding peptide derivative (N-terminal derivative). In the obtained peptide derivatives, a moiety consisting of Stag+linker 1 (SEQ ID NO: 19, FIG. 33) is conjugated at the N-terminal, while a C-terminal 6-mer (SEQ ID NO: 21, FIG. 35), a G4S linker (SEQ ID NO: 22, FIG. 38) and human IgG1 Fc (SEQ ID NO: 23, FIG. 39) are conjugated at the C-terminal.

Figures 11A, 11B:
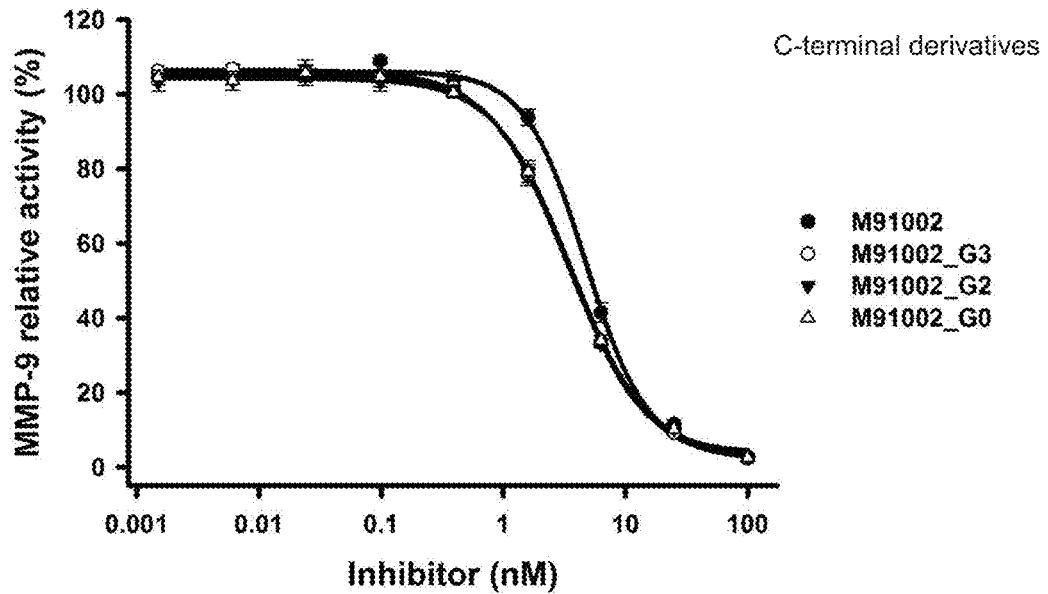
FIG. 11(A) is a graph showing an evaluation of human MMP-9 inhibitory activity of the active MMP-9-binding peptide M91002 and its C-terminal derivatives M91002_G3, M91002_G2 and M91002_G0 (n=3, Mean±SD), using the degradation rate of the substrate peptide as an index.
FIG. 11(B) is a table showing the human MMP-9 inhibitory activity $IC_{50}$ of the active MMP-9-binding peptide M91002 and its C-terminal derivatives M91002_G3, M91002_G2 and M91002_G0 (n=3, Mean±SD) when the substrate peptide was used.
Figures 12A, 12B:
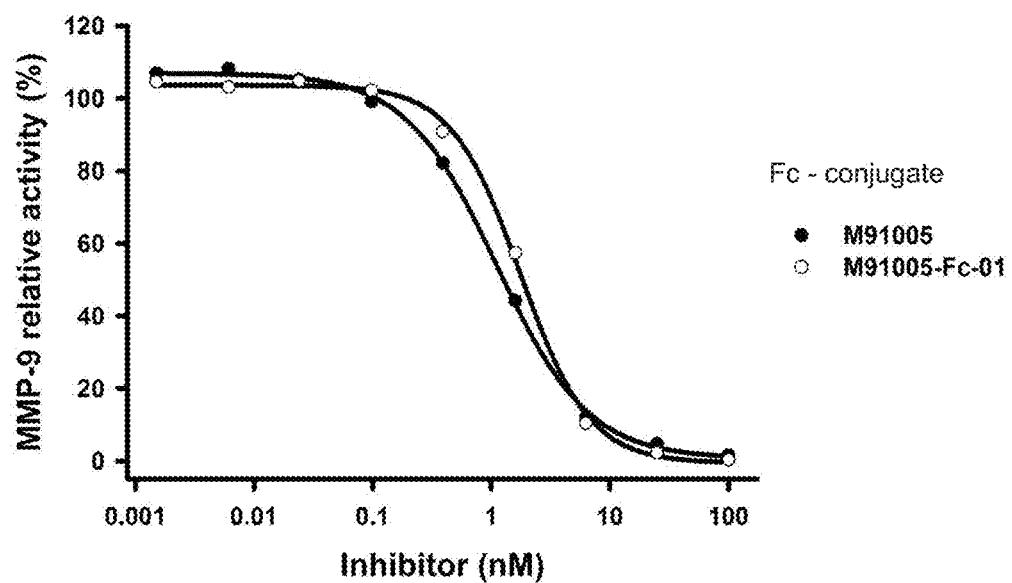
FIG. 12(A) is a graph showing an evaluation of human MMP-9 inhibitory activity of the active MMP-9-binding peptide M91005 and its C-terminal conjugate M91005-Fc-01 (n=1), using the degradation rate of the substrate peptide as an index.
FIG. 12(B) is a table showing human MMP-9 inhibitory activity $IC_{50}$ of the active MMP-9-binding peptide M91005 and its C-terminal conjugate M91005-Fc-01 (n=1) when the substrate peptide was used.
Figures 13A, 13B:
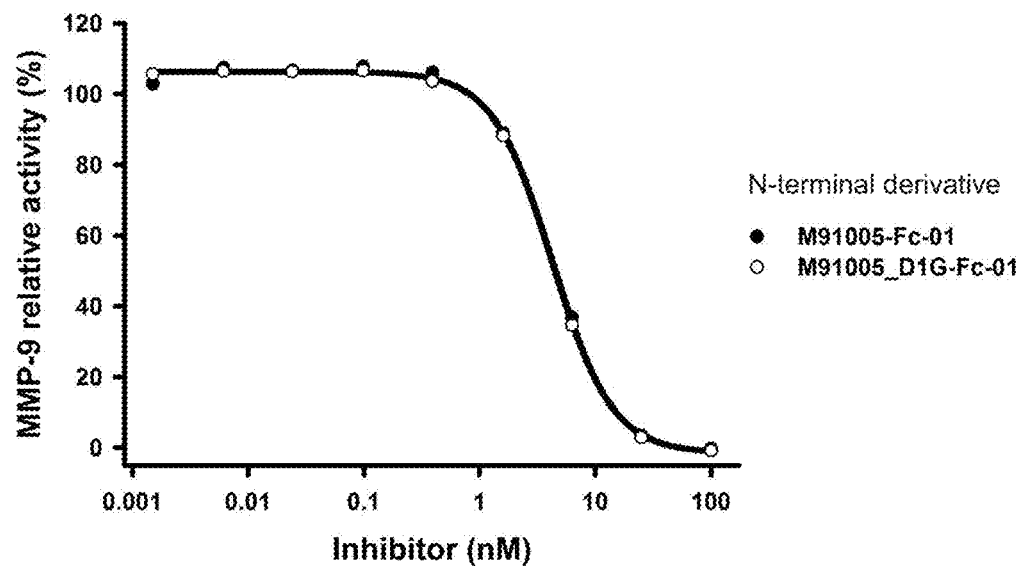
FIG. 13(A) is a graph showing an evaluation of human MMP-9 inhibitory activity of the active MMP-9-binding peptide C-terminal conjugate M91005-Fc-01 and its N-terminal derivative M91005_D1G-Fc-01 (n=1), using the degradation rate of the substrate peptide as an index.
FIG. 13(B) is a table showing the human MMP-9 inhibitory activity $IC_{50}$ of the active MMP-9-binding peptide C-terminal conjugate M91005-Fc-01 and its N-terminal derivative M91005_D1G-Fc-01 (n=1) when the substrate peptide was used.

Example 8. Evaluation of MMP-9 Inhibitory Activity of Active MMP-9-Binding Peptide Derivatives According to the method described in (4-1), human MMP-9 inhibitory activity of each of the binding peptides was evaluated with 0.6 nM final concentration of active hMMP-9(cat)_His6 and 0.0015 to 100 nM final concentration of each active MMP-9-binding peptide (FIGS. 11(A), 12(A), and 13(A)). The 50% inhibitory concentration (IC$_{50}$) was calculated using GraphPad Prism (version 5.0; GraphPad Software), and as the result, it was revealed that the inhibitory activities of M91002_G3, M91002_G2, and M91002_G0 are equivalent to that of M91002 (FIG. 11 (B)), and the addition of one to six amino acids to the C-terminal of the binding peptide does not affect the MMP-9 inhibitory activity. It was also shown that the inhibitory activities of M91005-Fc-01 and M91005 are equivalent (FIG. 12 (B)), and Fc conjugation does not affect the MMP-9 inhibitory activity. Furthermore, it was shown that the inhibitory activities of M91005-Fc-01 and M91005_D1G-Fc-01 are equivalent (FIG. 13 (B)), and substitution of Asp 1 in the binding peptide with Gly does not affect the MMP-9 inhibitory activity.

Example 9. Detection of Active MMP-9 Using Active MMP-9-Binding Peptide Derivative (Fc Conjugate)

With M91005-Fc-01 prepared in (7-2) and pro-hMMP-9 (cat)_His6 and active hMMP-9(cat)_His6 prepared in (2-1), the binding activity was evaluated by an immunoprecipitation method. 3 µg of the active MMP-9-binding peptide derivative and 1.5 mg of Dynabeads™ Protein G for Immunoprecipitation (Thermo Fisher Scientific) were mixed, and reacted at room temperature for 30 minutes. After washing, 0.39 µg of pro human MMP-9 enzyme active domain or 0.63 µg of active human MMP-9 enzyme active domain was added, and the mixture was reacted at 4° C. for 1 hour. After separating the beads with a magnet, the supernatant fraction (FT) was recovered. After washing the beads, a sample buffer (reduction) for SDS-PAGE was added, and reacted at 99° C. for 5 minutes, and the samples bound to the beads were recovered as a precipitation fraction (Elu). The added human MMP-9 enzyme active domain (Inp), FT and Elu were subjected to SDS-PAGE, and the binding activity was assessed by detection with Biotinylated Human MMP-9 Antibody (R&D Systems; BAF911) and Streptavidin-HRP Conjugate (GE Healthcare; RPN2280). As a buffer for the reactions, a buffer of 50 mM Tris-HCl, 200 mM NaCl, 2 mM CaCl$_2$, pH 7.5 was used.

Figure 14A:
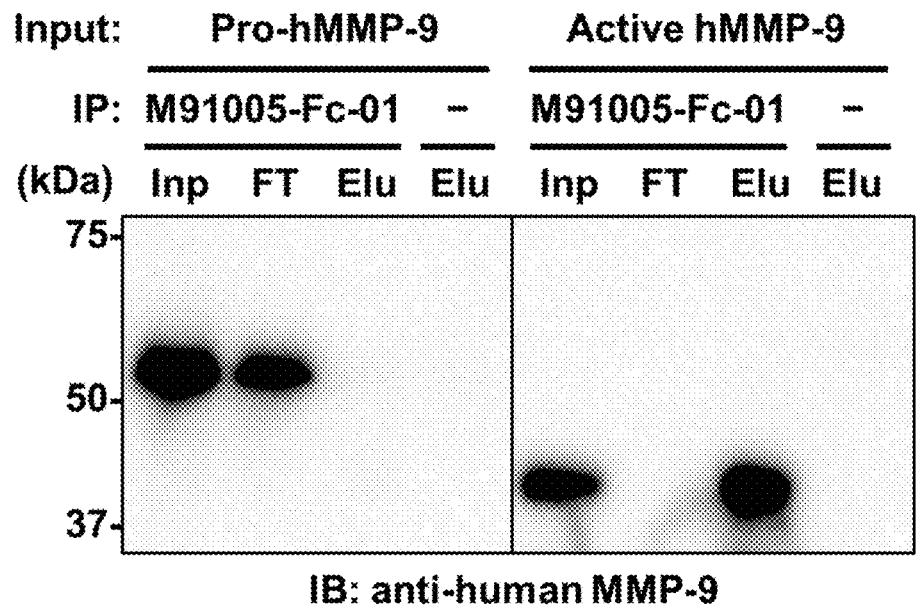
FIG. 14(A) is an image of data showing an evaluation of whether the active MMP-9-binding peptide does not bind to pro human MMP-9 but does bind to active human MMP-9, by an immunoprecipitation method. The added human MMP-9 enzyme active domain is denoted as Input (Inp), the supernatant fraction which did not bind to the beads is denoted as Flow-through (FT), and the precipitate fraction which bound to the beads is denoted as Eluate (Elu). When the pro human MMP-9 enzyme active domain was added, a band of about 50 kDa was detected in the Inp and FT lanes, and no band was detected in the Elu lane. When the active human MMP-9 enzyme active domain was added, a band of about 40 kDa was detected in the Inp and Elu lanes, and no band was detected in the FT lane. When immunoprecipitation occurred without adding the active MMP-9-binding peptide C-terminal conjugate M91005-Fc-01, no band was detected in the Elu lane.

When the beads linked to M91005-Fc-01 were used, pro-hMMP-9(cat)_His6 was not detected in the Elu lane, while active hMMP-9(cat)_His6 was detected in the Elu lane. In contrast, when the beads not linked to M91005-Fc-01 were used, pro-hMMP-9(cat)_His6 and active hMMP-9 (cat)_His6 were not detected in the Elu lanes (FIG. 14(A)). Thus, it was shown that the active MMP-9-binding peptide derivative (Fc conjugate) does not bind to pro human MMP-9, but specifically binds to active human MMP-9.

In the same way, using M91005-Fc-01 prepared in (7-2), and pro-mMMP-9(cat)_His6_FLAG_Avi and active mMMP-9(cat)_FLAG_Avi prepared in (2-2), the binding activity was evaluated by an immunoprecipitation method. Samples for evaluation were subjected to SDS-PAGE, and the binding activity was evaluated by detection using Mouse MMP-9 Antibody (R&D Systems; AF909) and Peroxidase AffiniPure F(ab')$_2$ Fragment Donkey Anti-Goat IgG(H+L) (Jackson ImmunoResearch Inc.; 705-036-147).

Figure 14B:
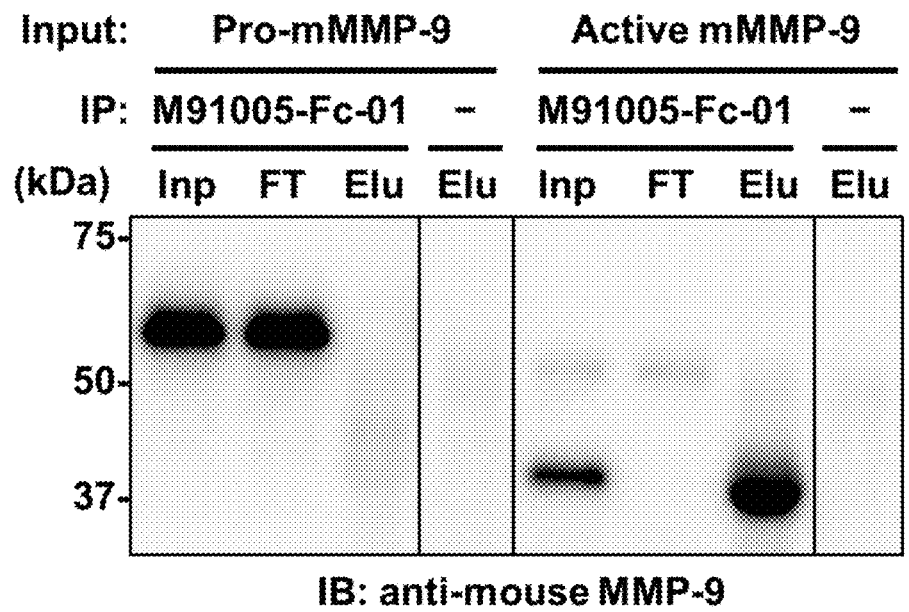
FIG. 14(B) is an image of data showing an evaluation of whether the active MMP-9-binding peptide does not bind to pro mouse MMP-9 but does bind to active mouse MMP-9, by an immunoprecipitation method. The added mouse MMP-9 enzyme active domain is denoted as Input (Inp), the supernatant fraction which did not bind to the beads is denoted as Flow-through (FT), and the precipitate fraction which bound to the beads is denoted as Eluate (Elu). When the pro mouse MMP-9 enzyme active domain was added, a band of about 60 kDa was detected in the Inp and FT lanes, and no band was detected in the Elu lane. When the active mouse MMP-9 enzyme active domain was added, a band of about 40 kDa was detected in the Inp and Elu lanes, and no band was detected in the FT lane. When the immunoprecipitation occurred without adding C-terminal conjugate M91005-Fc-01 of the active MMP-9-binding peptide, no band was detected in the Elu lane.

When M91005-Fc-01-bound beads were used, pro-mMMP-9(cat)_His6_FLAG_Avi was not detected in the Elu lane, while active mMMP-9(cat)_FLAG_Avi was detected in the Elu lane. In contrast, when the beads not linked to M91005-Fc-01 were used, pro-mMMP-9(cat)_ His6_FLAG_Avi and active mMMP-9(cat)_FLAG_Avi were not detected in the Elu lanes (FIG. 14(B)). Thus, it was shown that the active MMP-9-binding peptide derivative (Fc conjugate) does not bind to pro mouse MMP-9 but binds specifically to active mouse MMP-9.

Example 10. Specificity Evaluation of Active MMP-9-Binding Peptide (Serine Protease)

The specificities for 12 kinds of serine proteases were evaluated using substrate peptide cleavage as an index. 25 µl of protease and 25 µl of a sample (final concentration of 1 µM) diluted with an assay buffer (50 mM Tris-HCl, 150 mM NaCl, pH 8.0) were mixed, and the mixture was reacted at 37° C. for 20 minutes. Then, 50 µl of the substrate diluted with the assay buffer was added, and fluorescence signals (excitation 380 nm/emission 460 nm) were measured with Enspire (PerkinElmer, Inc.). For reactions and measurements, a ProteoSave™ SS96F black plate (Sumitomo Bakelite Co., Ltd.) was used. The combinations of proteases and substrates used for the specificity evaluation were as follows.

Human Trypsin inhibitory activity evaluation; 1 nM final concentration of Trypsin from Human Pancreas (Sigma-Aldrich Co.; T6264), and 10 µM final concentration of substrate peptide Boc-FSR-MCA (FIG. 55) (PEPTIDE INSTITUTE, INC.; 3107-v)

Human Chymotrypsin inhibitory activity evaluation; 10 nM final concentration of α-Chymotrypsin from human pancreas (Sigma-Aldrich Co.; C8946), and 10 µM final concentration of substrate Peptide Suc-LLVY-MCA (SEQ ID NO: 36, FIG. 56) (PEPTIDE INSTITUTE, INC.; 3120-v)

Human Tryptase inhibitory activity evaluation; 1 nM final concentration of Tryptase from human lung (Sigma-Aldrich Co.; T7063), and 100 µM final concentration of substrate peptide Boc-FSR-MCA (FIG. 55) (PEPTIDE INSTITUTE, INC.; 3107-v)

Human Chymase inhibitory activity evaluation; 100 nM final concentration of Chymase human recombinant expressed in *Pichia pastoris* (Sigma-Aldrich Co.; C8118), and 100 µM final concentration of substrate peptide Suc-AAPF-MCA (SEQ ID NO: 37, FIG. 57) (PEPTIDE INSTITUTE, INC.; 3114-v)

Human Plasmin inhibitory activity evaluation; 50 nM final concentration Plasmin from human plasma (Sigma-Aldrich Co.; P1867), and 100 µM final concentration of substrate peptide Boc-VLK-MCA (FIG. 58) (PEPTIDE INSTITUTE, INC.; 3104-v)

Human Thrombin inhibitory activity evaluation; 1 nM final concentration of Thrombin from human plasma (Sigma-Aldrich Co.; T1063), and 100 µM final concentration of substrate peptide Boc-VPR-AMC (FIG. 59) (R&D Systems, Inc.; ES011)

Human Elastase inhibitory activity evaluation; 0.01 U/ml final concentration of Neutrophil elastase (human) (Enzo Life Sciences, Inc.; BML-SE284), and 100 µM final concentration of substrate peptide Suc(OMe)-Ala-Ala-Pro-Val-MCA (SEQ ID NO: 38, FIG. 60) (PEPTIDE INSTITUTE, INC.; 3153-v)

Human Matriptase inhibitory activity evaluation: 1 nM final concentration of Recombinant Human Matriptase/ST14 Catalytic Domain (R&D Systems, Inc.; 3946-SE), and 100 µM final concentration of substrate peptide Boc-QAR-AMC (FIG. 61) (R&D Systems, Inc.; ES014)

Human Protein C inhibitory activity evaluation; 100 nM final concentration of Protein C from human plasma (Sigma-Aldrich Co.; P2562), and 100 µM final concentration of substrate peptide Boc-LSTR-MCA (SEQ ID NO: 39, FIG. 62) (PEPTIDE INSTITUTE, INC.; 3112-v)

Human tPA inhibitory activity evaluation; 10 nM final concentration of tissue plasminogen activator human (Sigma-Aldrich Co.; 10831), and 100 µM final concentration of substrate peptide Pyr-GR-MCA (FIG. 63) (PEPTIDE INSTITUTE, INC.; 3145-v)

Human uPA inhibitory activity evaluation; 2 nM final concentration of urokinase from human urine (Sigma-Aldrich Co.; U0633), and 100 µM final concentration of substrate peptide Pyr-GR-MCA (FIG. 63) (PEPTIDE INSTITUTE, INC.; 3145-v)

Human Plasma Kallikrein inhibitory activity evaluation; 0.125 µg/ml final concentration of recombinant human plasma kallikrein/KLKB1 Protein (R&D Systems, Inc.; 2497-SE), and 100 µM final concentration of substrate peptide Z—FR-MCA (FIG. 64) (PEPTIDE INSTITUTE, INC.; 3095-v).

In the same way as in (4-1), the specificity for serine protease was evaluated using degradation of the substrate peptide as an index. At a final concentration of 1 μM of the inhibitors, each binding peptide did not inhibit protease activities of any of the proteases, indicating that the active MMP-9-binding peptide has MMP-9 specific inhibitory action (FIG. 52). In contrast, a non-selective inhibitor namely Protease Inhibitor Cocktail (Sigma-Aldrich Co.; 11836170001) inhibited all proteases at a final concentration of 1 μM (FIG. 52).

Example 11. Preparation of Human MMP-9 Enzyme Active Domain E402Q Mutant (11-1) Construction of pCMA-Pro-hMMP-9(Cat)_E402Q_His6
PCR was performed using pCMA-pro-hMMP-9(cat)_His6 constructed in (2-1-1) as a template, and pCMA-pro-hMMP-9(cat)_E402Q_His6 having, downstream of the CMV promoter, a nucleotide sequence encoding a secretion signal (Met1-Ala19) of human MMP-9 (SEQ ID NO: 28 (FIG. 44)), a propeptide (Ala20-Arg106), an enzyme active domain E402Q mutant (Phe107-Pro449, E402Q) and a His tag was constructed.

(11-2) Preparation of Pro-hMMP-9(Cat)_E402Q_His6
The pCMA-pro-hMMP-9(cat)_E402Q_His6 constructed in (11-1) was transfected into FreeStyle 293F (Thermo Fisher Scientific) using Polyethyleneimine Max (Polysciences, Inc.), and six days later, the culture supernatant was recovered. The His tag fusion protein was recovered by HisTrap excel (GE Healthcare), and the buffer solution was replaced with PBS to purify pro-hMMP-9(cat)_E402Q_His6.

(11-3) Preparation of hMMP-9(Cat)_E402Q_His6
The pro-hMMP-9(cat)_E402Q_His6 obtained in (11-2) and hMMP-3 activated with APMA were mixed, and reacted at 37° C. for 4 hours. The reaction solution was replaced with PBS at low temperature to purify hMMP-9(cat)_E402Q_His6.

Example 12. Interaction Analysis Between Active MMP-9-Binding Peptide and Human MMP-9 Active Center Glu402 Residue With M91005 and M91011 prepared in (1-2), active hMMP-9(cat)_His6 prepared in (2-1-4), and hMMP-9(cat)_E402Q_His6 prepared in (11-3), the binding activity was evaluated by size exclusion chromatography. 25 μM active hMMP-9(cat)_His6 or hMMP-9(cat)_E402Q_His6 and 75 μM active MMP-9-binding peptide or hTIMP-1 (in-house preparation) were mixed, and reacted at 4° C. for 1 hour. After the reaction, 10 μl of the reaction solution was analyzed by size exclusion chromatography. The chromatographic conditions were as follows.
Column: ACQUITY UPLC BEH200 column (Waters; 186005225)
Mobile phase: PBS
Detection: Absorbance (280 nm)
When only active hMMP-9(cat)_His6 was analyzed, the peak of active hMMP-9(cat)_His6 was detected at a retention time of 7.0 minutes (FIG. 53(A)). When a mixture reaction solution of active hMMP-9(cat)_His6 and hTIMP-1 or active MMP-9-binding peptides M91005 or M91011 was analyzed, the retention time of the peak of active hMMP-9(cat)_His6 was shifted to the high molecular weight side (FIG. 53(A)). Thus, it was shown that hTIMP-1 and the active MMP-9-binding peptides M91005 and M91011 bind to the active human MMP-9 enzyme active domain. When only human MMP-9(cat)_E402Q_His6 was analyzed, the peak of hMMP-9(cat)_E402Q_His6 was detected at a retention time of 7.1 minutes (FIG. 53(B)). When a mixed reaction solution of human MMP-9(cat)_E402Q_His6 and hTIMP-1 was analyzed, the retention time of the peak of hMMP-9(cat)_E402Q_His6 was shifted to the high molecular weight side (FIG. 53(B)). Thus, it was shown that hTIMP-1 binds to the human MMP-9 enzyme active domain E402Q mutant. In contrast, when a mixture reaction solution of hMMP-9(cat)_E402Q_His6 and the active MMP-9-binding peptide M91005 or M91011 was analyzed, the retention time of the peak of the hMMP-9(cat)_E402Q_His6 was not changed (FIG. 53(B)). It should be noted that when only hTIMP-1 or the active MMP-9-binding peptides M91005, M91011 was analyzed, the peak of hTIMP-1 was detected at a retention time of 7.3 minutes, the peak of the active MMP-9-binding peptide M91005 was detected at a retention time of 8.2 minutes, and the peak of the active MMP-9-binding peptide M91011 was detected at a retention time of 8.1 minutes (FIG. 53(C)).

Thus, it was shown that the active MMP-9-binding peptides M91005 and M91011 do not bind to human MMP-9 enzyme active domain E402Q mutant. Consequently, it was shown that the active MMP-9-binding peptides M91005 and M91011 recognize and bind to the Glu402 residue which is the active center of human MMP-9.

Example 13. Preparation of Active Human MMP-9 Enzyme Active Domain Mutant (13-1) Construction of pCMA-Pro-His6 EK-hMMP-9 (Cat)
PCR was performed using pCMA-pro-hMMP-9(cat)_His6 constructed in (2-1-1) as a template, and pCMA-pro-His6_EK-hMMP-9(cat) having, downstream of the CMV promoter, a nucleotide sequence encoding a secretion signal (Met1-Ala19) of human MMP-9 (SEQ ID NO: 28 (FIG. 44)), a His tag, a propeptide (Ala20-Arg106), an enterokinase recognition sequence (FIG. 65: SEQ ID NO: 40) and an enzyme active domain (Phe107-Pro449) was constructed.

(13-2) Construction of pCMA-Pro-His6_EK-hMMP-9 (Cat)_Xnnny
PCR was performed using pCMA-pro-His6_EK-hMMP-9(cat) constructed in (13-1) as a template, and pCMA-pro-His6_EK-hMMP-9(cat)_Q108N, pCMA-pro-His6_EK-hMMP-9(cat)_T109F, pCMA-pro-His6_EK-hMMP-9(cat)_F110A, pCMA-pro-His6_EK-hMMP-9(cat)_E111P, pCMA-pro-His6_EK-hMMP-9(cat)_G112R, pCMA-pro-His6_EK-hMMP-9(cat)_D113K, pCMA-pro-His6_EK-hMMP-9(cat) L114P, pCMA-pro-His6_EK-hMMP-9(cat)_Y179A, pCMA-pro-His6_EK-hMMP-9(cat)_P180A, pCMA-pro-His6_EK-hMMP-9(cat)_D185A, pCMA-pro-His6_EK-hMMP-9(cat)_G186A, pCMA-pro-His6_EK-hMMP-9(cat) L187A, pCMA-pro-His6_EK-hMMP-9(cat)_F192A, pCMA-pro-His6_EK-hMMP-9(cat)_P193A, pCMA-pro-His6_EK-hMMP-9(cat)_P196T, pCMA-pro-His6_EK-hMMP-9(cat)_I198V, pCMA-pro-His6_EK-hMMP-9(cat)_Q199G, pCMA-pro-His6_EK-hMMP-9 (cat)_Y393A, pCMA-pro-His6_EK-hMMP-9(cat)_L397A, pCMA-pro-His6_EK-hMMP-9(cat)_V398A, pCMA-pro-His6_EK-hMMP-9(cat)_D410E, pCMA-pro-His6_EK-hMMP-9(cat) S413Q, pCMA-pro-His6_EK-hMMP-9(cat)_L418A, pCMA-pro-His6_EK-hMMP-9(cat)_Y420A, pCMA-pro-His6_EK-hMMP-9(cat)_P421A, pCMA-pro-His6_EK-hMMP-9(cat)_M422I, pCMA-pro-His6_EK-hMMP-9(cat)_Y423A, and pCMA-pro-His6_EK-hMMP-9

(cat)_R424T having, at the downstream of the CMV promoter, a nucleotide sequence encoding a secretion signal (Met1-Ala19) of human MMP-9 (SEQ ID NO: 28 (FIG. 44)), a His tag, a propeptide (Ala20-Arg106), an enterokinase recognition sequence (FIG. 65, SEQ ID NO: 40)), and a mutant (Q108N, T109F, F110A, E111P, G112R, D113K, L114P, Y179A, P180A, D185A, G186A, L187A, F192A, P193A, P196T, I198V, Q199G, Y393A, L397A, V398A, D410E, S413Q, L418A, Y420A, P421A, M422I, Y423A or R424T) of the enzyme active domain (Phe107-Pro449) were constructed.

(13-3) Preparation of Pro-His6_EK-hMMP-9(Cat)

pCMA-pro-His6_EK-hMMP-9(cat) constructed in (13-1) was transfected into FreeStyle 293F (Thermo Fisher Scientific) using Polyethyleneimine Max (Polysciences, Inc.), and six days later, the culture supernatant was recovered. The His tag fusion proteins were recovered by HisTrap excel (GE Healthcare) and gelatin-Sepharose resin (GE Healthcare), and the buffer solution was replaced with PBS to purify pro-His6_EK-hMMP-9(cat).

(13-4) Preparation of Active hMMP-9(Cat)

The pro-His6_EK-hMMP-9(cat) obtained in (13-3) and EKMax Enterokinase (Thermo Fisher Scientific) were mixed and reacted at 4° C. for 2 hours. After removing enterokinase from the reaction solution with EKapture Agarose (EMD Millipore), the buffer solution was replaced with PBS at low temperature to purify active hMMP-9(cat).

(13-5) Preparation of Pro-His6_EK-hMMP-9(Cat)_XnnnY

The pCMA-pro-His6_EK-hMMP-9(cat)_XnnnY constructed in (13-2) was transfected into FreeStyle 293F (Thermo Fisher Scientific) using Polyethyleneimine Max (Polysciences, Inc.), and six days later, the culture supernatant was recovered. The His tag fusion proteins were recovered by HisTrap excel (GE Healthcare) and a gelatin-Sepharose resin (GE Healthcare), and the buffer solution was replaced with PBS to purify pro-His6_EK-hMMP-9(cat)_Q108N, pro-His6_EK-hMMP-9(cat)_T109F, pro-His6_EK-hMMP-9(cat)_F110A, pro-His6_EK-hMMP-9(cat)_E111P, pro-His6_EK-hMMP-9(cat)_G112R, pro-His6_EK-hMMP-9(cat)_D113K, pro-His6_EK-hMMP-9(cat)_L114P, pro-His6_EK-hMMP-9(cat)_Y179A, pro-His6_EK-hMMP-9(cat)_P180A, pro-His6_EK-hMMP-9(cat)_D185A, pro-His6_EK-hMMP-9(cat)_G186A, pro-His6_EK-hMMP-9(cat)_L187A, pro-His6_EK-hMMP-9(cat)_F192A, pro-His6_EK-hMMP-9(cat)_P193A, pro-His6_EK-hMMP-9(cat)_P196T, pro-His6_EK-hMMP-9(cat)_I198V, pro-His6_EK-hMMP-9(cat)_Q199G, pro-His6_EK-hMMP-9(cat)_Y393A, pro-His6_EK-hMMP-9(cat)_L397A, pro-His6_EK-hMMP-9(cat)_V398A, pro-His6_EK-hMMP-9(cat)_D410E, pro-His6_EK-hMMP-9(cat) S413Q, pro-His6_EK-hMMP-9(cat)_L418A, pro-His6_EK-hMMP-9(cat)_Y420A, pro-His6_EK-hMMP-9(cat)_P421A, pro-His6_EK-hMMP-9(cat)_M422I, pro-His6_EK-hMMP-9(cat)_Y423A, and pro-His6_EK-hMMP-9(cat)_R424T.

(13-6) Preparation of Active hMMP-9(Cat)_XnnnY

The pro-His6_EK-hMMP-9(cat)_XnnnY obtained in (13-5) and EKMax Enterokinase (Thermo Fisher Scientific) were mixed, and reacted at 4° C. for 2 hours. After removing the enterokinase from the reaction solution by EKapture Agarose (EMD Millipore), the buffer solution was replaced with PBS at low temperature to purify active hMMP-9(cat)_Q108N, active hMMP-9(cat)_T109F, active hMMP-9(cat)_F110A, active hMMP-9(cat)_E111P, active hMMP-9(cat)_G112R, active hMMP-9(cat)_D113K, active hMMP-9(cat)_L114P, active hMMP-9(cat)_Y179A, active hMMP-9(cat)_P180A, active hMMP-9(cat)_D185A, active hMMP-9(cat)_G186A, active hMMP-9(cat)_L187A, active hMMP-9(cat)_F192A, active hMMP-9(cat)_P193A, active hMMP-9(cat)_P196T, active hMMP-9(cat)_I198V, active hMMP-9(cat)_Q199G, active hMMP-9(cat)_Y393A, active hMMP-9(cat)_L397A, active hMMP-9(cat)_V398A, active hMMP-9(cat)_D410E, active hMMP-9(cat) S413Q, active hMMP-9(cat)_L418A, active hMMP-9(cat)_Y420A, active hMMP-9(cat)_P421A, active hMMP-9(cat)_M422I, active hMMP-9(cat)_Y423A, and active hMMP-9(cat)_R424T.

Example 14. Interaction Analysis Between Active MMP-9-Binding Peptide and Active Human MMP-9 Enzyme Active Domain Mutant With M91005 and M91011 prepared in (1-2), active hMMP-9(cat) prepared in (13-4) and active hMMP-9(cat)_XnnnY prepared in (13-6), human MMP-9 inhibitory activity was evaluated.

The substrate peptide MOCAc—KPLGL-A$_2$pr(Dnp)-AR—NH$_2$ (SEQ ID NO: 30 (FIG. 46)) (PEPTIDE INSTITUTE, INC.; 3226-v) was dissolved in water to 1 mM, then diluted with an assay buffer (50 mM Tris-HCl, 200 mM NaCl, 2 mM CaCl$_2$, pH7.5) and used at the final concentration of 10 µM. 50 µl each of the active hMMP-9(cat) diluted with the assay buffer or the active hMMP-9(cat)_XnnnY and the active MMP-9-binding peptide or sc-311438 (Santa Cruz Biotechnology, Inc.) were mixed, and reacted at 37° C. for 1 hour. Then, 100 µl of the substrate diluted with the assay buffer was added, and fluorescence signals (excitation 328 nm/emission 393 nm) were measured with Enspire (PerkinElmer, Inc.). The final concentrations of the active hMMP-9(cat) and the active hMMP-9(cat)_ XnnnY were at 1 nM, and the final concentrations of the active MMP-9-binding peptide and sc-311438 were at 0.5 to 330 nM. For reactions and measurements, a ProteoSave™ SS96F black plate (Sumitomo Bakelite Co., Ltd.) was used.

The 50% inhibitory concentration (IC$_{50}$) of each binding peptide was calculated using GraphPad Prism (version 5.0; GraphPad Software), by calculating the substrate peptide degradation rate of the active MMP-9-binding peptide at each concentration, and taking the degradation rate at an inhibitor concentration of 0 nM as 100% (FIGS. 54(A) and 54(B)). When the wild-type active hMMP-9(cat) was used, IC$_{50}$ of a non-selective inhibitor sc-311438 was 28±7 nM, IC$_{50}$ of the active MMP-9-binding peptide M91005 was 17±7 nM, and IC$_{50}$ of the active MMP-9-binding peptide M91011 was 17±5 nM. When the active hMMP-9(cat)_ XnnnY was used, IC$_{50}$ of the non-selective inhibitor sc-311438 was less than twice that of the wild type, and no significant difference was observed. Since the non-selective inhibitor sc-311438 recognizes and binds to a zinc ion at the active center, it is believed that there is little effect of substitution of residues other than those in the active centers. In contrast, when active hMMP-9(cat)_F110A, active hMMP-9(cat)_Y179A, active hMMP-9(cat)_L187A, active hMMP-9(cat)_F192A, active hMMP-9(cat)_Q199G, active hMMP-9(cat)_Y393A, active hMMP-9(cat)_L397A, active hMMP-9(cat)_V398A, active hMMP-9(cat)_Y420A, active hMMP-9(cat)_M422I and active hMMP-9(cat)_Y423A were used, IC$_{50}$ of the active MMP-9-binding peptide M91005 was increased 4.0 times, 3.2 times, 6.7 times, >57.8 times, 2.3 times, 2.7 times, 2.2 times, 2.2 times, 3.1 times, 2.6 times and 13.2 times, respectively, compared to when the wild type was used. Thus, it has been suggested that the active MMP-9-binding peptide M91005 recognizes Phe110, Tyr179, Leu187, Phe192, Gln199, Tyr393, Leu397, Val398, Tyr420, Met422 and Tyr423 of human MMP-9 and binds to active human MMP-9. Similarly, when active hMMP-9(cat)_Y179A, active hMMP-9(cat)_D185A, active hMMP-9(cat)_F192A, active hMMP-9(cat)_P193A, active hMMP-9(cat)_Y393A, active hMMP-9(cat)_L397A, active hMMP-9(cat)_V398A, active hMMP-9(cat)_M422I, active hMMP-9(cat)_Y423A and active hMMP-9(cat)_R424T were used, $IC_{50}$ of the active MMP-9-binding peptide M91011 was increased 4.9 times, 19.0 times, 5.0 times, 6.5 times, >57.6 times, 3.5 times, 4.8 times, 2.6 times, >20.0 times and 2.7 times, respectively, compared to when the wild type is used. Thus, it has been suggested that the active MMP-9-binding peptide M91011 recognizes Tyr179, Asp185, Phe192, Phe193, Tyr393, Leu397, Val398, Met422, Tyr423 and Arg424 of human MMP-9, and binds to active human MMP-9.

INDUSTRIAL APPLICABILITY

The peptide provided by the present invention as well as the pharmaceutical and diagnostic compositions containing the peptide are useful for treatment, prevention, test, diagnosis or the like of diseases related to MMP-9.

Free Text of Sequence Listing

SEQ ID NO: 1: Amino acid sequence of human SPINK2 (FIG. 15)
SEQ ID NO: 2: Amino acid sequence of active MMP-9-binding peptide M91001 (FIG. 16)
SEQ ID NO: 3: Amino acid sequence of active MMP-9-binding peptide M91002 (FIG. 17)
SEQ ID NO: 4: Amino acid sequence of active MMP-9-binding peptide M91004 (FIG. 18)
SEQ ID NO: 5: Amino acid sequence of active MMP-9-binding peptide M91005 (FIG. 19)
SEQ ID NO: 6: Amino acid sequence of active MMP-9-binding peptide M91010 (FIG. 20)
SEQ ID NO: 7: Amino acid sequence of active MMP-9-binding peptide M91011 (FIG. 21)
SEQ ID NO: 8: Amino acid sequence of active MMP-9-binding peptide M91012 (FIG. 22)
SEQ ID NO: 9: Amino acid sequence of active MMP-9-binding peptide M91014 (FIG. 23)
SEQ ID NO: 10: Amino acid sequence of active MMP-9-binding peptide M91001_D1G (FIG. 24)
SEQ ID NO: 11: Amino acid sequence of active MMP-9-binding peptide M91002_D1G (FIG. 25)
SEQ ID NO: 12: Amino acid sequence of active MMP-9-binding peptide M91004_D1G (FIG. 26)
SEQ ID NO: 13: Amino acid sequence of active MMP-9-binding peptide M91005_D1G (FIG. 27)
SEQ ID NO: 14: Amino acid sequence of active MMP-9-binding peptide M91010_D1G (FIG. 28)
SEQ ID NO: 15: Amino acid sequence of active MMP-9-binding peptide M91011_D1G (FIG. 29)
SEQ ID NO: 16: Amino acid sequence of active MMP-9-binding peptide M91012_D1G (FIG. 30)
SEQ ID NO: 17: Amino acid sequence of active MMP-9-binding peptide M91014_D1G (FIG. 31)
SEQ ID NO: 18: General formula of active MMP-9-binding peptide (FIG. 32)
SEQ ID NO: 19: Amino acid sequence of Stag+linker 1 (FIG. 33)
SEQ ID NO: 20: Amino acid sequence of Stag+linker 2 (FIG. 34)
SEQ ID NO: 21: Amino acid sequence of C-terminal 6-mer (FIG. 35)
SEQ ID NO: 22: Amino acid sequence of G4S linker (FIG. 38)
SEQ ID NO: 23: Amino acid sequence of human IgG1 Fc (FIG. 39)
SEQ ID NO: 24: Nucleotide sequence of primer 1 (FIG. 40)
SEQ ID NO: 25: Nucleotide sequence of primer 2 (FIG. 41)
SEQ ID NO: 26: Nucleotide sequence of primer 3 (FIG. 42)
SEQ ID NO: 27: Nucleotide sequence of primer 4 (FIG. 43)
SEQ ID NO: 28: Amino acid sequence of human MMP-9 (FIG. 44)
SEQ ID NO: 29: Amino acid sequence of mouse MMP-9 (FIG. 45)
SEQ ID NO: 30: Amino acid sequence of MOCAc—KPLGL-$A_2$pr(Dnp)-AR—$NH_2$ (FIG. 46)
SEQ ID NO: 31: Amino acid sequence of MOCAc—PLGL-$A_2$pr(Dnp)-AR—$NH_2$ (FIG. 47)
SEQ ID NO: 32: Amino acid sequence of DNP—PLGMWSR (FIG. 48)
SEQ ID NO: 33: Amino acid sequence of MOCAc—RPKPVE-Nva-WR-Lys (Dnp)-$NH_2$ (FIG. 49)
SEQ ID NO: 34: Amino acid sequence of a FLAG tag (FIG. 50)
SEQ ID NO: 35: Amino acid sequence of Avi tag (FIG. 51)
SEQ ID NO: 36: Amino acid sequence of Suc-LLVY-MCA (FIG. 56)
SEQ ID NO: 37: Amino acid sequence of Suc-AAPF-MCA (FIG. 57)
SEQ ID NO: 38: Amino acid sequence of Suc(OMe)-Ala-Ala-Pro-Val-MCA (FIG. 60)
SEQ ID NO: 39: Amino acid sequence of Boc-LSTR-MCA (FIG. 62)
SEQ ID NO: 40: Amino acid sequence of enterokinase recognition sequence (FIG. 65)

The invention claimed is:

1. A SPINK2 mutant peptide comprising the amino acid sequence as set forth in any one of SEQ ID NO: 2 to 7, wherein the peptide binds to active human MMP-9 but does not bind to pro human MMP-9.

2. The peptide according to claim 1, wherein the peptide binds to the catalytic domain of the active human MMP-9.

3. The peptide according to claim 1, wherein the peptide inhibits the protease activity of human MMP-9.

4. The peptide according to claim 3, wherein the inhibition is specific to human MMP-9.

5. The peptide according to claim 1, further comprising the amino acid sequence as set forth in SEQ ID NO: 19 or SEQ ID NO: 20, wherein the amino acid sequence as set forth in SEQ ID NO: 19 or SEQ ID NO: 20 is linked to the N-terminal amino acid of the amino acid sequence as set forth in any one of SEQ ID NO: 2-17.

6. The peptide according to claim 1, further comprising an amino acid sequence consisting of 1 to 6 amino acids, wherein the amino acid sequence consisting of 1 to 6 amino acids is linked to the C-terminal amino acid of the amino acid sequence as set forth in any one of SEQ ID NO: 2-17.

7. The peptide according to claim 1, wherein the peptide comprises three disulfide bonds, a loop structure, an α-helix, and a β-sheet.

8. A composition comprising the peptide according to claim 1.

9. A pharmaceutical composition comprising the peptide according to claim 1.

* * * * *

UNITED STATES PATENT AND TRADEMARK OFFICE
CERTIFICATE OF CORRECTION

PATENT NO. : 11,926,655 B2
APPLICATION NO. : 16/631394
DATED : March 12, 2024
INVENTOR(S) : H. Yano et al.

It is certified that error appears in the above-identified patent and that said Letters Patent is hereby corrected as shown below:

In the Claims

| Column | Line | Claim | |
|--------|------|-------|---|
| 91 | 21 | 1 | Change "2 to 7" to -- 2-17 -- |

Signed and Sealed this
Twelfth Day of November, 2024

Katherine Kelly Vidal
*Director of the United States Patent and Trademark Office*

SEQUENCE LISTING

```
<160> NUMBER OF SEQ ID NOS: 42

<210> SEQ ID NO 1
<211> LENGTH: 63
<212> TYPE: PRT
<213> ORGANISM: Homo sapiens

<400> SEQUENCE: 1

Asp Pro Gln Phe Gly Leu Phe Ser Lys Tyr Arg Thr Pro Asn Cys Ser
1               5                   10                  15

Gln Tyr Arg Leu Pro Gly Cys Pro Arg His Phe Asn Pro Val Cys Gly
            20                  25                  30
```

-continued

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
    50                  55                  60

<210> SEQ ID NO 2
<211> LENGTH: 63
<212> TYPE: PRT
<213> ORGANISM: Artificial Sequence
<220> FEATURE:
<223> OTHER INFORMATION: binder

<400> SEQUENCE: 2

Asp Pro Gln Phe Gly Leu Phe Ser Lys Tyr Arg Thr Pro Asn Cys Gln
1               5                   10                  15

Arg Gly Ile Gly Pro Ser Cys Gln Met Ser Tyr Lys Pro Val Cys Gly
            20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
    50                  55                  60

<210> SEQ ID NO 3
<211> LENGTH: 63
<212> TYPE: PRT
<213> ORGANISM: Artificial Sequence
<220> FEATURE:
<223> OTHER INFORMATION: binder

<400> SEQUENCE: 3

Asp Pro Gln Phe Gly Leu Phe Ser Lys Tyr Arg Thr Pro Asn Cys Arg
1               5                   10                  15

Thr Gly Arg Gly Pro Ala Cys Gln Met Gly Phe Gln Pro Val Cys Gly
            20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
    50                  55                  60

<210> SEQ ID NO 4
<211> LENGTH: 63
<212> TYPE: PRT
<213> ORGANISM: Artificial Sequence
<220> FEATURE:
<223> OTHER INFORMATION: binder

<400> SEQUENCE: 4

Asp Pro Gln Phe Gly Leu Phe Ser Lys Tyr Arg Thr Pro Asn Cys Arg
1               5                   10                  15

Gln Arg Lys Gly Pro Ser Cys Gln Met Ala Phe Gln Pro Val Cys Gly
            20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
    50                  55                  60

<210> SEQ ID NO 5
<211> LENGTH: 63
<212> TYPE: PRT
<213> ORGANISM: Artificial Sequence
<220> FEATURE:
<223> OTHER INFORMATION: binder

```
<400> SEQUENCE: 5

Asp Pro Gln Phe Gly Leu Phe Ser Lys Tyr Arg Thr Pro Asn Cys Arg
1               5                   10                  15

Lys Arg Gly Gly Pro Ser Cys Gln Met Ser Tyr Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 6
<211> LENGTH: 63
<212> TYPE: PRT
<213> ORGANISM: Artificial Sequence
<220> FEATURE:
<223> OTHER INFORMATION: binder

<400> SEQUENCE: 6

Asp Pro Gln Phe Gly Leu Phe Ser Lys Tyr Arg Thr Pro Asn Cys Arg
1               5                   10                  15

Lys Val Gly Glu Pro Ala Cys Gln Met Ser Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 7
<211> LENGTH: 63
<212> TYPE: PRT
<213> ORGANISM: Artificial Sequence
<220> FEATURE:
<223> OTHER INFORMATION: binder

<400> SEQUENCE: 7

Asp Pro Gln Phe Gly Leu Phe Ser Lys Tyr Arg Thr Pro Asn Cys Met
1               5                   10                  15

Met Tyr Lys Tyr Ala Gln Cys Ser His Lys Ser Gln Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 8
<211> LENGTH: 63
<212> TYPE: PRT
<213> ORGANISM: Artificial Sequence
<220> FEATURE:
<223> OTHER INFORMATION: binder

<400> SEQUENCE: 8

Asp Pro Gln Phe Gly Leu Phe Ser Lys Tyr Arg Thr Pro Asn Cys Arg
1               5                   10                  15

Val Arg Gly Gly Pro Ser Cys Gln Met Ser Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60
```

```
<210> SEQ ID NO 9
<211> LENGTH: 63
<212> TYPE: PRT
<213> ORGANISM: Artificial Sequence
<220> FEATURE:
<223> OTHER INFORMATION: binder

<400> SEQUENCE: 9

Asp Pro Gln Phe Gly Leu Phe Ser Lys Tyr Arg Thr Pro Asn Cys Val
1               5                   10                  15

Met Tyr Lys Tyr Ala Gln Cys Ser His Lys Tyr Lys Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 10
<211> LENGTH: 63
<212> TYPE: PRT
<213> ORGANISM: Artificial Sequence
<220> FEATURE:
<223> OTHER INFORMATION: binder

<400> SEQUENCE: 10

Gly Pro Gln Phe Gly Leu Phe Ser Lys Tyr Arg Thr Pro Asn Cys Gln
1               5                   10                  15

Arg Gly Ile Gly Pro Ser Cys Gln Met Ser Tyr Lys Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 11
<211> LENGTH: 63
<212> TYPE: PRT
<213> ORGANISM: Artificial Sequence
<220> FEATURE:
<223> OTHER INFORMATION: binder

<400> SEQUENCE: 11

Gly Pro Gln Phe Gly Leu Phe Ser Lys Tyr Arg Thr Pro Asn Cys Arg
1               5                   10                  15

Thr Gly Arg Gly Pro Ala Cys Gln Met Gly Phe Gln Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 12
<211> LENGTH: 63
<212> TYPE: PRT
<213> ORGANISM: Artificial Sequence
<220> FEATURE:
<223> OTHER INFORMATION: binder
```

<400> SEQUENCE: 12

Gly Pro Gln Phe Gly Leu Phe Ser Lys Tyr Arg Thr Pro Asn Cys Arg
1               5                   10                  15

Gln Arg Lys Gly Pro Ser Cys Gln Met Ala Phe Gln Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 13
<211> LENGTH: 63
<212> TYPE: PRT
<213> ORGANISM: Artificial Sequence
<220> FEATURE:
<223> OTHER INFORMATION: binder

<400> SEQUENCE: 13

Gly Pro Gln Phe Gly Leu Phe Ser Lys Tyr Arg Thr Pro Asn Cys Arg
1               5                   10                  15

Lys Arg Gly Gly Pro Ser Cys Gln Met Ser Tyr Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 14
<211> LENGTH: 63
<212> TYPE: PRT
<213> ORGANISM: Artificial Sequence
<220> FEATURE:
<223> OTHER INFORMATION: binder

<400> SEQUENCE: 14

Gly Pro Gln Phe Gly Leu Phe Ser Lys Tyr Arg Thr Pro Asn Cys Arg
1               5                   10                  15

Lys Val Gly Glu Pro Ala Cys Gln Met Ser Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 15
<211> LENGTH: 63
<212> TYPE: PRT
<213> ORGANISM: Artificial Sequence
<220> FEATURE:
<223> OTHER INFORMATION: binder

<400> SEQUENCE: 15

Gly Pro Gln Phe Gly Leu Phe Ser Lys Tyr Arg Thr Pro Asn Cys Met
1               5                   10                  15

Met Tyr Lys Tyr Ala Gln Cys Ser His Lys Ser Gln Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

-continued

```
<210> SEQ ID NO 16
<211> LENGTH: 63
<212> TYPE: PRT
<213> ORGANISM: Artificial Sequence
<220> FEATURE:
<223> OTHER INFORMATION: binder

<400> SEQUENCE: 16

Gly Pro Gln Phe Gly Leu Phe Ser Lys Tyr Arg Thr Pro Asn Cys Arg
1               5                   10                  15

Val Arg Gly Gly Pro Ser Cys Gln Met Ser Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 17
<211> LENGTH: 63
<212> TYPE: PRT
<213> ORGANISM: Artificial Sequence
<220> FEATURE:
<223> OTHER INFORMATION: binder

<400> SEQUENCE: 17

Gly Pro Gln Phe Gly Leu Phe Ser Lys Tyr Arg Thr Pro Asn Cys Val
1               5                   10                  15

Met Tyr Lys Tyr Ala Gln Cys Ser His Lys Tyr Lys Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 18
<211> LENGTH: 63
<212> TYPE: PRT
<213> ORGANISM: Artificial Sequence
<220> FEATURE:
<223> OTHER INFORMATION: mutants
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (16)..(22)
<223> OTHER INFORMATION: Xaa can be any naturally occurring amino acid
<220> FEATURE:
<221> NAME/KEY: misc_feature
<222> LOCATION: (24)..(28)
<223> OTHER INFORMATION: Xaa can be any naturally occurring amino acid

<400> SEQUENCE: 18

Xaa Pro Gln Phe Gly Leu Phe Ser Lys Tyr Arg Thr Pro Asn Cys Xaa
1               5                   10                  15

Xaa Xaa Xaa Xaa Xaa Xaa Cys Xaa Xaa Xaa Xaa Xaa Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60
```

-continued

```
<210> SEQ ID NO 19
<211> LENGTH: 39
<212> TYPE: PRT
<213> ORGANISM: Artificial Sequence
<220> FEATURE:
<223> OTHER INFORMATION: linker

<400> SEQUENCE: 19

Gly Ser Gly Met Lys Glu Thr Ala Ala Ala Lys Phe Glu Arg Gln His
1               5                   10                  15

Met Asp Ser Pro Asp Leu Gly Thr Asp Asp Asp Lys Ala Met Ala
            20                  25                  30

Asp Ile Gly Ser Ala Asn Ser
        35

<210> SEQ ID NO 20
<211> LENGTH: 39
<212> TYPE: PRT
<213> ORGANISM: Artificial Sequence
<220> FEATURE:
<223> OTHER INFORMATION: linker

<400> SEQUENCE: 20

Gly Ser Gly Met Lys Glu Thr Ala Ala Ala Lys Phe Glu Arg Gln His
1               5                   10                  15

Met Asp Ser Pro Asp Leu Gly Thr Asp Asp Asp Lys Ala Met Ala
            20                  25                  30

Glu Asn Leu Tyr Phe Gln Gly
        35

<210> SEQ ID NO 21
<211> LENGTH: 6
<212> TYPE: PRT
<213> ORGANISM: Artificial Sequence
<220> FEATURE:
<223> OTHER INFORMATION: peptide

<400> SEQUENCE: 21

Gly Ala Ser Ala Ala Ala
1               5

<210> SEQ ID NO 22
<211> LENGTH: 5
<212> TYPE: PRT
<213> ORGANISM: Artificial Sequence
<220> FEATURE:
<223> OTHER INFORMATION: linker

<400> SEQUENCE: 22

Gly Gly Gly Gly Ser
1               5

<210> SEQ ID NO 23
<211> LENGTH: 223
<212> TYPE: PRT
<213> ORGANISM: Homo sapiens

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

```
Glu Pro Glu Val Lys Phe Asn Trp Tyr Val Asp Gly Val Glu Val His
 50                  55                  60
Asn Ala Lys Thr Lys Pro Arg Glu Glu Gln Tyr Asn Ser Thr Tyr Arg
 65                  70                  75                  80
Val Val Ser Val Leu Thr Val Leu His Gln Asp Trp Leu Asn Gly Lys
                 85                  90                  95
Glu Tyr Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Ser Arg Glu Glu Met Thr Lys Asn Gln Val Ser Leu Thr
130                 135                 140
Cys Leu Val Gly Phe Tyr Pro Ser Asp Ile Ala Val Glu Trp Glu Ser
145                 150                 155                 160
Asn Gly Gln Pro Glu Asn Asn Tyr Lys Thr Thr Pro Pro Val Leu Asp
                165                 170                 175
Ser Asp Gly Ser Phe Phe Leu Tyr Ser Lys Leu Thr Val Asp Lys Ser
            180                 185                 190
Arg Trp Gln Gln Asn Val Phe Ser Cys Ser Val Met His Glu Ala Leu
        195                 200                 205
His Asn His Tyr Thr Gln Lys Ser Leu Ser Leu Ser Pro Gly Lys
210                 215                 220

<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
aaaagaattc tgatccgcag tttggtctgt ttag                              34

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
aaaactcgag ttatgcggcc gcagacgcgc cgcacggacc                        40

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
tataccgtcg acctctagct agagcttggc                                   30

<210> SEQ ID NO 27
<211> LENGTH: 30
<212> TYPE: DNA
<213> ORGANISM: Artificial Sequence
<220> FEATURE:
<223> OTHER INFORMATION: primer
```

<400> SEQUENCE: 27
gctatggcag ggcctgccgc cccgacgttg                                       30

<210> SEQ ID NO 28
<211> LENGTH: 707
<212> TYPE: PRT
<213> ORGANISM: Homo sapiens

<400> SEQUENCE: 28

```
Met Ser Leu Trp Gln Pro Leu Val Leu Val Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350
```

```
Phe Leu Gly Lys Glu Tyr Ser Thr Cys Thr Ser Glu Gly Arg Gly Asp
            355                 360                 365
Gly Arg Leu Trp Cys Ala Thr Thr Ser Asn Phe Asp Ser Asp Lys Lys
    370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                405                 410                 415
Ala Leu Met Tyr Pro Met Tyr Arg Phe Thr Glu Gly Pro Pro Leu His
            420                 425                 430
Lys Asp Asp Val Asn Gly Ile Arg His Leu Tyr Gly Pro Arg Pro Glu
        435                 440                 445
Pro Glu Pro Arg Pro Pro Thr Thr Thr Pro Gln Pro Thr Ala Pro
    450                 455                 460
Pro Thr Val Cys Pro Thr Gly Pro Pro Thr Val His Pro Ser Glu Arg
465                 470                 475                 480
Pro Thr Ala Gly Pro Thr Gly Pro Pro Ser Ala Gly Pro Thr Gly Pro
                485                 490                 495
Pro Thr Ala Gly Pro Ser Thr Ala Thr Thr Val Pro Leu Ser Pro Val
            500                 505                 510
Asp Asp Ala Cys Asn Val Asn Ile Phe Asp Ala Ile Ala Glu Ile Gly
        515                 520                 525
Asn Gln Leu Tyr Leu Phe Lys Asp Gly Lys Tyr Trp Arg Phe Ser Glu
    530                 535                 540
Gly Arg Gly Ser Arg Pro Gln Gly Pro Phe Leu Ile Ala Asp Lys Trp
545                 550                 555                 560
Pro Ala Leu Pro Arg Lys Leu Asp Ser Val Phe Glu Glu Arg Leu Ser
                565                 570                 575
Lys Lys Leu Phe Phe Phe Ser Gly Arg Gln Val Trp Val Tyr Thr Gly
            580                 585                 590
Ala Ser Val Leu Gly Pro Arg Arg Leu Asp Lys Leu Gly Leu Gly Ala
        595                 600                 605
Asp Val Ala Gln Val Thr Gly Ala Leu Arg Ser Gly Arg Gly Lys Met
    610                 615                 620
Leu Leu Phe Ser Gly Arg Arg Leu Trp Arg Phe Asp Val Lys Ala Gln
625                 630                 635                 640
Met Val Asp Pro Arg Ser Ala Ser Glu Val Asp Arg Met Phe Pro Gly
                645                 650                 655
Val Pro Leu Asp Thr His Asp Val Phe Gln Tyr Arg Glu Lys Ala Tyr
            660                 665                 670
Phe Cys Gln Asp Arg Phe Tyr Trp Arg Val Ser Ser Arg Ser Glu Leu
        675                 680                 685
Asn Gln Val Asp Gln Val Gly Tyr Val Thr Tyr Asp Ile Leu Gln Cys
    690                 695                 700
Pro Glu Asp
705

<210> SEQ ID NO 29
<211> LENGTH: 730
<212> TYPE: PRT
<213> ORGANISM: Mus musculus
```

<400> SEQUENCE: 29

```
Met Ser Pro Trp Gln Pro Leu Leu Ala Leu Leu Ala Phe Gly Cys
1               5                   10                  15

Ser Ser Ala Ala Pro Tyr Gln Arg Gln Pro Thr Phe Val Val Phe Pro
            20                  25                  30

Lys Asp Leu Lys Thr Ser Asn Leu Thr Asp Thr Gln Leu Ala Glu Ala
            35                  40                  45

Tyr Leu Tyr Arg Tyr Gly Tyr Thr Arg Ala Ala Gln Met Met Gly Glu
    50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Gln Thr Leu Lys Ala Ile Arg
                85                  90                  95

Thr Pro Arg Cys Gly Val Pro Asp Val Gly Arg Phe Gln Thr Phe Lys
            100                 105                 110

Gly Leu Lys Trp Asp His His Asn Ile Thr Tyr Trp Ile Gln Asn Tyr
        115                 120                 125

Ser Glu Asp Leu Pro Arg Asp Met Ile Asp Asp Ala Phe Ala Arg Ala
    130                 135                 140

Phe Ala Val Trp Gly Glu Val Ala Pro Leu Thr Phe Thr Arg Val Tyr
145                 150                 155                 160

Gly Pro Glu Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Ala Gly Val Gln Gly Asp Ala His Phe Asp Asp Asp Glu
        195                 200                 205

Leu Trp Ser Leu Gly Lys Gly Val Val Ile Pro Thr Tyr Tyr Gly Asn
    210                 215                 220

Ser Asn Gly Ala Pro Cys His Phe Pro Phe Thr Phe Glu Gly Arg Ser
225                 230                 235                 240

Tyr Ser Ala Cys Thr Thr Asp Gly Arg Asn Asp Gly Thr Pro Trp Cys
                245                 250                 255

Ser Thr Thr Ala Asp Tyr Asp Lys Asp Gly Lys Phe Gly Phe Cys Pro
            260                 265                 270

Ser Glu Arg Leu Tyr Thr Glu His Gly Asn Gly Glu Gly Lys Pro Cys
        275                 280                 285

Val Phe Pro Phe Ile Phe Glu Gly Arg Ser Tyr Ser Ala Cys Thr Thr
    290                 295                 300

Lys Gly Arg Ser Asp Gly Tyr Arg Trp Cys Ala Thr Thr Ala Asn Tyr
305                 310                 315                 320

Asp Gln Asp Lys Leu Tyr Gly Phe Cys Pro Thr Arg Val Asp Ala Thr
                325                 330                 335

Val Val Gly Gly Asn Ser Ala Gly Glu Leu Cys Val Phe Pro Phe Val
            340                 345                 350

Phe Leu Gly Lys Gln Tyr Ser Ser Cys Thr Ser Asp Gly Arg Arg Asp
        355                 360                 365

Gly Arg Leu Trp Cys Ala Thr Thr Ser Asn Phe Asp Thr Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415
```

-continued

Ala Leu Met Tyr Pro Leu Tyr Ser Tyr Leu Glu Gly Phe Pro Leu Asn
            420                 425                 430

Lys Asp Asp Ile Asp Gly Ile Gln Tyr Leu Tyr Gly Arg Gly Ser Lys
        435                 440                 445

Pro Asp Pro Arg Pro Pro Ala Thr Thr Thr Thr Glu Pro Gln Pro Thr
    450                 455                 460

Ala Pro Pro Thr Met Cys Pro Thr Ile Pro Pro Thr Ala Tyr Pro Thr
465                 470                 475                 480

Val Gly Pro Thr Val Gly Pro Thr Gly Ala Pro Ser Pro Gly Pro Thr
                485                 490                 495

Ser Ser Pro Ser Pro Gly Pro Thr Gly Ala Pro Ser Pro Gly Pro Thr
            500                 505                 510

Ala Pro Pro Thr Ala Gly Ser Ser Glu Ala Ser Thr Glu Ser Leu Ser
        515                 520                 525

Pro Ala Asp Asn Pro Cys Asn Val Asp Val Phe Asp Ala Ile Ala Glu
    530                 535                 540

Ile Gln Gly Ala Leu His Phe Phe Lys Asp Gly Trp Tyr Trp Lys Phe
545                 550                 555                 560

Leu Asn His Arg Gly Ser Pro Leu Gln Gly Pro Phe Leu Thr Ala Arg
                565                 570                 575

Thr Trp Pro Ala Leu Pro Ala Thr Leu Asp Ser Ala Phe Glu Asp Pro
            580                 585                 590

Gln Thr Lys Arg Val Phe Phe Ser Gly Arg Gln Met Trp Val Tyr
        595                 600                 605

Thr Gly Lys Thr Val Leu Gly Pro Arg Ser Leu Asp Lys Leu Gly Leu
    610                 615                 620

Gly Pro Glu Val Thr His Val Ser Gly Leu Leu Pro Arg Arg Leu Gly
625                 630                 635                 640

Lys Ala Leu Leu Phe Ser Lys Gly Arg Val Trp Arg Phe Asp Leu Lys
                645                 650                 655

Ser Gln Lys Val Asp Pro Gln Ser Val Ile Arg Val Asp Lys Glu Phe
            660                 665                 670

Ser Gly Val Pro Trp Asn Ser His Asp Ile Phe Gln Tyr Gln Asp Lys
        675                 680                 685

Ala Tyr Phe Cys His Gly Lys Phe Phe Trp Arg Val Ser Phe Gln Asn
    690                 695                 700

Glu Val Asn Lys Val Asp His Glu Val Asn Gln Val Asp Asp Val Gly
705                 710                 715                 720

Tyr Val Thr Tyr Asp Leu Leu Gln Cys Pro
                725                 730

<210> SEQ ID NO 30
<211> LENGTH: 7
<212> TYPE: PRT
<213> ORGANISM: Artificial Sequence
<220> FEATURE:
<223> OTHER INFORMATION: substrate
<220> FEATURE:
<221> NAME/KEY: BINDING
<222> LOCATION: (1)..(1)
<223> OTHER INFORMATION: Xaa is (7-methoxycoumarin-4-yl)acetyl-L-lysine
<220> FEATURE:
<221> NAME/KEY: BINDING
<222> LOCATION: (6)..(6)
<223> OTHER INFORMATION: Xaa is
    [Nbeta-(2,4-dinitrophenyl)-L-2,3-diaminopropinyl]-L-alanine

```
<220> FEATURE:
<221> NAME/KEY: BINDING
<222> LOCATION: (7)..(7)
<223> OTHER INFORMATION: Xaa is L-arginine amide

<400> SEQUENCE: 30

Xaa Pro Leu Gly Leu Xaa Xaa
1               5

<210> SEQ ID NO 31
<211> LENGTH: 6
<212> TYPE: PRT
<213> ORGANISM: Artificial Sequence
<220> FEATURE:
<223> OTHER INFORMATION: substrate
<220> FEATURE:
<221> NAME/KEY: BINDING
<222> LOCATION: (1)..(1)
<223> OTHER INFORMATION: Xaa is (7-methoxycoumarin-4-yl)acetyl-L-proline
<220> FEATURE:
<221> NAME/KEY: BINDING
<222> LOCATION: (5)..(5)
<223> OTHER INFORMATION: Xaa is
      [Nbeta-(2,4-dinitrophenyl)-L-2,3-diaminopropinyl]-L-alanine
<220> FEATURE:
<221> NAME/KEY: BINDING
<222> LOCATION: (6)..(6)
<223> OTHER INFORMATION: Xaa is L-arginine amide

<400> SEQUENCE: 31

Xaa Leu Gly Leu Xaa Xaa
1               5

<210> SEQ ID NO 32
<211> LENGTH: 7
<212> TYPE: PRT
<213> ORGANISM: Artificial Sequence
<220> FEATURE:
<223> OTHER INFORMATION: substrate
<220> FEATURE:
<221> NAME/KEY: BINDING
<222> LOCATION: (1)..(1)
<223> OTHER INFORMATION: Xaa is N-(2,4-dinitrophenyl)-L-proline

<400> SEQUENCE: 32

Xaa Leu Gly Met Trp Ser Arg
1               5

<210> SEQ ID NO 33
<211> LENGTH: 10
<212> TYPE: PRT
<213> ORGANISM: Artificial Sequence
<220> FEATURE:
<223> OTHER INFORMATION: substrate
<220> FEATURE:
<221> NAME/KEY: BINDING
<222> LOCATION: (1)..(1)
<223> OTHER INFORMATION: Xaa is (7-methoxycoumarin-4-yl)acetyl-L-alanine
<220> FEATURE:
<221> NAME/KEY: BINDING
<222> LOCATION: (7)..(7)
<223> OTHER INFORMATION: Xaa is L-norvaline
<220> FEATURE:
<221> NAME/KEY: BINDING
<222> LOCATION: (10)..(10)
<223> OTHER INFORMATION: Xaa is [Nepsilon-(2,4-dinitrophenyl)]-L-lysine
      amide

<400> SEQUENCE: 33

Xaa Pro Lys Pro Val Glu Xaa Trp Arg Xaa
1               5                   10
```

```
<210> SEQ ID NO 34
<211> LENGTH: 8
<212> TYPE: PRT
<213> ORGANISM: Artificial Sequence
<220> FEATURE:
<223> OTHER INFORMATION: tag

<400> SEQUENCE: 34

Asp Tyr Lys Asp Asp Asp Asp Lys
1               5

<210> SEQ ID NO 35
<211> LENGTH: 17
<212> TYPE: PRT
<213> ORGANISM: Artificial Sequence
<220> FEATURE:
<223> OTHER INFORMATION: tag

<400> SEQUENCE: 35

Gly Gly Gly Leu Asn Asp Ile Phe Glu Ala Gln Lys Ile Glu Trp His
1               5                   10                  15

Glu

<210> SEQ ID NO 36
<211> LENGTH: 4
<212> TYPE: PRT
<213> ORGANISM: Artificial Sequence
<220> FEATURE:
<223> OTHER INFORMATION: substrate
<220> FEATURE:
<221> NAME/KEY: BINDING
<222> LOCATION: (1)..(1)
<223> OTHER INFORMATION: X is succinyl leucine
<220> FEATURE:
<221> NAME/KEY: BINDING
<222> LOCATION: (4)..(4)
<223> OTHER INFORMATION: X is 4-methylcoumaryl-tyrosine-7-amide

<400> SEQUENCE: 36

Xaa Leu Val Xaa
1

<210> SEQ ID NO 37
<211> LENGTH: 4
<212> TYPE: PRT
<213> ORGANISM: Artificial Sequence
<220> FEATURE:
<223> OTHER INFORMATION: substrate
<220> FEATURE:
<221> NAME/KEY: BINDING
<222> LOCATION: (1)..(1)
<223> OTHER INFORMATION: X is succinyl alanine
<220> FEATURE:
<221> NAME/KEY: BINDING
<222> LOCATION: (4)..(4)
<223> OTHER INFORMATION: X is 4-methylcoumaryl-phenylalanine-7-amide

<400> SEQUENCE: 37

Xaa Ala Pro Xaa
1

<210> SEQ ID NO 38
<211> LENGTH: 4
<212> TYPE: PRT
<213> ORGANISM: Artificial Sequence
<220> FEATURE:
<223> OTHER INFORMATION: substrate
```

```
<220> FEATURE:
<221> NAME/KEY: BINDING
<222> LOCATION: (1)..(1)
<223> OTHER INFORMATION: X is N-Methoxysuccinyl alanine
<220> FEATURE:
<221> NAME/KEY: BINDING
<222> LOCATION: (4)..(4)
<223> OTHER INFORMATION: X is 4-methylcoumaryl-valine-7-amide

<400> SEQUENCE: 38

Xaa Ala Pro Xaa
1

<210> SEQ ID NO 39
<211> LENGTH: 4
<212> TYPE: PRT
<213> ORGANISM: Artificial Sequence
<220> FEATURE:
<223> OTHER INFORMATION: substrate
<220> FEATURE:
<221> NAME/KEY: BINDING
<222> LOCATION: (1)..(1)
<223> OTHER INFORMATION: X is t-butyloxycarbonyl leucine
<220> FEATURE:
<221> NAME/KEY: BINDING
<222> LOCATION: (4)..(4)
<223> OTHER INFORMATION: X is 4-methylcoumaryl-arginine-7-amide

<400> SEQUENCE: 39

Xaa Ser Thr Xaa
1

<210> SEQ ID NO 40
<211> LENGTH: 5
<212> TYPE: PRT
<213> ORGANISM: Artificial Sequence
<220> FEATURE:
<223> OTHER INFORMATION: recognition site

<400> SEQUENCE: 40

Asp Asp Asp Asp Lys
1               5

<210> SEQ ID NO 41
<211> LENGTH: 707
<212> TYPE: PRT
<213> ORGANISM: Macaca fascicularis

<400> SEQUENCE: 41

Met Ser Leu Trp Gln Pro Leu Val Leu Ala Leu Leu Val Leu Gly Cys
1               5                   10                  15

Cys Cys Ala Ala Pro Arg Gln Arg Gln Ser Thr Leu Val Leu Phe Pro
            20                  25                  30

Gly Asp Leu Lys Thr Asn Leu Thr Asp Arg Gln Leu Ala Glu Asp Tyr
        35                  40                  45

Leu Tyr Arg Tyr Gly Tyr Thr Arg Val Ala Glu Met His Gly Asp Ser
    50                  55                  60

Lys Ser Leu Gly Pro Ala Leu Leu Leu Gln Lys Gln Leu Ser Leu
65                  70                  75                  80

Pro Gln Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His Asn Ile Thr Tyr Trp Ile Gln Asn Tyr
        115                 120                 125
```

```
Ser Glu Asp Leu Pro Arg Ala Val Ile Glu Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
            165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
            195                 200                 205

Leu Trp Ser Leu Gly Lys Gly Val Val Val Pro Thr Lys Phe Gly Asn
210                 215                 220

Ala Asp Gly Ala Ala Cys His Phe Pro Phe Thr Phe Glu Gly Arg Ser
225                 230                 235                 240

Tyr Ser Ala Cys Thr Thr Asp Gly Arg Ser Asp Gly Val Pro Trp Cys
            245                 250                 255

Ser Thr Thr Ala Asn Tyr Asp Thr Asp Arg Arg Phe Gly Phe Cys Pro
            260                 265                 270

Ser Glu Arg Leu Tyr Thr Gln Asp Gly Asn Ala Asp Gly Lys Pro Cys
            275                 280                 285

Gln Phe Pro Phe Ile Phe Gln Gly Gln Ser Tyr Ser Ala Cys Thr Thr
            290                 295                 300

Asp Gly Arg Ser Asp Gly Tyr Arg Trp Cys Ala Thr Thr Ala Asn Tyr
305                 310                 315                 320

Asp Gln Asp Lys Leu Tyr Gly Phe Cys Pro Thr Arg Ala Asp Ser Thr
            325                 330                 335

Val Ile Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Arg Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Thr Ser Val Pro Glu
            405                 410                 415

Ala Leu Met Tyr Pro Met Tyr Arg Phe Thr Glu Glu Pro Pro Leu His
            420                 425                 430

Lys Asp Asp Val Asn Gly Ile Gln Tyr Leu Tyr Gly Ser Arg Pro Glu
            435                 440                 445

Pro Glu Pro Arg Pro Pro Thr Thr Thr Thr Pro Gln Pro Thr Ala Pro
450                 455                 460

Pro Thr Val Cys Pro Thr Gly Pro Pro Thr Val Arg Pro Ser Asp Arg
465                 470                 475                 480

Pro Thr Ala Gly Pro Thr Gly Pro Pro Ser Ala Gly Pro Thr Gly Pro
            485                 490                 495

Pro Thr Ala Gly Pro Ser Thr Thr Thr Val Pro Leu Asn Pro Val
            500                 505                 510

Asp Asp Ala Cys Asn Val Asn Ile Phe Asp Ala Ile Thr Glu Ile Gly
            515                 520                 525

Asn Gln Leu Tyr Leu Phe Lys Asp Gly Arg Tyr Trp Arg Phe Ser Glu
530                 535                 540
```

```
Arg Arg Gly Ser Arg Leu Gln Gly Pro Phe Leu Ile Ala Asp Thr Trp
545                 550                 555                 560

Pro Ala Leu Pro Arg Lys Leu Asp Ser Ala Phe Glu Glu Pro Leu Ser
                565                 570                 575

Lys Lys Leu Phe Phe Phe Ser Gly Arg Gln Val Trp Val Tyr Thr Gly
                580                 585                 590

Ser Ser Val Leu Gly Pro Arg Leu Asp Lys Leu Gly Leu Gly Ala
            595                 600                 605

Asp Val Ala Gln Val Thr Gly Ala Leu Arg Arg Gly Ala Gly Lys Met
                610                 615                 620

Leu Leu Phe Ser Gly Arg Arg Phe Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Gln Glu Lys Ala Tyr
                660                 665                 670

Phe Cys Gln Asp Arg Phe Tyr Trp Arg Val Ser Ser Gln Ser Gly Val
                675                 680                 685

Asn Gln Val Asp Gln Val Gly Tyr Val Thr Tyr Asp Ile Leu Gln Cys
690                 695                 700

Pro Glu Asp
705

<210> SEQ ID NO 42
<211> LENGTH: 708
<212> TYPE: PRT
<213> ORGANISM: Rattus norvegicus

<400> SEQUENCE: 42

Met Ser Pro Trp Gln Pro Leu Leu Leu Val Leu Leu Ala Leu Gly Tyr
1               5                   10                  15

Ser Phe Ala Ala Pro His Gln Arg Gln Pro Thr Tyr Val Val Phe Pro
                20                  25                  30

Arg Asp Leu Lys Thr Ser Asn Leu Thr Asp Thr Gln Leu Ala Glu Asp
                35                  40                  45

Tyr Leu Tyr Arg Tyr Gly Tyr Thr Arg Ala Ala Gln Met Met Gly Glu
    50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Glu Thr Leu Lys Ala Ile Arg
                85                  90                  95

Ser Pro Arg Cys Gly Val Pro Asp Val Gly Lys Phe Gln Thr Phe Asp
                100                 105                 110

Gly Asp Leu Lys Trp His His His Asn Ile Thr Tyr Trp Ile Gln Ser
                115                 120                 125

Tyr Thr Glu Asp Leu Pro Arg Asp Val Ile Asp Ser Phe Ala Arg
    130                 135                 140

Ala Phe Ala Val Trp Ser Ala Val Thr Pro Leu Thr Phe Thr Arg Val
145                 150                 155                 160

Tyr Gly Leu Glu Ala Asp Ile Val Ile Gln Phe Gly Val Ala Glu His
                165                 170                 175

Gly Asp Gly Tyr Pro Phe Asp Gly Lys Asp Gly Leu Leu Ala His Ala
                180                 185                 190

Phe Pro Pro Gly Pro Gly Ile Gln Gly Asp Ala His Phe Asp Asp Asp
                195                 200                 205
```

```
Glu Leu Trp Ser Leu Gly Lys Gly Ala Val Val Pro Thr Tyr Phe Gly
210                 215                 220

Asn Ala Asn Gly Ala Pro Cys His Phe Pro Phe Thr Phe Glu Gly Arg
225                 230                 235                 240

Ser Tyr Leu Ser Cys Thr Thr Asp Gly Arg Asn Asp Gly Lys Pro Trp
                245                 250                 255

Cys Gly Thr Thr Ala Asp Tyr Asp Thr Asp Arg Lys Tyr Gly Phe Cys
                260                 265                 270

Pro Ser Glu Asn Leu Tyr Thr Glu His Gly Asn Gly Asp Gly Lys Pro
            275                 280                 285

Cys Val Phe Pro Phe Ile Phe Glu Gly His Ser Tyr Ser Ala Cys Thr
290                 295                 300

Thr Lys Gly Arg Ser Asp Gly Tyr Arg Trp Cys Ala Thr Thr Ala Asn
305                 310                 315                 320

Tyr Asp Gln Asp Lys Ala Asp Gly Phe Cys Pro Thr Arg Ala Asp Val
                325                 330                 335

Thr Val Thr Gly Gly Asn Ser Ala Gly Glu Met Cys Val Phe Pro Phe
                340                 345                 350

Val Phe Leu Gly Lys Gln Tyr Ser Thr Cys Thr Ser Glu Gly Arg Ser
                355                 360                 365

Asp Gly Arg Leu Trp Cys Ala Thr Thr Ser Asn Phe Asp Ala Asp Lys
370                 375                 380

Lys Trp Gly Phe Cys Pro Asp Gln Gly Tyr Ser Leu Phe Leu Val Ala
385                 390                 395                 400

Ala His Glu Phe Gly His Ala Leu Gly Leu Asp His Ser Ser Val Pro
                405                 410                 415

Glu Ala Leu Met Tyr Pro Met Tyr His Tyr His Glu Asp Ser Pro Leu
                420                 425                 430

His Glu Asp Asp Ile Lys Gly Ile His His Leu Tyr Gly Arg Gly Ser
                435                 440                 445

Lys Pro Asp Pro Arg Pro Pro Ala Thr Thr Ala Ala Glu Pro Gln Pro
450                 455                 460

Thr Ala Pro Pro Thr Met Cys Ser Thr Ala Pro Pro Met Ala Tyr Pro
465                 470                 475                 480

Thr Gly Gly Pro Thr Val Ala Pro Thr Gly Ala Pro Ser Pro Gly Pro
                485                 490                 495

Thr Gly Pro Pro Thr Ala Gly Pro Ser Glu Ala Pro Thr Glu Ser Ser
                500                 505                 510

Thr Pro Asp Asp Asn Pro Cys Asn Val Asp Val Phe Asp Ala Ile Ala
                515                 520                 525

Asp Ile Gln Gly Ala Leu His Phe Phe Lys Asp Gly Arg Tyr Trp Lys
530                 535                 540

Phe Ser Asn His Gly Gly Asn Gln Leu Gln Gly Pro Phe Leu Ile Ala
545                 550                 555                 560

Arg Thr Trp Pro Ala Phe Pro Ser Lys Leu Asn Ser Ala Phe Glu Asp
                565                 570                 575

Pro Gln Pro Lys Lys Ile Phe Phe Phe Leu Trp Ala Gln Met Trp Val
                580                 585                 590

Tyr Thr Gly Gln Ser Val Leu Gly Pro Arg Ser Leu Asp Lys Leu Gly
                595                 600                 605

Leu Gly Ser Glu Val Thr Leu Val Thr Gly Leu Leu Pro Arg Arg Gly
610                 615                 620
```

```
Gly Lys Ala Leu Leu Ile Ser Arg Glu Arg Ile Trp Lys Phe Asp Leu
625                 630                 635                 640

Lys Ser Gln Lys Val Asp Pro Gln Ser Val Thr Arg Leu Asp Asn Glu
                645                 650                 655

Phe Ser Gly Val Pro Trp Asn Ser His Asn Val Phe Gln Tyr Gln Asp
            660                 665                 670

Lys Ala Tyr Phe Cys His Asp Lys Tyr Phe Trp Arg Val Ser Phe His
        675                 680                 685

Asn Arg Val Asn Gln Val Asp His Val Ala Tyr Val Thr Tyr Asp Leu
        690                 695                 700

Leu Gln Cys Pro
705
```